US006392749B1

(12) United States Patent
Meeks et al.

(10) Patent No.: US 6,392,749 B1
(45) Date of Patent: May 21, 2002

(54) HIGH SPEED OPTICAL PROFILOMETER FOR MEASURING SURFACE HEIGHT VARIATION

(75) Inventors: Steven W. Meeks; Rusmin Kudinar, both of Fremont, CA (US)

(73) Assignee: Candela Instruments, Fremont, CA (US)

( * ) Notice: Subject to any disclaimer, the term of this patent is extended or adjusted under 35 U.S.C. 154(b) by 0 days.

(21) Appl. No.: 09/718,054

(22) Filed: Nov. 20, 2000

Related U.S. Application Data

(63) Continuation-in-part of application No. 09/347,622, filed on Jul. 2, 1999, which is a continuation-in-part of application No. 09/414,388, filed on Oct. 7, 1999, which is a continuation-in-part of application No. 09/136,897, filed on Aug. 19, 1998, now Pat. No. 6,031,615.

(60) Provisional application No. 60/059,740, filed on Sep. 22, 1997.

(51) Int. Cl.[7] .............................................. G01B 11/06
(52) U.S. Cl. ...................................................... 356/381
(58) Field of Search .............................. 356/381, 601, 356/602, 607, 608, 614, 622, 623, 630, 631, 369

(56) References Cited

U.S. PATENT DOCUMENTS

| | | | |
|---|---|---|---|
| 3,885,875 A | 5/1975 | Rosenfeld et al. | 356/120 |
| 4,873,430 A | 10/1989 | Juliana et al. | 250/225 |
| 5,293,216 A | 3/1994 | Moslehi | 356/371 |
| 5,726,455 A | 3/1998 | Vurens | 250/559.28 |
| 5,951,891 A | 9/1999 | Barenboim et al. | 219/121.68 |
| 5,978,091 A | 11/1999 | Jann et al. | 356/376 |
| 5,986,761 A | 11/1999 | Crawforth et al. | 356/371 |
| 6,134,011 A | 10/2000 | Klein et al. | 356/369 |
| 6,307,627 B1 | 10/2001 | Vurens | 356/369 |

FOREIGN PATENT DOCUMENTS

JP 3-221804 9/1991

OTHER PUBLICATIONS

W.C. Leung, W. Crooks, H. Rosen and T. Strand, An Optical Method Using a Laser and an Integrating Sphere Combination for Characterizing the Thickness Profile of Magnetic Media, Sep. 1989, IEEE Transaction on Magnetics, vol. 25, No. 5. pp. 3659–3661.
Steven W. Meeks, Walter E. Weresin, and Hal J. Rosen, Optical Surface Analysis of the Head–Disk–Interface of Thin Film Disks, Jan. 1995, Transactions on the ASME, Journal of Tribology, vol. 117, pp. 112–118.
Steven Meeks and Rusmin Kudinar, The Next Battleground: Head–Disk Interface, Mar. 1998, Data Storage, Test & Measurement, pp. 29–30, 34 and 38.
Laser Scanning Surface Profilometer, [online], Aug. 1970, [retrieved Jan. 29, 2001], pp. 789–790, Retrieved from the Internet: <URL: http://www.delphion.com/tdbs/tdb?&order=70C101758.

*Primary Examiner*—Frank G. Font
*Assistant Examiner*—Tu T. Nguyen
(74) *Attorney, Agent, or Firm*—Fenwick & West, LLP

(57) ABSTRACT

A system and a method for measuring a height of a thin film disk or a silicon wafer having a first and a second electromagnetic signal source for generating a first and a second signal toward a first position on the thin film magnetic disk at two different angles, a first and a second sensitive detector positioned at a right angle from each other to receive a reflected portion of the first and the second signal that reflects off of the object, and to determine a radial portion of the first and the second signals and a circumferential portion of the first and the second signals. The system also includes a processor for determining the height of the first position based upon a difference between the circumferential portion of the second signal and the circumferential portion of the first signal that does not include slope information.

28 Claims, 31 Drawing Sheets

P Polarized
Specular Light

S Polarized
Specular Light

P or S Polarized
Scattered Light

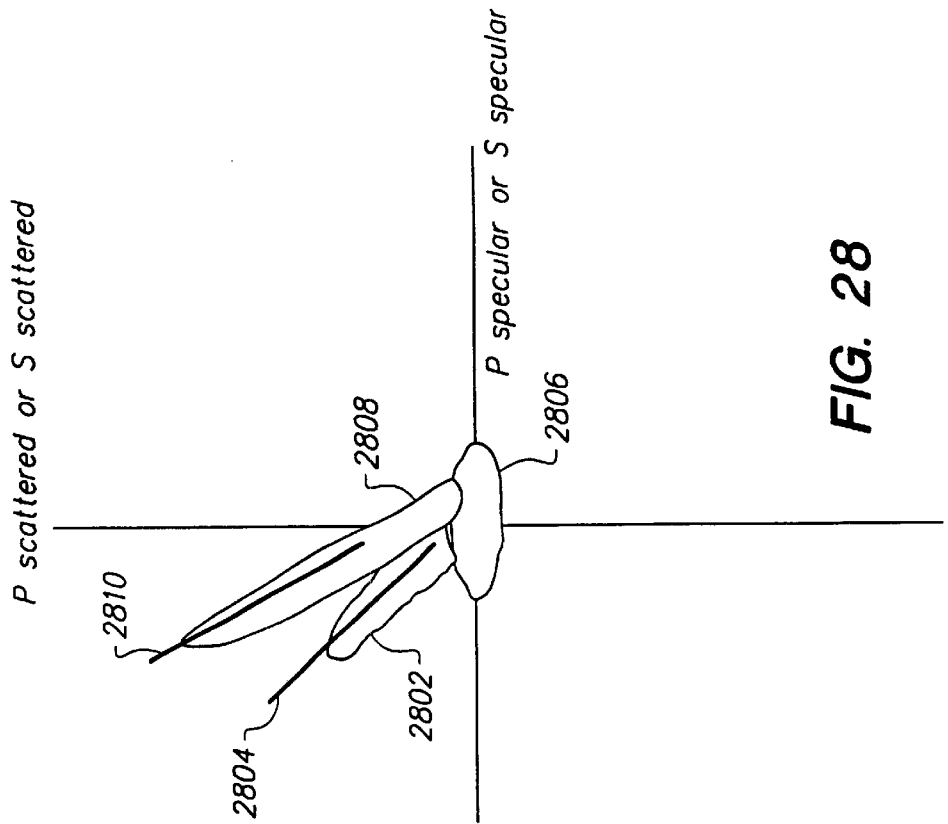
FIG. 28
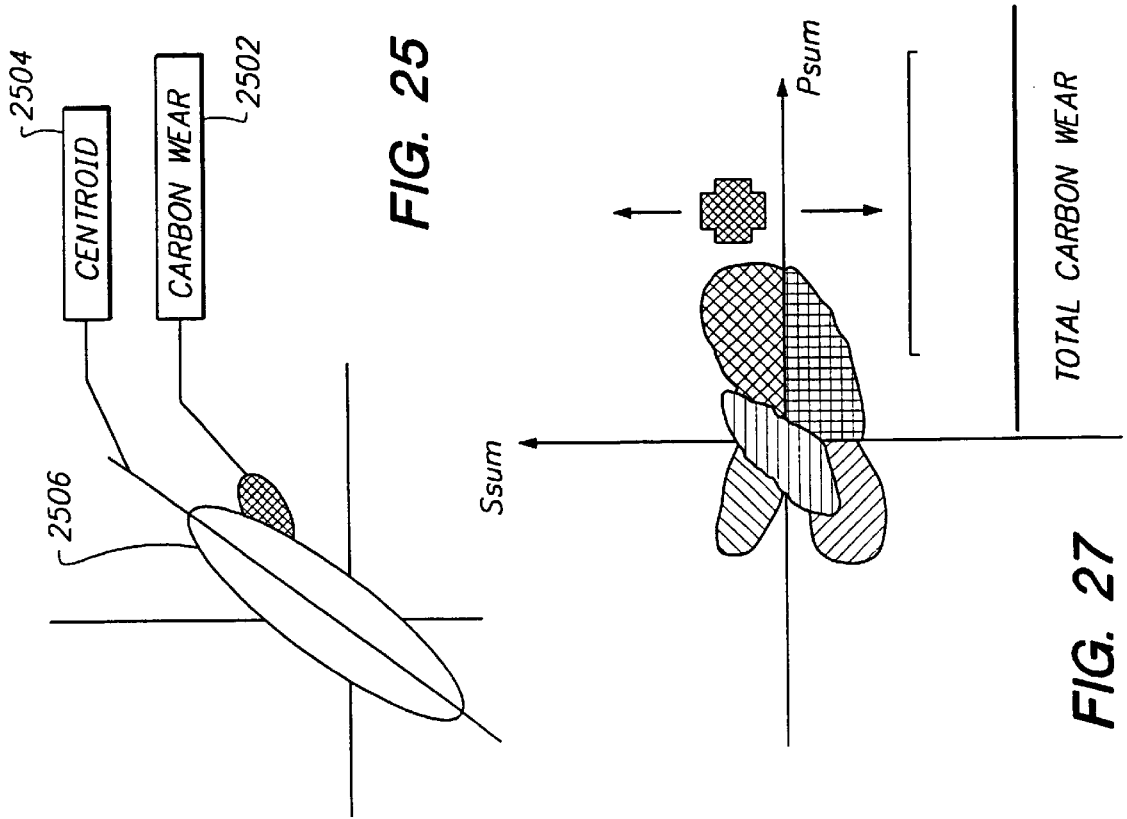
FIG. 25
FIG. 27

HIGH SPEED OPTICAL PROFILOMETER FOR MEASURING SURFACE HEIGHT VARIATION

RELATED APPLICATIONS

This application is a continuation-in-part of U.S. patent application Ser. No. 09/347,622 filed on Jul. 2, 1999, which is a continuation-in-part of U.S. patent application Ser. No. 09/414,388 filed on Oct. 7, 1999, which is a continuation-in-part of U.S. patent application Ser. No. 09/136,897 filed on Aug. 19, 1998, now U.S. Pat. No. 6,031,615, which claims priority from provisional application No. 60/059,740 filed on Sep. 22, 1997 which are all incorporated by reference herein in their entirety.

BACKGROUND OF THE INVENTION

1. Field of the Invention

The present invention is directed toward measuring thin films including silicon wafers and more particularly toward measuring lubricant thickness, lubricant degradation, thin film thickness and wear, and surface roughness using a laser directed toward a thin film disk at many angles including non-Brewster's angles of an absorbing layer of the thin film.

2. Description of Background Art

Coated thin film disks are used in a variety of industries. One example is the computer hard disk industry. A computer hard disk (magnetic storage device) is a non-volatile memory device that can store large amounts of data. One problem that the manufacturers of hard disks experience is how to maximize the operating life of a hard disk. When a hard disk fails the data stored therein may be difficult, expensive, or impossible to retrieve.

A schematic of a thin film disk used in magnetic storage devices is shown in FIG. 1. It includes a magnetic thin film (layer) 106 which is deposited upon a substrate 108 (typically a NiP plated Al—Mg alloy or glass). The magnetic thin film 106 can be protected by a thin film of carbon 104 (carbon layer), for example, whose thickness is typically 50 to 200 Angstroms (Å). The carbon layer 104 is typically coated with a thin layer (10 to 30 Angstroms) of a fluorocarbon lubricant 102 (lubricant layer). The lubricant layer 102 serves to increase the durability of the underlying carbon layer 104 particularly when the magnetic read/write head contacts the disk, for example when the disk drive is turned off, as described below. During the development and testing of thin film disks it is necessary to subject thin film magnetic disks to numerous starts and stops of the read/write head. The start/stops cause the read/write head to contact the thin film disk 100 in a dedicated region of the thin film disk 100 known as the start/stop zone. The action of stopping and starting the thin film head on the start/stop zone can cause depletion and/or degradation of the fluorocarbon lubricant layer 102, wear of the carbon layer 104 and changes in the surface roughness. A conventional technique for measuring thin film characteristics are discussed in U.S. Pat. No. 4,873,430 which is incorporated by reference herein in its entirety. This patent describes a technique that uses a P polarized collimated (unfocussed) laser propagating at the Brewster's angle of the film to measure film thickness and surface roughness.

U.S. Pat. No. 5,726,455 describes an optical system for measuring only the specular component of light reflected from a thin film magnetic disk. The patent purports that the system is able to measure lubricant coating thickness and coating wear. This system uses a temperature stabilized (Peltier effect cooled) light source and an integrating sphere detector which is remotely located from the disk. The angle of incidence is between the Brewster's angle of the lubricant and that of the adjacent layer. This invention makes no provision for the measurement of the scattered light nor does it measure surface roughness.

Other techniques for measuring surface roughness are discussed in U.S. Pat. Nos. 5,608,527, 5,196,906, 5,313,542, 4,668,860, 5,406,082 and in the book "Optical Scattering-Measurement and Analysis" second edition by John C. Stover, SPIE Press, Bellingham, Wash., 1995 on page 169 through 170, which are all incorporated by reference herein in their entirety. These references relate to obtaining the surface roughness and do not address identifying lubricant thickness and degradation or thin film thickness or wear.

Specifically, U.S. Pat. No. 5,608,527 describes a technique for measuring the specular and scattered light in one scattering plane by using a multi-segmented array. The specular and scattered lights are used to obtain the surface roughness. U.S. Pat. No. 5,196,906 describes a modular scatterometer for determining surface roughness from an array of detectors positioned along a hemisphere. U.S. Pat. No. 5,313,542 describes a scatterometer which uses depolarized light from a laser diode and fiber optic bundles to collect partial or full hemispherically scattered light. U.S. Pat. No. 4,668,860 describes a scatterometer for evaluating the surface quality of an optical element which has both bulk and surface scatter. This patent describes a technique that purports to separate surface and bulk scatter by using the polarization characteristics of the light. U.S. Pat. No. 5,406,082 describes a surface inspection and characterization system that uses a broadband infrared light source which is directed onto the surface to be inspected. The reflected light is separated into several wavelengths and these signals are used to characterize the surface by such properties as absorbency.

A technique for combining the measurement of thin film thickness and surface roughness is described in a brochure by AHEAD Optoelectronics, Inc., Taipei, Taiwan, R.O.C, which is incorporated by reference herein in its entirety. This describes an instrument called an Integrating Sphere Ellipsometry Analyzer. This instrument is a combined ellipsometer and integrating sphere analyzer. This brochure teaches a measurement technique that uses an ellipsometric technique for the ex situ measurement of absolute film thickness and indices of refraction. This technique also uses an integrating sphere to measure surface microroughness at a variable angle. The system as described is designed for ex situ measurement of film thickness and surface microroughness, it is not capable of measuring in situ wear, lubricant and surface roughness.

A technique for measuring thin film properties at Brewster's angle is described in S. Meeks et. al., *Optical Surface Analysis of the Head-Disk-Interface of Thin Film Disks*, ASME Transactions on Tribology, Vol. 117, pp. 112–118, (January 1995), which is incorporated by reference herein in its entirety.

None of these references teach a single system and method for performing all of these measurements in situ. In addition, references Meeks et al. and Juliana et al. teach that the measurement should occur at substantially Brewster's angle of the carbon 104. U.S. Pat. No, 5,726,455 teaches that the measurement should occur between Brewster's angle of the lubricant and that of the adjacent layer. A stated benefit of using this angle is that the light signal will not reflect off of the carbon 104 and instead will pass directly through the carbon 104 and reflect off of the magnetic layer 106.

What is needed is a system and method for examining thin film disks that: (1) measures the amount of lubricant thickness and thickness change; (2) measures the extent of lubricant degradation; (3) measures the wear and thickness of the carbon layer; (4) measures the absolute surface roughness and changes in the surface roughness; (5) performs magnetic imaging; (6) performs optical profiling; and (7) enables these measurements to be (a) performed simultaneously, (b) performed at an angle of incidence that is substantially different from Brewster's angle, and (c) performed in situ or ex situ.

SUMMARY OF THE INVENTION

A system and method for measuring the height of a thin film disk or a silicon wafer having a first electromagnetic signal source for generating a first signal toward a first position on the thin film magnetic disk at a first angle, a second electromagnetic signal source for generating a second signal toward the first position on the thin film magnetic disk at a second angle, a spinning device for rotating the object to change the first position, a first position sensitive detector to receive a portion of said first signal that reflects off of the object, and to determine a radial portion of the first signal (S1$r$) and a circumferential portion of said first signal (S1$c$), a second position sensitive detector positioned at a right angle from the first position sensitive detector, to receive a reflected portion of the second signal that reflects off of the object, and to determine a radial portion of the second signal (S2$r$) and a circumferential portion of the second signal (S2$c$). The system also includes a processor for determining the height of the first position based upon a difference between S2$c$ and S1$c$ that does not include slope information.

BRIEF DESCRIPTION OF THE DRAWINGS

FIG. 25 is an example of a simplified two-dimensional (2D) histogram image according to an embodiment of the present invention.

FIG. 27 illustrates one example of histogram analysis according to the AND/NOT unit of the present invention.

FIG. 28 illustrates one example of histogram analysis using P specular or S specular versus P scattered or S scattered variable according to the AND/NOT unit of the present invention.

DETAILED DESCRIPTION OF THE PREFERRED EMBODIMENTS

A preferred embodiment of the present invention is now described with reference to the figures where like reference numbers indicate identical or functionally similar elements. Also in the figures, the left most digit(s) of each reference number correspond(s) to the figure in which the reference number is first used.

Figure 2:
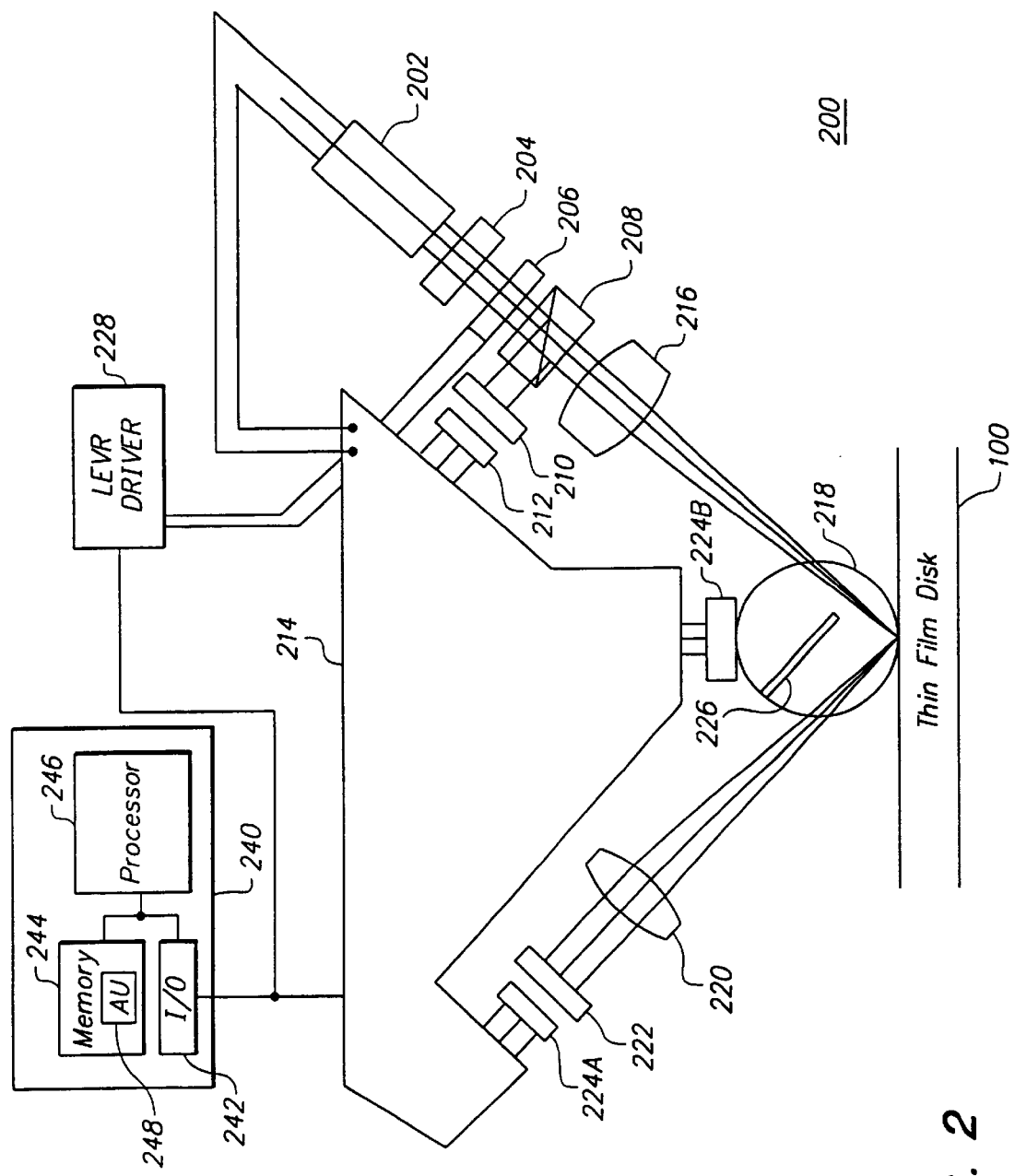
FIG. 2 is an illustration of an apparatus for measuring properties of the thin film according to an embodiment of the present invention.

FIG. 2 is an illustration of an apparatus for measuring properties of the thin film according to an embodiment of the present invention. The apparatus uses a focused laser light signal whose angle of propagation can be between zero degrees from normal and ninety degrees from normal.

One embodiment of the apparatus 200 includes a conventional laser diode 202, e.g., SLD 104AU available from Sony, Tokyo, Japan, which has been collimated by Hoetron Corp., Sunnyvale, Calif., e.g., a conventional linear polarizer 204, e.g., made of Polarcor that is commercially available from Newport Corp., Irvine, Calif., a conventional liquid crystal variable retarder 206 that is commercially available from Meadowlark, Longmont, Colo., a conventional non-polarizing beam splitter 208 that is commercially available from Newport Corp., Irvine, Calif., a conventional diffuser 210 that is commercially available from Spindler Hoyer, Germany, a conventional feedback photodiode 212 that is commercially available from Hamamatsu Corp., Hamamatsu City, Japan, a feedback amplifier and receiver preamplifier 214 that is commercially available from Analog Design, San Francisco, Calif., a conventional focusing lens 216 that is commercially available from Newport Corporation, Irvine, Calif., a custom integrating sphere 218 that is commercially available from Labsphere, North Sutton, N.H., made from an approximately 0.62 inch cube aluminum block, which has a 0.54 inch diameter spherical section removed from its center, a 4 mm diameter hole at the bottom for the scattered light to enter the sphere, another 4 mm diameter hole at the top for the light to reach a photodetector, two holes at opposite sides for the specular light to enter and exit the sphere, the internal surfaces are coated with a reflective surface that scatter light, e.g. Spectralflect, available from Labsphere, North Sutton, N.H. The integrating sphere 218 has an input hole that is designed to be slightly larger than the laser beam diameter so as not to occlude the beam, the output hole diameter is chosen to be large enough to allow the beam to exit the sphere and small enough to allow for the detection of the minimum spatial frequency according to equation (3), the diameter of the holes and the diameter of the sphere are chosen so that the total surface area of the holes is preferably less than five percent of the total surface area of the sphere, although the use of a larger percentage is possible. The integrating sphere 218 preferably has a baffle extending through its center in the same plane as the incidence light, the baffle has a circular region at its center which is the same diameter as the hole provided for the scattered photodetector. The baffle prevents any first reflection from the disk from reaching the photodetector without first striking the surface of the integrating sphere. The integrating sphere 218 is preferably miniaturized to keep the entire optical device small.

One embodiment of the apparatus 200 also includes a conventional collimating lens 220 that is commercially available from Newport Corporation, Irvine, Calif., a conventional diffuser 222, that is commercially available from Spindler Hoyer, Germany, a conventional specular photodetector 224A and scattered photodetector 224B that is commercially available from Hamamatsu Corp., Hamamatsu City, Japan, a custom baffle 226 that is commercially available from Labsphere, North Sutton, N.H., a liquid crystal variable retarder (LCVR) driver 228, and a conventional computer 240, for example a microcontroller or an IBM personal computer, commercially available from IBM Corporation, Armonk, N.Y., having a conventional input/output device 242, a conventional memory module 244 having unconventional applications stored therein, e.g., the analysis unit 248, and a conventional processor 246, e.g., a Pentium Pro Processor that is commercially available from Intel Corporation, Santa Clara, Calif. It will be apparent to persons skilled in the art that the apparatus 200 is an embodiment of the present invention and that alternate designs can be used without departing from the present invention. The operation of the apparatus 200 is now described in greater detail.

A laser diode 202 emits an electromagnetic signal toward the thin film disk. In an embodiment the electromagnetic signal is a light signal having a wavelength of 780 nanometers (nm) although a wide variety of wavelengths can be used. The angle of propagation of the light signal can be any angle between zero and ninety degrees. However, in an embodiment the angle need not be substantially Brewster's angle for the carbon in the thin film. That is, the angle of propagation differs from the Brewster's angle of the carbon by a minimum of two to five degrees, for example, at which angle the change in the reflectivity of the thin film based upon the carbon changes significantly when compared to the reflectivity at Brewster's angle. The emitted light passes through the linear polarizer 204. The linear polarizer 204 improves the linear polarization of the laser light signal. The polarized light signal passes through a liquid crystal variable retarder (LCVR) 206. The LCVR 206 switches the polarization of the light between P and S linear polarizations in response to an instruction received from the LCVR driver 228. The LCVR driver 228 can be located external to or integral with the computer 240. As described below, P and S linear polarizations enable the apparatus 200 to measure a variety of properties of the thin film 100. A description of one example of the LCVR driver is now described with reference to FIG. 3.

Figure 3:
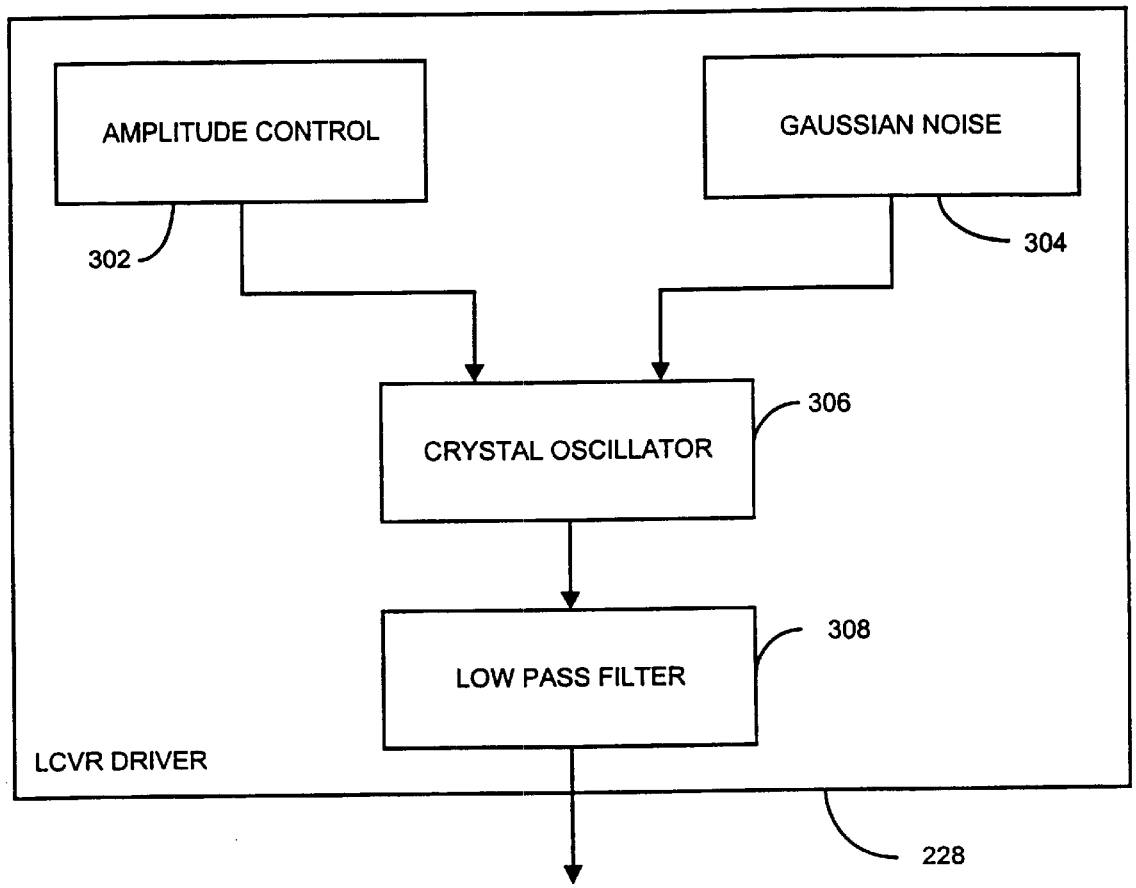
FIG. 3 is a more detailed illustration of a liquid crystal variable retarder (LCVR) driver according to an embodiment of the present invention.

FIG. 3 is a more detailed illustration of the LCVR driver 228 according to an embodiment of the present invention. The LCVR driver 228 includes an amplitude control module 302, a gaussian noise module 304, a crystal oscillator 306, and a low pass filter 308. In an embodiment the crystal oscillator is a 2 kHz square wave oscillator whose fundamental frequency is modulated by five percent in a random manner by Gaussian noise generated by the gaussian noise module 304. The 2 kHz square wave amplitude is controlled in two states by the amplitude control module 302 that receives signals from the computer 240 so that the P and the S polarizations are achievable. The output of the oscillator is low pass filtered by the low pass filter 308 having a cutoff at approximately 15 kHz before being directed to the liquid crystal. The random modulation of the square wave helps prevent crosstalk in the apparatus 200 from being synchronous with the data sampling.

Figure 4:
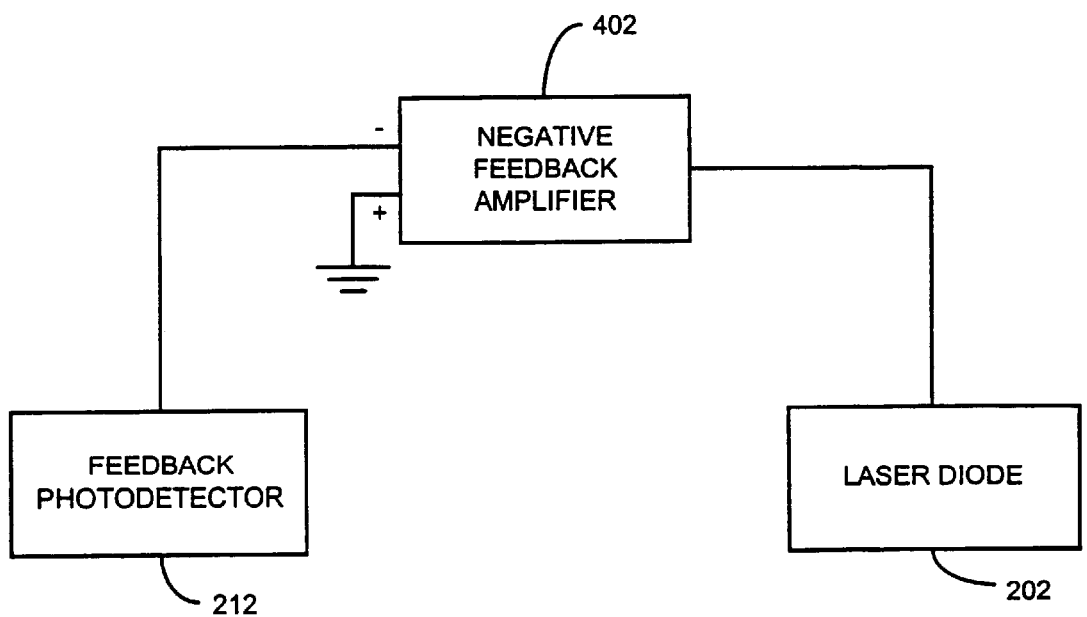
FIG. 4 is an illustration of the feedback amplification system of an embodiment of the present invention.

The linear polarized signal is received by the non-polarizing beam splitter 208 that splits the linear polarized signal. A portion of the linear polarized signal is split and is directed toward a diffuser 210 and to a feedback photodetector 212. The output of the feedback photodetector 212 is received by a feedback amplifier in the feedback amplifier and receiver preamplifier 214. FIG. 4 is an illustration of the feedback amplification system of an embodiment of the present invention. The feedback amplification system of an embodiment includes a negative feedback amplifier 402 that receives the output of the feedback photodetector 212. The negative feedback amplifier 402 outputs a signal to the laser diode that precisely controls the intensity of the laser diode 202. In one embodiment of the present invention the bandwidth of the feedback loop is limited to 15 Hz. This allows stabilization of the laser power between DC and 15 Hz. The bandwidth of the feedback loop is sharply cut off above 15 Hz to prevent power frequencies (60 Hz and its harmonics) from modulating the laser power. An advantage of the external beam splitter 208 together with the reference photodiode 212 is improved temperature stability. The improved temperature stability is achieved since the reference photodiode 212 is identical to the specular 224A and the scattered 224B photodetectors. Any temperature changes in the optical sensitivity of the reference photodiode 212 are substantially compensated by similar changes in the specular 224A and scattered 224B photodetectors.

Laser diodes are well known to have an internal photodiode to monitor the laser output power. Another embodiment of a feedback control circuit to control the optical intensity is to use such a photodiode, which is internal to the laser diode. This laser diode feeds back a control signal to the circuitry described in FIG. 4 and by doing so keeps the intensity of the laser at a constant value.

Conventional systems, for example those described in Meeks, et al., *Optical Surface Analysis of the Head-Disk-Interface of Thin Film Disks,* ASME Transactions on Tribology, Vol. 117, pp. 112–118, (January 1995)) describe the use of narrow band pass filters (NBPF) on the photodetectors in order to minimize interference from external light sources. The NBPF allows only the specified wavelength to reach the detector. One drawback of this method is that it requires the laser to be stable at the specified wavelength. This is difficult as the laser wavelength is affected by temperature change, thus the system has to be thermally stabilized.

To eliminate the effect of external light on the instrument, the entire device 200 is enclosed in a light tight container which eliminates the possibility of external light from reaching the detectors. As a result the NBPF can be eliminated from the design. Removing the NBPF greatly reduces the effect of temperature changes on the signal amplitude. This improves the thermal stability of the system.

Another means to improve the stability of the system is to remove electronic zero drift by use of a black standard. A black standard is a device that absorbs any light coming toward it. One version of a black standard is a cylindrical cavity with a pointed cone inside the cylinder, with all the internal surfaces coated with a black, light absorbing material. This is type of black standard is commercially available from Labsphere, North Sutton, N.H. The electronics typically drift over time due to thermal changes, component age, and other factors. The black standard provides a stable zero level reference to measure and cancel the drift. Prior to each scan the laser beam is directed into the black standard, the electronics signals are then measured and the zero level is defined. This results in improved stability in the long-term drift of the zero levels of the system.

The linearly polarized signal that passes through the non-polarizing beam splitter 208 is directed toward a focusing lens 216 that focuses the light signal onto an area of the thin film 100 that is located beneath the integrating sphere 218 (a cross-sectional view of the integrating sphere is illustrated in FIG. 2). A first portion of the focused light signal reflects off the thin film 100 toward a collimating lens 220 and a second portion scatters within the integrating sphere 218. A more detailed discussion of the reflecting and scattering of the focused light signal is now set forth.

Figure 5A:
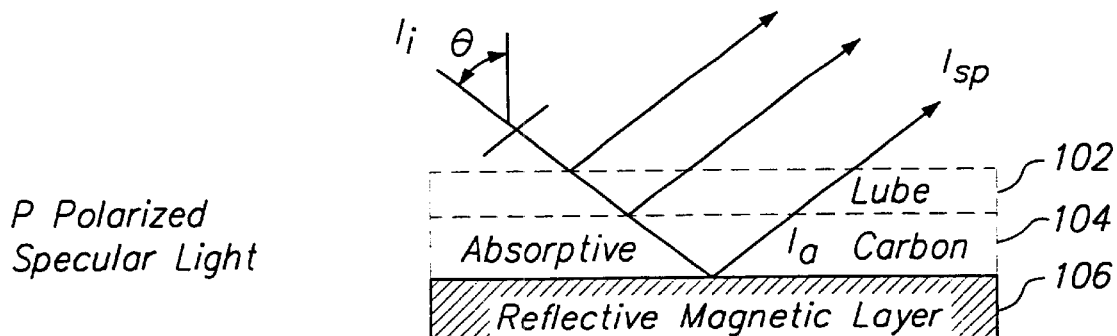
FIGS. 5($a$)–($c$) are illustrations of the reflective and scattering properties of P and S polarized radiation according to an embodiment of the present invention.
Figure 5B:
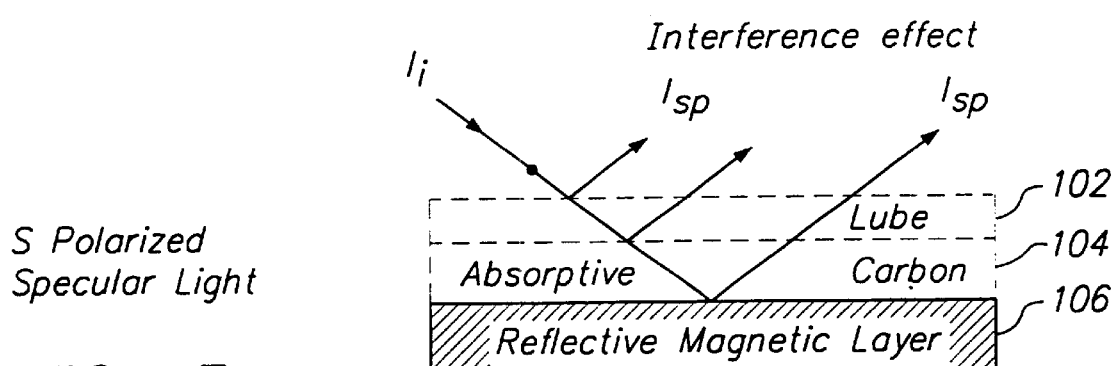
Figure 5C:
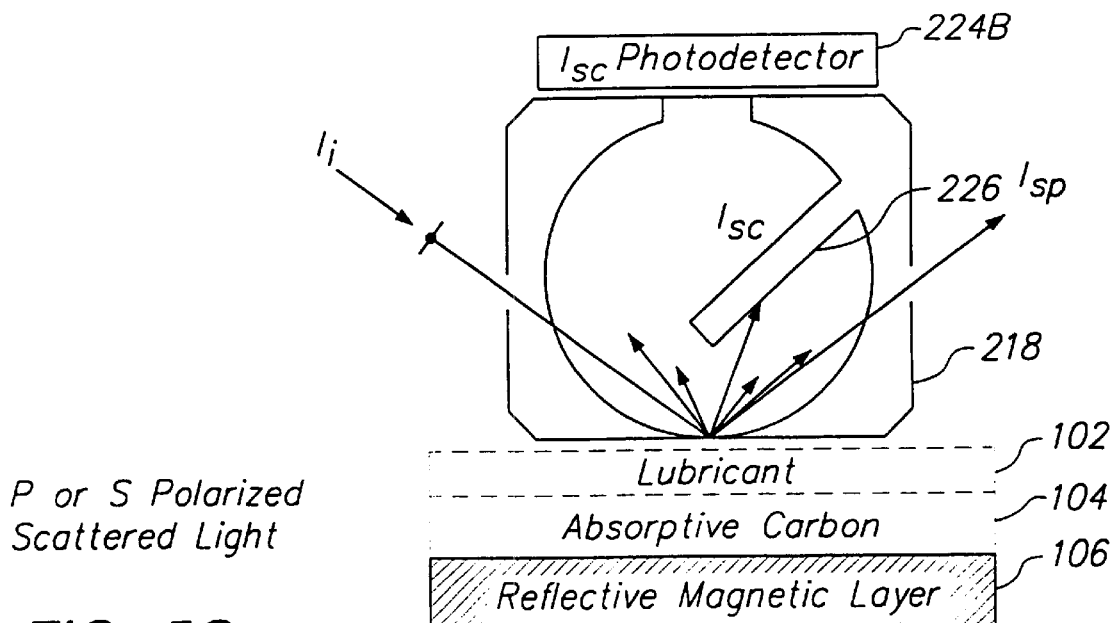

FIGS. 5(a)–(c) are illustrations of the reflective and scattering properties of P and S polarized radiation according to an embodiment of the present invention. The view of FIGS. 5(a)–(c) are from a reverse-angle view in comparison to the view of FIG. 2. FIG. 5(a) illustrates the reflection of the focused light signal (P polarized light) off the thin film 100. As described above, the focused P polarized light signal is directed toward the thin film 100 at an angle, e.g., an angle that is not substantially Brewster's angle. Some of the focused P polarized light signal reflects off the lubricant layer 102. Some of the focused P polarized light signal reflects off the carbon layer 104 while some of the focused P polarized light is absorbed by the carbon layer, and some of the P polarized light reflects off the magnetic layer 106. FIG. 5(b) illustrates the reflection of the focused light signal (S polarized light) off the thin film 100. As described above, the focused S polarized light signal is also directed toward the thin film 100 at an angle that is not substantially Brewster's angle. The reflection of the S polarized light is similar to the reflection of the P polarized light described above. Specifically, some of the focused S polarized light signal reflects off the lubricant layer 102. Some of the focused S polarized light signals reflect off the carbon layer 104 while some of the focused S polarized light is absorbed by the carbon layer, and some of the S polarized light reflects off the magnetic layer 106.

The reflected (specular) light signals $I_{sp}$ pass through an opening in the integrating sphere 218 toward an optional collimating lens 220. The collimating lens collimates the reflected light signals which enables the diffuser 222 and specular photodetector 224A to be positioned at a further distance from the reflection area on the thin film disk 100 than would otherwise be possible. The diffuser spreads the beam in a manner such that the position sensitivity of the specular photodetector is reduced. This reduces the sensitivity of the photodetector to motion of the optical beam induced by wobble of the disk. The diffuser 222 and the specular photodetector 224A are positioned at an angle that is slightly off the normal (e.g., five degrees) of the reflected light path. This geometry reduces the amount of light signals that are reflected off of the diffuser 222 and/or the specular photodetector 224A and propagate back into the integrating sphere which can possibly affect the detection of scattered light, as described below. That is, the addition of the collimating lens 220 which collimates the light allows the path length to be increased so that the amount of tilt of the specular photodetector 224A and the diffuser 222 is minimized. When the amount of tilt of the specular photodetector 224A and diffuser 222 is reduced, the specular photodetector will receive a greater portion of the reflected signal since the amount of the specular signal lost due to a reflection off the diffuser 222 or the specular photodetector 224A is minimal. In an embodiment, the collimating lens 220 is used for a high resolution (short focal length) design. A lower resolution system (longer focal length lens) generally allows sufficient length between the specular photodiode and the integrating sphere to require only a small tilt of the specular photodiode. The specular signal must not be allowed to return to the integrating sphere since this corrupts the scattered signal and causes a crosstalk between the scattered and specular signals. The diameter of the light port in the optic main body is kept to a minimum to block most of the light that is reflected by any surface in the specular detector area toward the integrating sphere. The port diameters are made just slightly larger than the beam diameter itself. They can be stepped (not continuously tapered) to make it easier to fabricate. The specular photodetector 224A outputs a signal representing the amount of light received to the receiver preamplifiers in the feedback amplifier and receiver preamplifiers board 214. The received light is interpreted using the computer 240 in the manner described below. The operation of the specular photodetector 224A is described in greater detail below.

FIG. 5(c) illustrates the scattering effect of the S or P polarized light signals. When the focused light signal strikes the lubricant layer 102, the carbon layer 104, and/or the magnetic layer 106, a portion of the light will scatter at angles that are not equal to the angle of incidence. For simplicity, FIG. 5(c) only illustrates reflection off the lubricant layer 102. The scattered component of the light is measured by the scattered photodetector 224B attached to the integrating sphere 218. Internal to the integrating sphere 218 is a baffle 226 which does not permit any first reflection scattered light to reach the scattered photodetector 224B. This baffle 218 reduces the measurement of hot spots caused by a direct reflection from the disk into the scattered photodetector 224B. The baffle 218 prevents this by forcing any reflections from the thin film disk 100 to take two or more reflections before reaching the scattered photodetector 224B.

As described above, the LCVR 206 allows the polarization to be switched between P and S linear polarizations. The P specular light signal primarily gives information regarding changes in the thickness, or the absolute thickness of the carbon layer on the thin film disk. The S specular light signal primarily gives information regarding changes in the lubricant thickness which has been applied to the carbon surface. The scattered light, together with the specular light gives a measurement of the roughness of the thin film disk surface. The method for using the specular and scattered components of the P and S polarized light to measure thin film 100 characteristics is described below.

Figure 6:
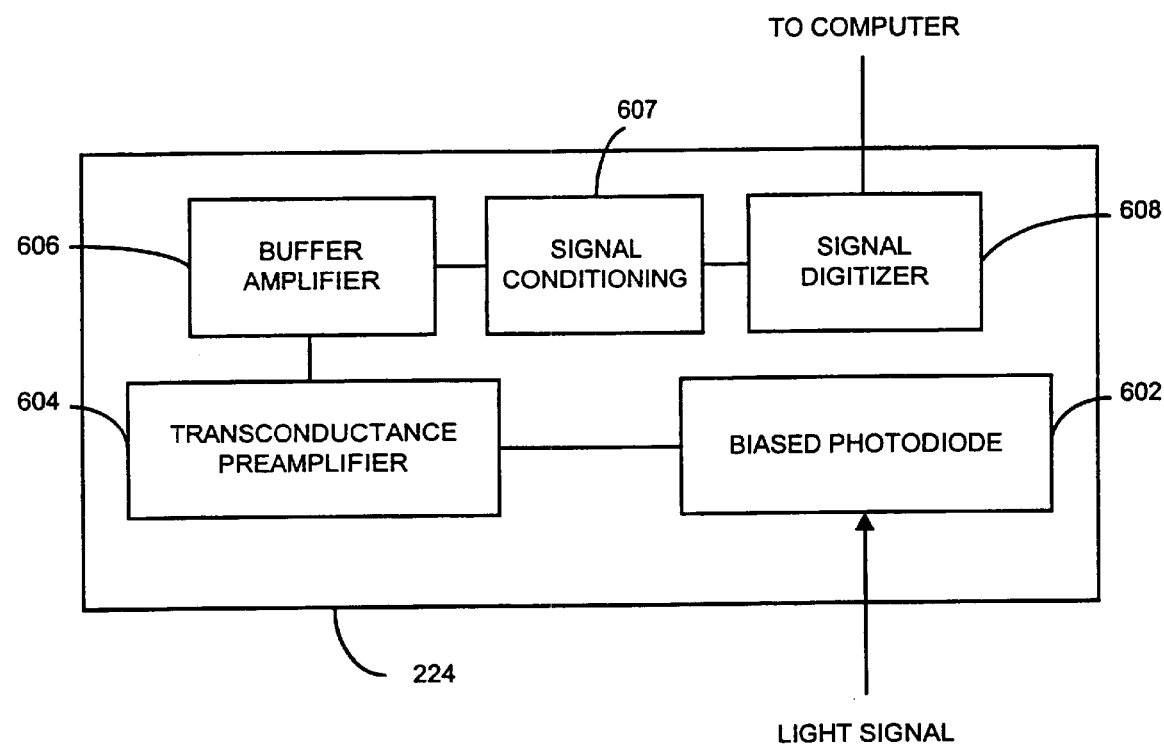
FIG. 6 is a more detailed illustration of photodiode electronics according to an embodiment of the present invention.

FIG. 6 is a more detailed illustration of a photodetector 224 according to an embodiment of the present invention. The photodetector can be the specular photodetector 224A or the scattered photodetector 224B. The photodetector 224 of an embodiment includes a biased photodiode 602, a transconductance preamplifier 604, a buffer amplifier 606, signal conditioning circuitry 607 (available from Analog Design, Inc. in Topanga, Calif.) and a GAGE Applied Sciences, Inc. analog to digital board 608, e.g., model number CS1012/PCI that is commercially available from GAGE Applied Science, Inc., Montreal, Canada. The biased photoconductor 602 receives a light signal and generates a signal reflecting the intensity of the received light. The biased photodiode signal is amplified by the transconductance preamplifier 604 which is transmitted to the buffer amplifier 606. Before being digitized by the analog to digital board the signal passes through signal conditioning electronics 607. The signal conditioning electronics 607 subtracts the DC offset of the signal, passes the signal through a variable anti-aliasing filter and provides up to 64 times multiplication of the encoder signal from the spindle which rotates the thin film disk 100, in an embodiment. The multiplied encoder signal and the index from the spindle are used as the clock and trigger, respectively for the analog to digital board. After the specular and scattered signals have been conditioned they are passed to the analog to digital board 608 where they are digitized. The digitized signal is transmitted to the computer 240 for analysis. The method for analyzing the received signals to determine properties of the thin film disk 100 is set forth below.

The properties of the entire thin film disk 100 can be measured by focusing the light signal on all areas of the thin film disk 100. This can be accomplished by precisely moving the thin film disk 100 or by moving the apparatus 200. In an embodiment the apparatus 200 is attached to a very accurate stepper motor (not shown) and the apparatus 200 is stepped over the surface of the thin film disk 100. One example of such a stepper motor is Newport's Mikroprecision stage that is commercially available from Newport, Irvine, Calif.

Figure 7:
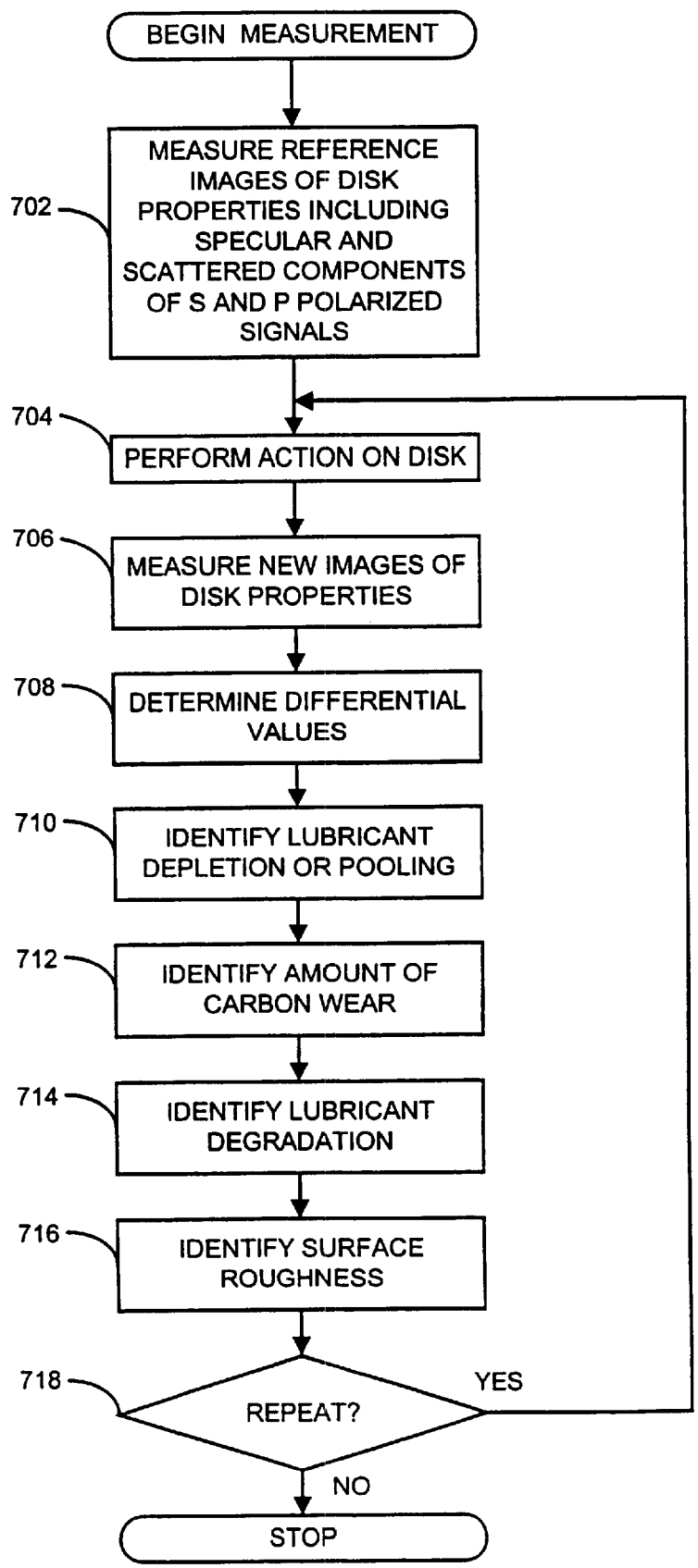
FIG. 7 is a flow chart illustrating a method for measuring in situ thin film properties according to an embodiment of the present invention.

FIG. 7 is a flow chart illustrating a method for measuring thin film properties according to an embodiment of the present invention. In an embodiment a differential technique is used such that reference images of the thin film disk are made at the beginning of the experiment and the reference images are subtracted from each of the subsequent images. The resulting differential images show only what has changed as a result of interacting with the disk during the period of time between the reference and subsequent images. The reference images are not a requirement to analyze the data but it makes any changes in the disk surface easier to identify and increases the sensitivity to changes. However, in alternate embodiments only a single set (Ssp, Ssc, Psp, and Psc) of images is measured (at a angle that is not substantially Brewster's angle for the carbon layer 104, for example) and lubricant thickness and degradation, carbon wear and surface roughness is determined.

The apparatus 200 measures 702 reference values of the thin film disk at an angle that is not substantially Brewster's angle (as described above). These reference values include the specular and scattered components of the P and S polarized signals received by the specular photodetector 224A and the scattered photodetector 224B, respectively.

The measurements can be taken in situ or ex situ, as described below. The user then performs 704 an action on the thin film disk 100. For example, the thin film disk 100 is subjected to repeated start-stop actions such that a ceramic slider of the read/write head repeatedly contacts the thin film disk 100. This simulates repeated power on/off cycles of a hard disk drive, for example. This contact can cause lubricant depletion, lubricant degradation, and carbon layer wear. After the first iteration of action is performed on the thin film disk 100, e.g. a thousand start/stop simulations, the apparatus measures 706 new values of the thin film disk 100. These new values include the specular and scattered components of the P and S polarized signals received by the specular photodetector 224A and the scattered photodetector 224B, respectively. The signals representing these values are stored in the computer memory module 244 and an analysis unit 248 in the memory module analyzes the values in conjunction with the processor 246. The functions performed by the analysis unit 248 are described below.

The analysis unit 248 determines 708 differential values by determining the difference in values between each reference value and the corresponding value in the subsequent measurement of the thin film disk 100. The differential values include the difference (delta) in the specular component of the S polarized light ($\Delta S_{SP}$), i.e., the reflectance received by the specular photodetector 224A when S polarized light is transmitted toward the thin film disk, the delta in the specular component of the P polarized light ($\Delta P_{SP}$), the delta in the scattered component of the S polarized light ($\Delta S_{SC}$), and the delta in the scattered component of the P polarized light ($\Delta P_{SC}$). These differential values are used to identify thin film properties as described below. One technique for measuring the reflectance of a laser signal striking the thin film disk 100 at Brewster's angle of the carbon layer 104 is described in the S. Meeks et. al., *Optical Surface Analysis of the Head-Disk-Interface of Thin Film Disks*, ASME Transactions on Tribology, Vol. 117, pp. 112–118, (January 1995), that was incorporated by reference above.

The subtraction of the reference and subsequent images is degraded by the presence of thermal drift during the time between the gathering of the reference and subsequent images. This thermal drift is caused by the thermal expansion of the disk and other components with variations in environmental temperature. The thermal drift can be corrected by shifting each image with respect to the other in the radial direction of the thin film disk. The shifted images are shifted and the cross correlation between the two images is computed. The amount of shift is increased and the cross correlation is repeated until a maximum is reached. The shift at which the maximum in the cross correlation occurs is the optimal shift, i.e., the one which corrects for the thermal drift of the components. An alternative to using the cross correlation is to subtract the images and compute the variance or standard deviation between the two images. The shift is then increased and the variance or standard deviation is again computed. The amount of shift which minimizes the standard deviation or variance is the optimal shift which will correct for the thermal drift.

In order to better understand the method for analyzing the differential values, a description of the effect of the thickness of the lubricant layer and the thickness of the carbon layer 104 on the amount of light received by the specular photodetector 224A and the scattered photodetector 224B is now set forth.

Figure 8:
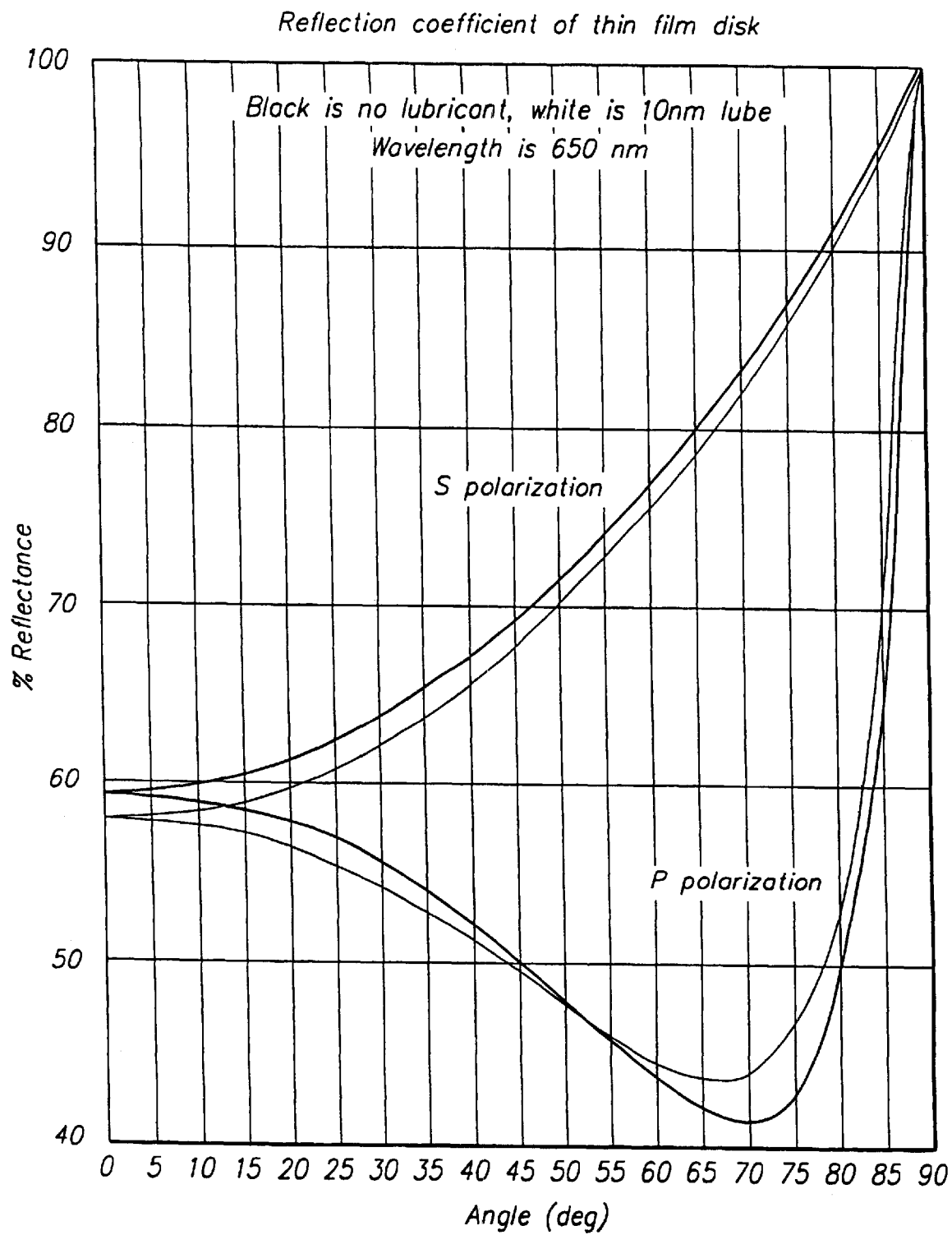
FIG. 8 is a graph illustrating the reflectance of P and S polarized radiation versus angle of incidence off a thin film having no lubricant and having ten nanometers of lubricant according to an embodiment of the present invention.

FIG. 8 is a graph illustrating the reflectance of P and S polarized radiation off a thin film having no lubricant layer 102 and having a lubricant layer 102 whose depth is ten nanometers according to an embodiment of the present invention. FIG. 8 shows the simulated specular reflectivity of the S and P polarized light versus the angle of incidence of the light signal on the thin film disk. In this example the light signal has a wavelength of 650 nm. Two curves are shown, one with no lubricant applied (black) to the carbon surface and the other with ten nm of lubricant (white) applied. An unrealistically thick layer of lubricant has been shown in this figure to illustrate the differences between the curves. The difference between the two curves represents the P and S polarized specular light sensitivity to lubricant. At angles between zero degrees and approximately 53 degrees the reflectivity of the disk decreases when lubricant is added to the disk for both the P and S polarized light signals. At angles above approximately 53 degrees the reflectivity of the disk decreases for S polarized light and increases for P polarized light, when lubricant is added to the carbon surface. At approximately 53 degrees, the P polarized light is insensitive to lubricant on the surface, because this is the Brewster's angle of the lubricant. At angles near 80 degrees the P polarized light reaches a maximum in its sensitivity to lubricant—approximately 2 or 3 times the sensitivity of the S polarized light. The angle of 53 degrees is a specific example of the Brewster's angle of the lubricant which is defined as the Arc Tan of [index of refraction of lubricant/index of refraction of air].

The ratio between the P sensitivity to lubricant and the S sensitivity changes as a function of the angle as can be seen in FIG. 8. At a fixed angle of incidence this ratio is related to the index of refraction of the lubricant. Therefore, if the lubricant degrades, the index of refraction also changes and the ratio of the change in the specular component of the S polarized light ($\Delta S_{SP}$) to the change in the specular component of the P polarized light ($\Delta P_{SP}$) will change. This is one technique for measuring the degradation of the lubricant on a thin film disk 100. The angle of 53 degrees is particularly good for this since even a very small change in the lubricant index will generate a large change in the ratio of delta S ($\Delta S_{SP}$) to delta P ($\Delta P_{SP}$).

Figure 9:
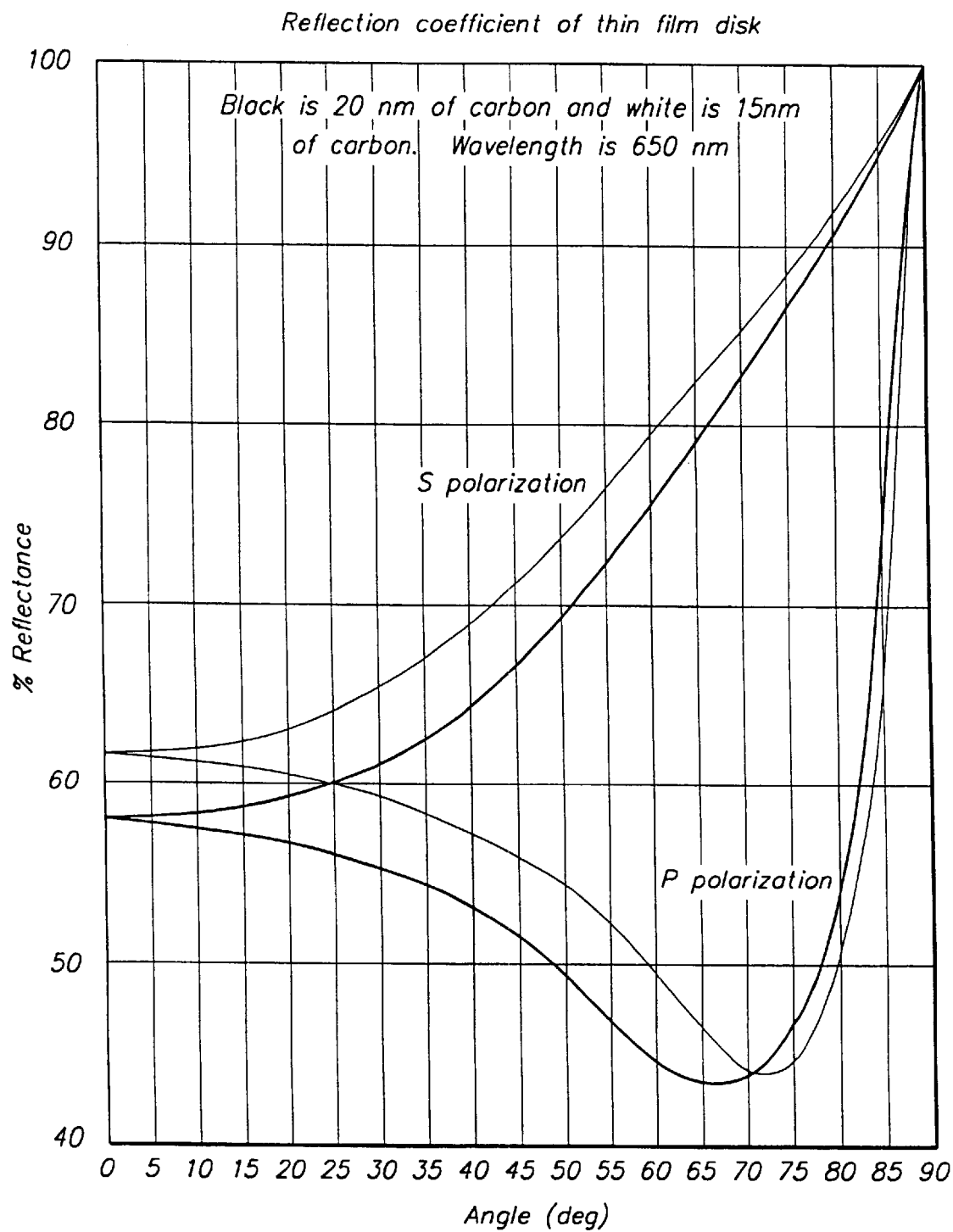
FIG. 9 is a graph illustrating the reflectance of P and S polarized radiation versus angle of incidence off a thin film having twenty nanometers of carbon and having fifteen nanometers of carbon according to an embodiment of the present invention.

FIG. 9 is a graph illustrating the reflectance of P and S polarized radiation off a thin film having a carbon layer 104 of twenty nanometers and having a carbon layer of fifteen nanometers according to an embodiment of the present invention. The black curve shows the S and P reflectivity versus angle of incidence with 20 nm of carbon present. The white curve shows the same curves when 5 nm of carbon has been removed. Both the S and P polarization's can be used to measure carbon wear, but in general P is more sensitive and more linear in its response to wear of the carbon. The S reflectivity increases when carbon is removed at all angles of incidence. The P polarized light increases for carbon removal for angles less than approximately 71 degrees, is zero at approximately 71 degrees and decreases when the angle is greater than 71 degrees. The maximum sensitivity to carbon thickness or carbon wear occurs near zero degrees. The angle of 71 degrees is a specific example of the "P polarization crosspoint angle" which is defined as the angle at which the P polarized beam reflection coefficient is insensitive to the carbon thickness change.

In an embodiment the angle of incidence is 58 degrees to measure all lubricant features, carbon thickness and wear and surface roughness. However, as described above, many angles can be used. Operation at 58 degrees allows the user to easily separate lubricant thickness increase (P reflectivity increase, S decrease, see FIG. 8) from carbon wear (S and P reflectivity increase). This technique for measuring carbon wear is not limited to carbon overcoats. The wear of any absorbing layer can be measured by the embodiments discussed here. In particular, overcoats such as Zirconium Oxide, Silicon Dioxide, organic materials and plastics, for example, can be used. If these alternative overcoats have lubricant on them, then the lubricant thickness, depletion and degradation may be measured as well.

One technique for identifying the lubricant thickness change from carbon wear based upon $\Delta S_{SP}$ and $\Delta P_{SP}$ is to use a two-dimensional concentration histogram. A technique for generating and using a two-dimensional concentration histogram is described by S. Meeks et. al., *Optical Surface Analysis of the Head-Disk-Interface of Thin Film Disks,* ASME Transactions on Tribology, Vol. 117, pp. 112–118, (January 1995), that was incorporated by reference above. To construct a two dimensional histogram small regions (known as buckets) are defined in the P, S plane (the space of the histogram) which have a certain $\Delta P$ by $\Delta S$ dimension. Each coordinate pair (x,y) in the real space image is selected and its corresponding bucket into which its P, S coordinate falls is identified. After going through the entire image the total number of points in each bucket is identified and a color, for example, is assigned based upon the number of points in the bucket. The completed two dimensional image is known as a two-dimensional concentration histogram. The two-dimensional concentration histogram separates the regions of lubricant pooling, depletion, carbon wear and debris into separate regions. Debris are products generated as a result of the wear process on the disk. In addition, the slope of the histogram is related to the index of refraction of the layer being altered. As described below, the slope of the histogram can be used to differentiate between lubricant depletion and carbon depletion. Some examples of histograms which each corresponds to a different embodiment of the present invention are set forth in FIGS. 10–13.

Figure 10:
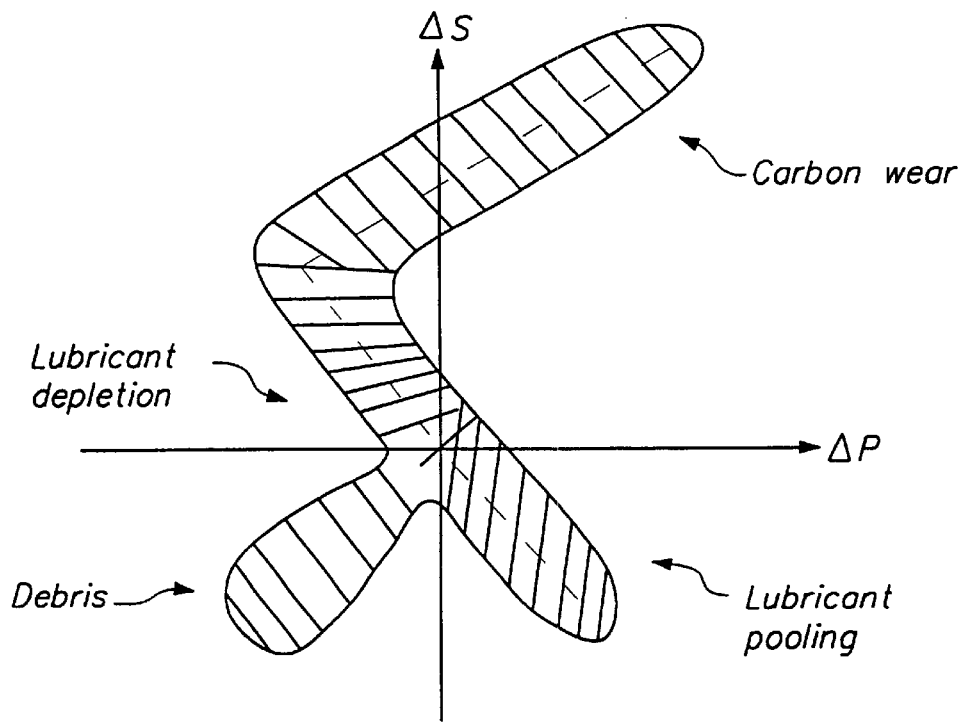
FIG. 10 is a two dimensional concentration histogram illustrating the relationship between changes in S polarized radiation and P polarized radiation with respect to thin film measurements when an angle of incidence of the radiation source is between 53 degrees and 71 degrees according to one embodiment of the present invention.

FIG. 10 is a histogram illustrating the relationship between changes in S polarized radiation ($\Delta S_{SP}$) and P polarized radiation ($\Delta P_{SP}$) with respect to thin film measurements when an angle of incidence of the radiation source is between approximately 53 degrees and approximately 71 degrees according to an embodiment of the present invention. The angle of 53 degrees is a specific example of the Brewster's angle of the lubricant which is defined as the Arc Tan of (index of refraction of lubricant/index of refraction of air). The angle of 71 degrees is a specific example of the "P polarization crosspoint angle" which is defined as the angle at which the P polarized beam reflection coefficient is insensitive to the carbon thickness change.

In an embodiment, the analysis unit 248 identifies 710 lubricant pooling or depletion or identifies 712 carbon wear using the differential specular values ($\Delta S_{SP}$, $\Delta P_{SP}$) in the following manner. When the angle of incidence that the focused light signal strikes the thin film is between approximately 53 degrees and 71 degrees, if the value of $\Delta S_{SP}$ is positive and the value of $\Delta P_{SP}$ is negative then the analysis unit 248 determines that thin film disk 100 has experienced lubricant depletion. Using the histogram illustrated in FIG. 10 this is determined by locating the quadrant in which the $\Delta S_{SP}$, $\Delta P_{SP}$ data is located, in this example, the data is located in quadrant II which is identified as lubricant depletion. The analysis unit 248 determines the amount of lubricant depletion or pooling based upon the value of $\Delta S_{SP}$ and a calibration of the amount of $\Delta S_{SP}$ change per angstrom of lubricant change.

This range of angle of incidence allows easy distinction in the measurements of lubricant pooling/depletion, carbon wear, and debris. The lubricant pooling, depletion, carbon wear, and debris will be in different quadrants of the two dimensional histogram, making it easier to separate the data. This data from each of the four quadrants can be traced back to the original images (P and S images in real space) indicating the locations on the disk of lubricant pooling, depletion, carbon wear, and debris.

If both $\Delta S_{SP}$ and $\Delta P_{SP}$ are positive then the analysis unit 248 determines that the thin film disk 100 experienced carbon wear. The analysis unit can determine the amount of carbon wear using a variety of techniques. Some of these techniques are described below. If $\Delta S_{SP}$ is negative and $\Delta P_{SP}$ is positive then the analysis unit 248 determines that the thin film disk 100 experienced lubricant pooling. As described above, the ratio of $\Delta S_{SP}/\Delta P_{SP}$ correlates to the index of refraction of the lubricant. The expected value of this ratio is known and is stored in the computer memory module 244. If the analysis unit 248 determines that the ratio of $\Delta S_{SP}/\Delta P_{SP}$ does not correspond to the expected value of this ratio, the analysis unit determines 714 that lubricant of the lubricant layer degraded.

Figure 11:
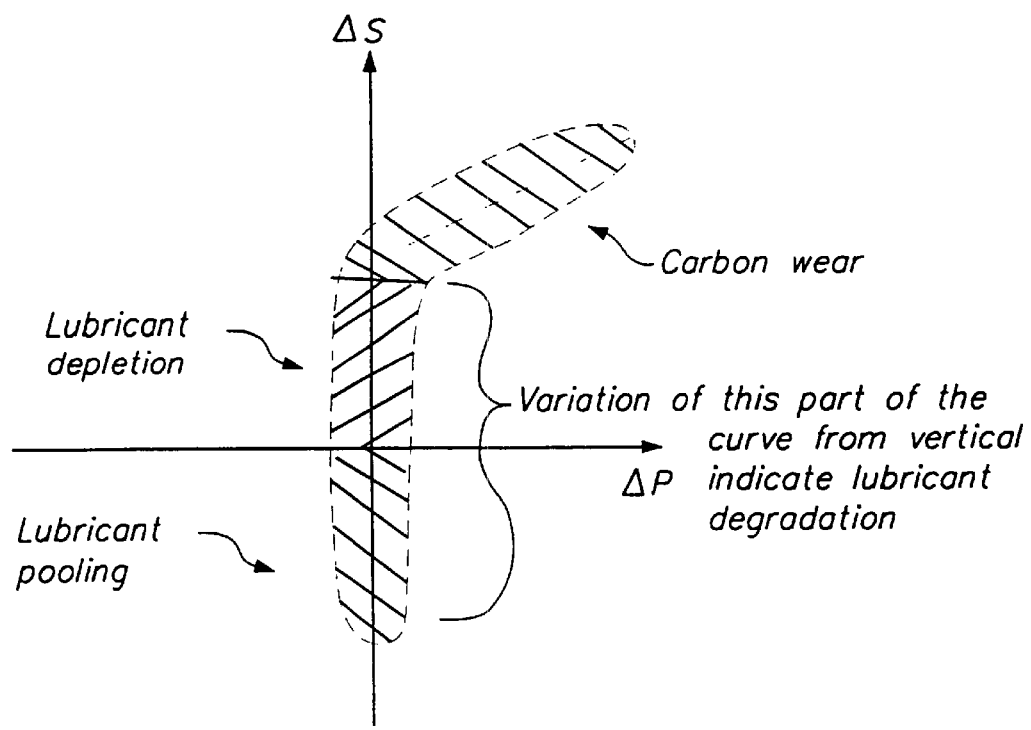
FIG. 11 is a two dimensional concentration histogram illustrating the relationship between changes in S polarized radiation and P polarized radiation with respect to thin film measurements when an angle of incidence of the radiation source is approximately 53 degrees according to one embodiment of the present invention.

FIG. 11 is a histogram illustrating the relationship between changes in S polarized radiation ($\Delta S_{SP}$) and P polarized radiation ($\Delta P_{SP}$) with respect to thin film measurements when an angle of incidence of the radiation source is approximately 53 degrees (in general, Brewster's angle of the lubricant) according to one embodiment of the present invention. This angle of incidence enhances sensitivity to changes in the lubricant index of refraction. This is an embodiment which is optimized for measuring lubricant degradation. A change in the lubricant index of refraction is related to the degradation of the lubricant.

Figure 12:
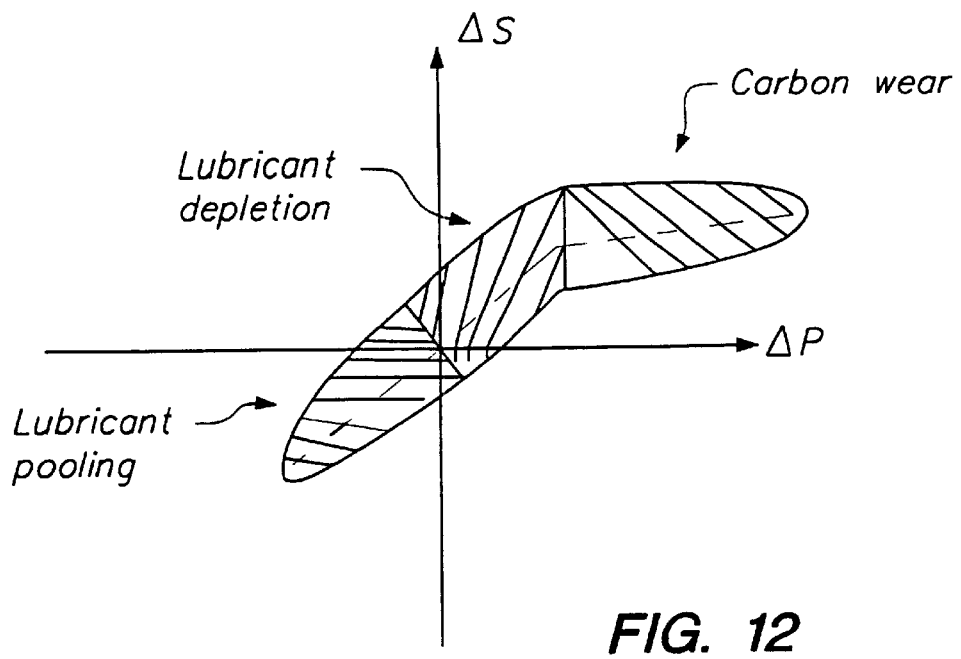
FIG. 12 is a two dimensional concentration histogram illustrating the relationship between changes in S polarized radiation and P polarized radiation with respect to thin film measurements when an angle of incidence of the radiation source is less than 53 degrees according to one embodiment of the present invention.

FIG. 12 is a histogram illustrating the relationship between changes in S polarized radiation ($\Delta S_{SP}$) and P polarized radiation ($\Delta P_{SP}$) with respect to thin film measurements when an angle of incidence of the radiation source is less than 53 degrees according to one embodiment of the present invention. This range of angle of incidence enhances sensitivity to lubricant, carbon thickness change and absolute carbon thickness. This embodiment is optimized for measuring lubricant pooling/depletion, carbon wear and carbon thickness.

Figure 13:
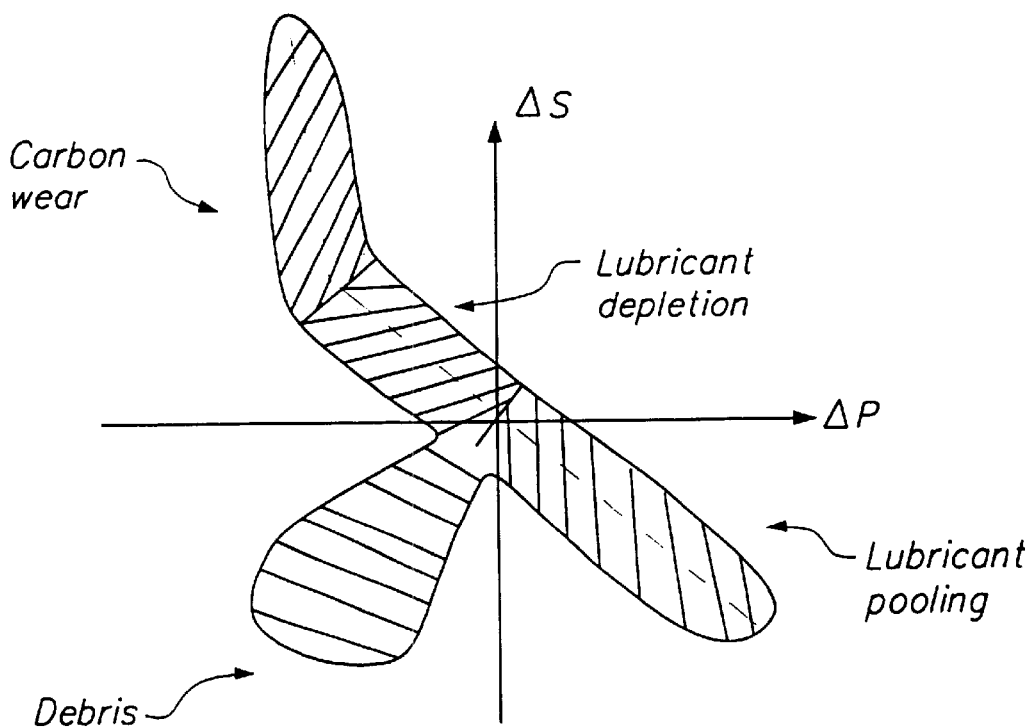
FIG. 13 is a two dimensional concentration histogram illustrating the relationship between changes in S polarized radiation and P polarized radiation with respect to thin film measurements when an angle of incidence of the radiation source is between 71 degrees and 90 degrees according to one embodiment of the present invention.

FIG. 13 is a histogram illustrating the relationship between changes in S polarized radiation ($\Delta S_{SP}$) and P polarized radiation ($\Delta P_{SP}$) with respect to thin film measurements when an angle of incidence of the radiation source is between 71 degrees and 90 degrees according to an embodiment of the present invention. This range of angle of incidence has the highest sensitivity to lubricant thickness change, specifically the P-polarized light. This embodiment is optimized for measuring lubricant pooling/depletion. When in this range of angles, the spatial frequency of the measured surface roughness is nearly twice as large as when measured at near normal incidence. This allows the measurement of high spatial frequency roughness (microroughness).

The technique used for analyzing these histograms is similar to the description set forth above. With respect to FIG. 12, since the values of $\Delta S_{SP}$ and $\Delta P_{SP}$ are both positive for lubricant depletion and carbon wear, one technique for identifying which occurs is to determine the point at which the slope of the histogram changes, as illustrated in FIG. 12. The $\Delta P_{SP}$, $\Delta S_{SP}$ histograms are constructed by subtracting the reference images (taken before any testing has begun) from data gathered during the testing procedure (start/stops, thin film head flying or dragging). The differential images are constructed as described earlier and the analysis described above is applied to the histograms. A time sequence of histograms can be constructed by subtracting images at various time points from the reference images. In this manner the evolution of the histograms and hence the disk surface can be followed and analyzed.

The analysis unit 248 identifies 716 the surface roughness of the thin film disk 100. The roughness is measured simultaneously with the measurement of the specular light and the scattered light. The analysis unit 248 uses the equation (1) to determine the RMS (root means square) roughness of the thin film disk 100.

$$\text{RMS roughness} = R_Q = \frac{[(TIS)^{1/2} * \lambda]}{4 * \pi * \cos(\varphi)} \quad (1)$$

Where $\lambda$ is the wavelength of the light signal, $\phi$ is the angle of incidence of the light signal, and TIS is the total integrated scattered portion of the light signal and is defined by equation (2).

$$TIS = \frac{SC}{SP + SC} \quad (2)$$

Where SC is the total scattered light and SP is the total specular light. As indicated above, the wavelength in the above equation is the wavelength of the incident light. In an embodiment the wavelength is either 780 nm or 650 nm, but in alternate embodiments the wavelength can be any visible or invisible light wavelength. The maximum spatial frequency over which the roughness is measured is determined by the wavelength of light and the angle of incidence according to equation (3), for example.

$$f_g = (\sin(\phi_1) - \sin(\phi_i))/\lambda \quad (3)$$

Where $f_g$ is the maximum spatial frequency, $\phi_1$ is the maximum scattering angle and $\phi_1$ is the angle of incidence. The minimum spatial frequency is determined by the spot size or the exiting hole of the sphere, whichever yields a higher number.

Figure 18:
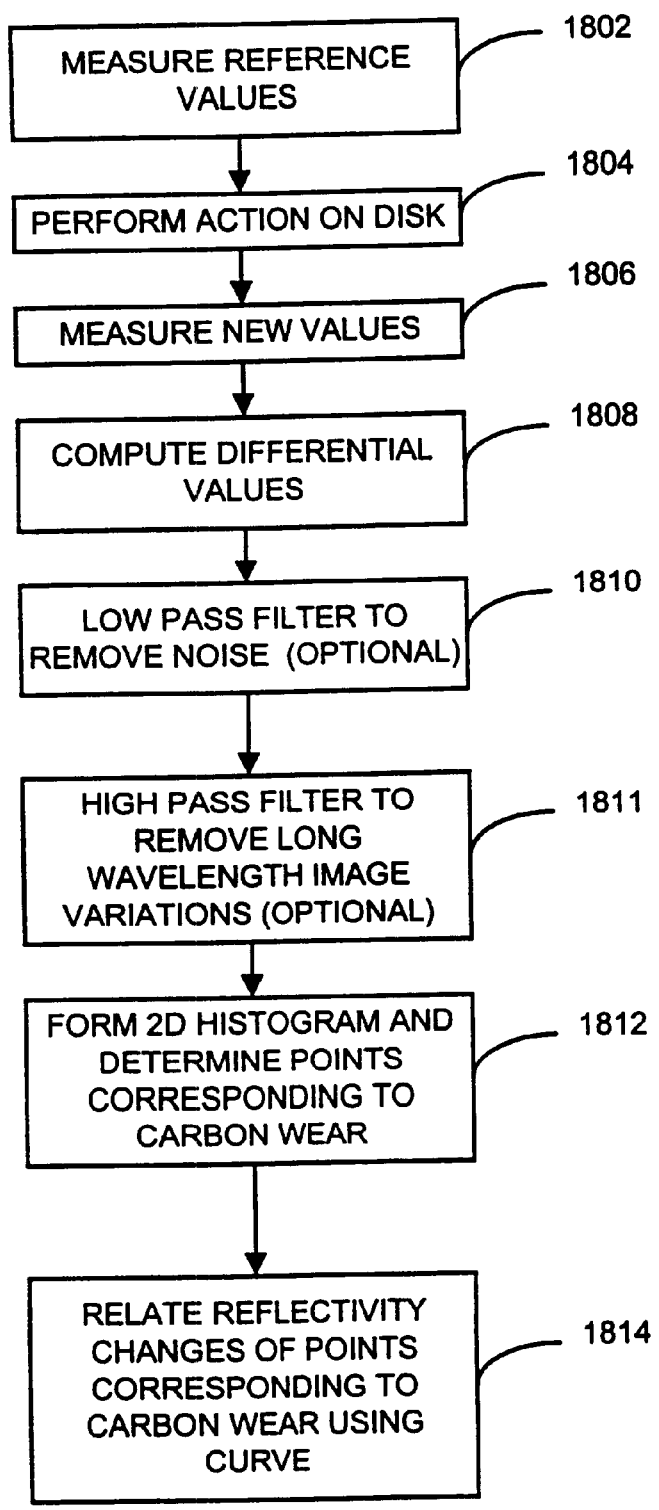
FIG. 18 is a flow chart illustrating a method for measuring carbon wear for an in situ process according to an embodiment of the present invention.

The measurement of the scattered light is used to measure the amount of carbon wear and the carbon thickness. The incident intensity is given in equation (4). Equation (4) is simply a statement of the conservation of energy.

$$I_i = I_A + (I_{SP} + I_{SC}) \quad (4)$$

Where $I_i$ is the incident intensity and $I_A$ is the absorbed intensity, which is related to the wear of the carbon film and the thickness of the carbon, $I_{SP}$ is the specularly reflected intensity and $I_{SC}$ is the scattered intensity. The incident intensity is kept fixed and in order to measure the absorbed intensity and hence the carbon wear or carbon thickness it is necessary to measure both the specular and scattered light at the given angle of incidence. The algorithm for measuring carbon wear can be separated into two cases. The first case is known as an in situ wear measurement described above. FIG. 18 shows the flow chart for determining carbon wear for the in situ case. The process includes placing a disk within a test stand and taking 1802 reference images at the very beginning of the experiment. The reference images are the $S_{SP}$, $S_{SC}$ and $P_{SP}$, and $P_{SC}$ images before anything has been done to the surface of the disk. The disk is then subjected 1804 to start/stop actions of a thin film magnetic head or any other process which might cause wear of the carbon protective overcoat. Intermediate to the start/stops, the disk is scanned 1806 numerous times to follow the wear process. At the completion of the experiment the differential images are constructed 1808 by subtracting the reference images from the images taken before the start/stop actions upon the disk. The two dimensional concentration histograms are constructed by summing $\Delta P_{SP}$ and $\Delta P_{SC}$ (the difference images formed by subtracting the reference image from the intermediate image) and making the two-dimensional concentration histogram with the corresponding $\Delta S_{SP}$ summed with $\Delta S_{SC}$. The images can be low pass filtered 1810 and high pass filtered 1811, if necessary and the two dimensional histograms are constructed 1812. The histograms may appear as shown in FIG. 10 and if so the region, which lies in the first quadrant, corresponds to carbon wear.

Figure 1:
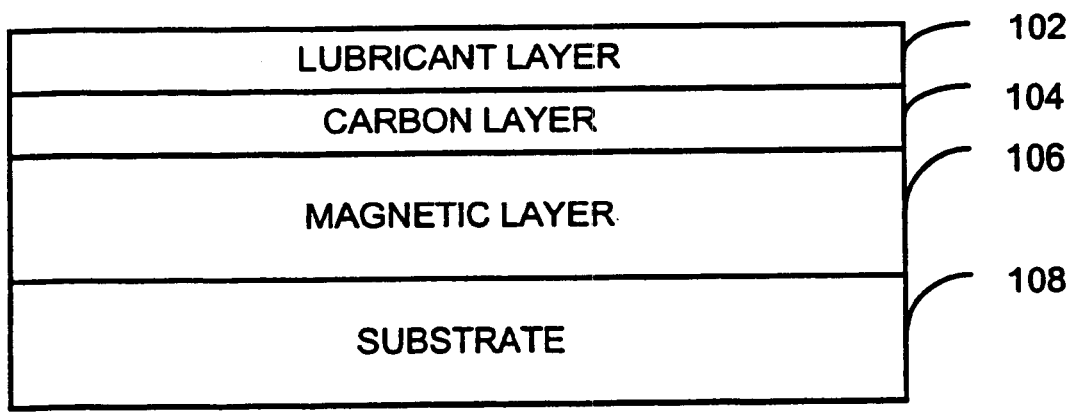
FIG. 1 is an illustration of a thin film that can be measured using an embodiment of the present invention.
Figure 14:
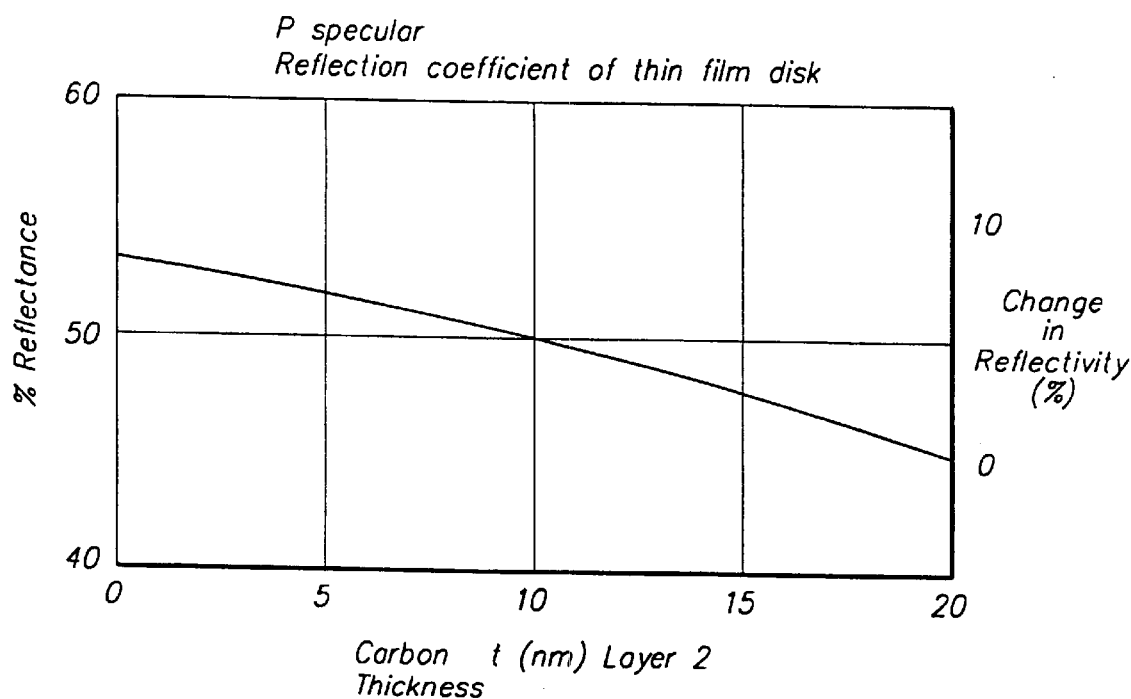
FIG. 14 is a theoretical graph illustrating the change in P specular reflectivity verses the thickness of a carbon layer in nanometers (nm).

The carbon wear can be calibrated 1814 by a curve of P specular light versus carbon wear such as that shown in FIG. 14. FIG. 14 is a theoretical graph illustrating the change in P reflectivity and the absolute P reflectivity verses the thickness of a carbon layer in nm. The theoretical curve shown in FIG. 14 has been computed from knowledge of the complex indices of refraction of the layers of the thin film disk shown in FIG. 1 using a thin film analysis program called "Film Star" that is commercially available from FTG Software Associates, Princeton, N.J. Alternate ways to compute the curves of FIG. 14 are discussed by Born and Wolf in "Principles of Optics" $6^{th}$ Edition Cambridge University Press, 1997 beginning at page 51, and by Azzam and Bashara in "Ellipsometry and Polarized Light" North-Holland, 1987 pgs. 270–315, for example. The equations relating reflectivity of a thin film to the absorbing layer thickness can be found in "Ellipsometry and Polarized Light" referenced above on pages 283 through 288, for example. These equations or similar ones referenced in Born and Wolf may be incorporated into the computer software to automatically predict the film thickness from the reflectivity of the disk. In order to predict the film thickness it is first necessary to know the complex indices of refraction of the carbon 104 and magnetic layers 106. The change in reflectivity of the points in the first quadrant of the histogram can be related to the wear of the carbon through the theoretical change in reflectivity scale (on the right side of FIG. 14) such as the curve illustrated in FIG. 14. The absolute reflectivity scale on the left of FIG. 14 can be used to compute the absolute thickness of the carbon. The computation of the absolute thickness of the carbon requires knowledge of the complex indices of refraction of the carbon and magnetic layers. A similar curve can be computed with the S polarized reflectance from the thin film disk.

The reflectance on the left and right scales of FIG. 14 are those measured experimentally by the sum of $P_{sp}$ and $P_{sc}$. A system which uses only the specular component of light will ignore the light which has been scattered and will give a measurement of carbon thickness or wear which is incorrect. An additional advantage of using the sum of the specular and scattered components is that the signal from the carbon wear is essential doubled. This is because as the carbon wears the P specular component increases as well as the P scattered component. The P scattered component increases since most of the P light penetrates the absorbing film and scatters off the magnetic layer 106. As the carbon is thinned the amount of scattered light from the magnetic layer 106 will increase, since there is less carbon to absorb the scattered light from the magnetic layer.

Figure 15:
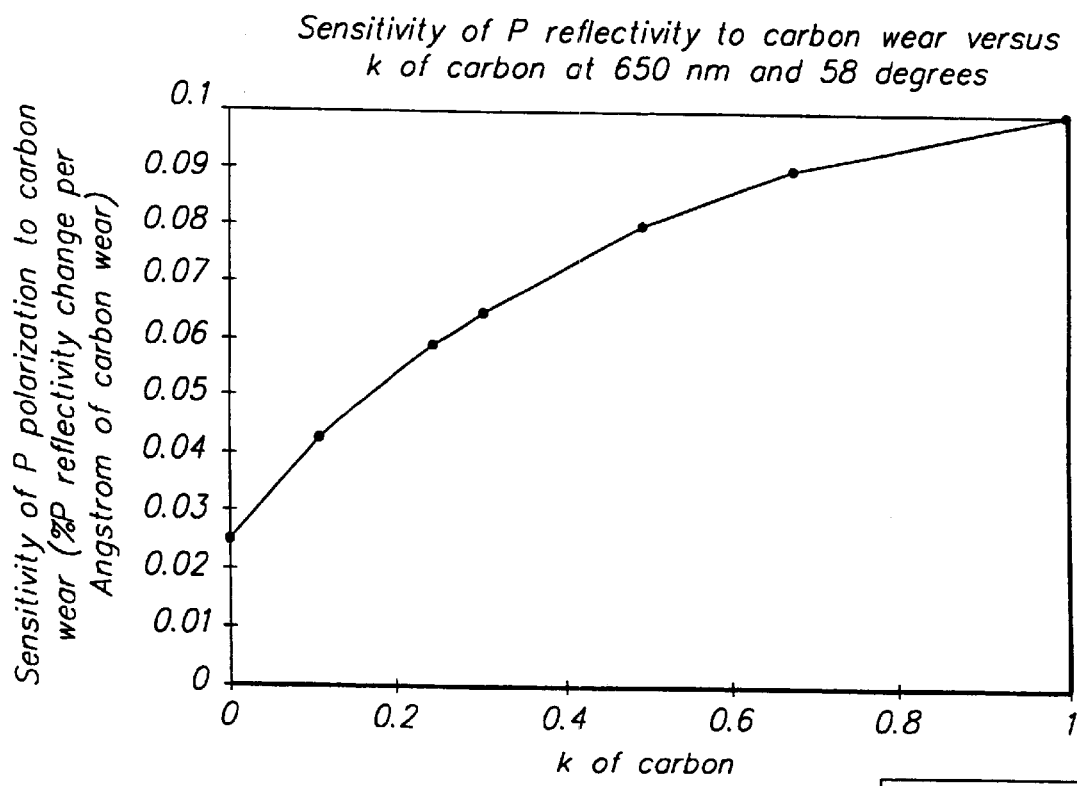
FIG. 15 is a graph illustrating the sensitivity of P polarized light reflectivity to carbon wear verses the k of carbon for a light signal having a wavelength of 650 nm and having an angle of incidence of 58 degrees.

An alternative method for identifying the amount of carbon wear is to measure the k (complex part of the index of refraction) of the carbon and use the percentage reflectivity change per angstrom of carbon wear. FIG. 15 is a graph illustrating the sensitivity of P polarized light reflectivity to carbon wear verses the k of carbon for a light signal having a wavelength of 650 nm and having an angle of incidence of 58 degrees. FIG. 15 illustrates the relationship between the sensitivity of P polarized light to carbon wear versus the imaginary portion of the index of refraction (k) of the carbon. The initial slope (at 200-Angstrom thickness) of the curve in FIG. 14 is similar to the ordinate illustrated in FIG. 15 where the changes in the ordinate are due to the changes in the k of the carbon. The abscissa is the k of the carbon and the ordinate is the sensitivity of the P specular light to changes in carbon thickness, expressed in the percentage of P polarized light reflectivity change per Angstrom of carbon wear. Typical carbons have k values near 0.4, making the sensitivity about 0.07 percent per Angstrom of carbon wear. This technique allows the detection of 0.01 percent change in the reflectivity and, therefore changes in carbon wear of less than one Angstrom. The graph of FIG. 15 can be used to determine an approximate measure of the carbon wear. The initial slope of the curve in FIG. 14 is given as the k=0.4 value illustrated in FIG. 15. The first technique, using FIG. 14, has the advantage of accounting for the nonlinearity of the reflectivity change vs. wear. The second technique, using FIG. 15, has the advantage of simplicity. The analysis of the carbon wear is aided by the use of a one-dimensional wear histogram. The pixels in the image corresponding to carbon wear (the first quadrant if the angle of incidence is 58 degrees) are plotted in a histogram. This one-dimensional histogram has as the ordinate the number of pixels and the abscissa is the amount of carbon wear as calibrated above. The histogram allows the user to display the amount of the surface which is worn (the number of pixels) versus the amount of wear. In this manner the user can select the amount of wear (a point on the abscissa) and determine the percentage of the surface area, which is worn above or below this amount of wear. This aids the comparison of different carbon surfaces in their response to wear induced by the thin film head.

The analysis of the data is accomplished by analyzing the images of the thin film disk as a function of time. The disk is subject to some action such as start/stops of the thin film head, which may alter the disk surface as described above. Images of the disk are repeated at certain time intervals and these images are analyzed in steps 702–716 via the two dimensional histograms. An example of carbon wear analysis using an in situ procedure is shown in FIG. 18. The steps of collecting images and analyzing them 702–716 are repeated until the experiment comes to a conclusion. The images are constructed by moving the apparatus 200 across a radius of the thin film disk with a very accurate stepper motor while rotating the disk at a high rate of speed (1000 to 20000 rpm).

The spindle which rotates the disk at a high rate of speed contains an encoder which produces 1024 pulses as it rotates through 360 degrees, for example. This encoder is used to determine the circumferential positions around the disk. The present invention preferably utilizes a very high-resolution determination of the position around the circumference of the disk. This is accomplished by using a phase locked loop to multiply the encoder signal by a selectable factor of up to 64 times. The phase locked loop, which multiplies the 1024 encoder pulses, has the ability to track any velocity jitter in the encoder. This feature allows averaging of repeated revolutions to be done with no loss of lateral resolution. That is, subsequent revolutions lie in phase with one another and when averaged, the resulting image is not smeared by any jitter effect. Averaging is done to improve signal-to-noise ratio.

The spectrum of spindle jitter is assumed to be related to the frequency of spindle rotation, and limited to some multiple of it. Jitter can be due, for example, to the variations in torque from the motor poles. Regardless of spindle-frequency jitter, the encoder output nonetheless exactly tracks data on the disk. It would be ideal therefore to synchronize the data-acquisition clock to the encoder. In practice, there are limitations on the frequency at which the clock can be made to track the encoder. In the phase-locked loop (which generates the clock for the Analog to digital converter from the encoder) the encoder is compared to the internal clock reference, generating phase-error pulses. The duty cycle of these pulses constitutes an error signal indicating whether the internal reference matches the encoder frequency or should be adjusted to maintain tracking. To convert these pulses to an average voltage useful as an error signal requires a low-pass filter, which limits the tracking bandwidth. A conflicting parameter is the error-signal ripple, which diminishes as the low-pass filter cutoff frequency is lowered. Ripple on the error signal leads to small variations in the frequency of the multiplied clock. This rise and fall of the clock frequency during each encoder period, while consistent from scan to scan, and therefore not a threat to averaging could, if large in magnitude, distort the appearance of data features. The repeatable part of the spindle jitter is not a threat to averaging (although it may distort the image). The non-repeatable part of the jitter will smear out the averaged image and this circuit will remove this smearing resulting in high resolution, high signal to noise images.

Since the encoder frequency is 1024 times the spindle frequency, compromise can be struck, placing the cutoff frequency of the low-pass filter at about 50–100 times higher than the spindle frequency, and about 10–20 times lower than the encoder frequency. In this way, spindle jitter up to >50 times the spindle frequency is tracked, while th e clock frequency remains stable to within ± a few percent. Since the en coder frequency varies widely, the cutoff frequency of the low-pass filter should be adjusted to maintain the ratios set forth above. The 68:1 encoder-frequency range of one embodiment of the present invention is divided into seven 2:1 ranges, each of which uses a different, fixed filter configuration set by switching the appropriate capacitor through an analog multiplexer.

Figure 19:
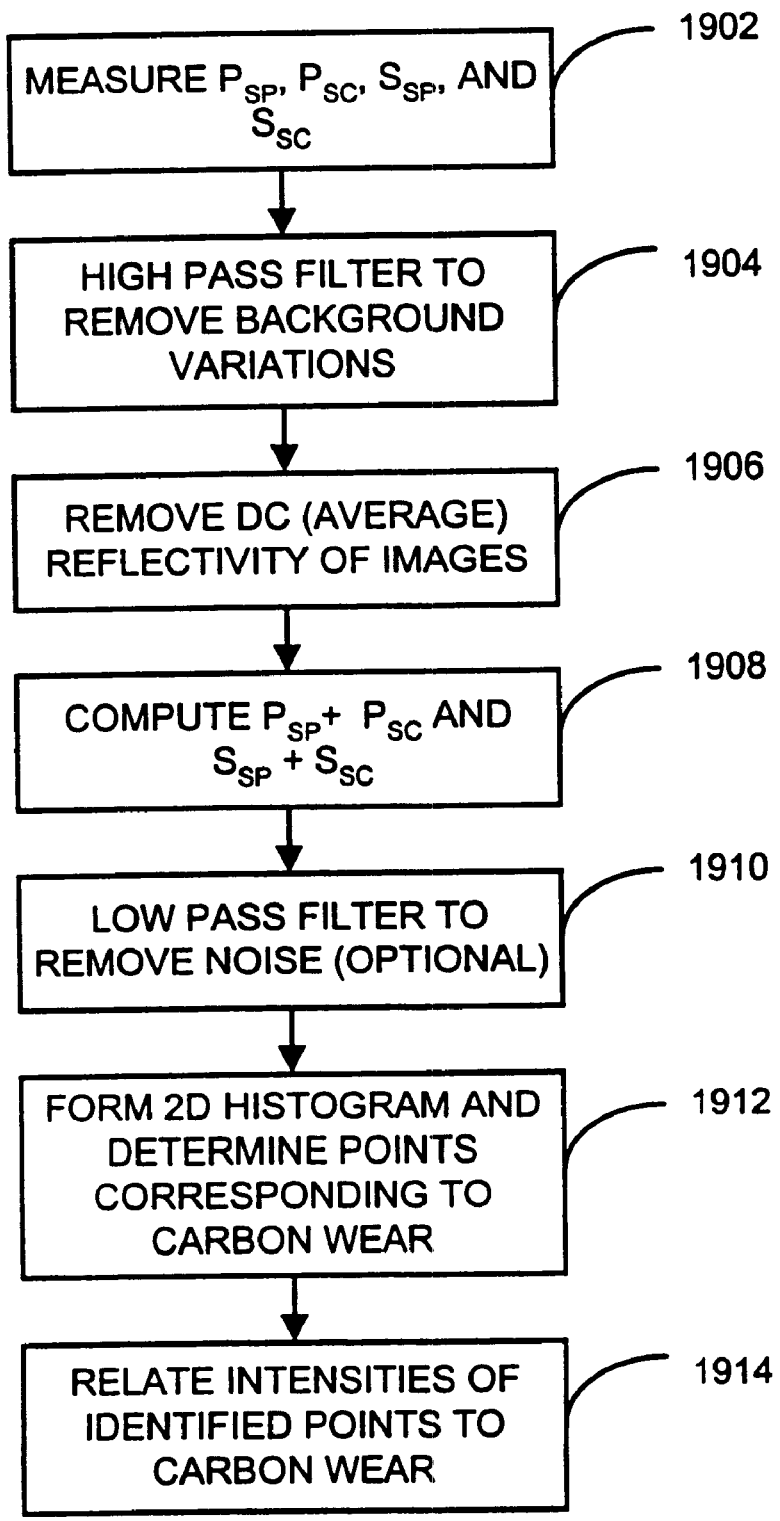
FIG. 19 is a flow chart illustrating a method for measuring carbon wear for an ex situ process according to an embodiment of the present invention.

As described above, in an embodiment, the measurement of the thin film disk properties is accomplished in situ. In an alternate embodiment, the measurement of the thin film properties is accomplished ex situ. FIG. 19 is a flow chart illustrating the method for measuring carbon wear using an ex situ procedure according to the present invention. One technique for measuring the thin film disk properties ex situ is to test the thin film magnetic disk on a separate test stand. This means that no reference image needs to be taken. The user places the disk on the spindle and the apparatus illustrated in FIG. 2 scans the disk for carbon wear. This scan provides a measure of the carbon wear, lubricant depletion, lubricant pooling, and surface roughness changes at the completion of the experiment. The user measures 1902 $P_{sp}$, $P_{sc}$, $S_{sp}$, and $S_{sc}$. The images are high pass filtered 1904 to remove any background variations and the DC value of the reflectivity is removed 1906 by setting the average value of the image to zero. The summed images $P_{sp}+P_{sc}$ and $S_{sp}+S_{sc}$ are then computed 1908 and low pass filtered 1910 to remove noise, if necessary. The two dimensional histogram is then computed 1912 and the points corresponding to carbon wear are identified. The intensities of these points are related 1914 to the carbon wear in angstroms via such curves as FIG. 14 and FIG. 15.

The absolute thickness of the carbon may be computed by relating the sum of $P_{sp}$ and $P_{sc}$ or the sum of $S_{sp}$ and $S_{sc}$ via a theoretical model such as shown FIG. 14 to the carbon thickness. This method is not limited to measuring carbon thickness but can be applied to any reflective substrate which is coated with an absorbing coating.

Manufacturers make thin film disks with a known carbon overcoat thickness. The control of the carbon thickness is on the order of +/−10%. The knowledge of absolute thickness and the complex indices of refraction of the carbon allow one to construct calibration curves such as FIGS. 14 and 15 and as a result one can determine the amount of carbon wear. The change in the thickness of the lubricant can be determined from the second or fourth quadrants of the two dimensional histogram. The calibration factors for the lubricant are taken from a curve, as described above. The calibration factor will depend at what angle the particular embodiment is operating. If the embodiment is operating at an angle between 53 and 71 degrees then the data falling in the fourth quadrant corresponds to lubricant pooling and in the second quadrant to lubricant depletion. The absolute thickness of the lubricant can be determined by removing a section of the lubricant on the disk 100 with a suitable solvent. The reflectivity corresponding to the step may be measured in P or S specular reflectivity. This reflectivity change may be related to the thickness of the lubricant via curves such as FIG. 8. Curves such as FIG. 8 may be computed with software such as "Film Star" that is commercially available from FTG Software Associates, in Princeton, N.J. Either S or P reflectivity may be used but S reflectivity is preferred since the sensitivity to lubricant in S reflectivity is nearly independent of the k of the carbon when k is less than 1.

When the embodiment is operating at an angle between 53 and 71 degrees the measurement of a step in the lubricant can be enhanced by performing the ratio of the S image to the P image or vice versa. This gives an enhanced contrast to lubricant for two reasons: 1) the ratio of P to S or S to P removes most reflectivity variations on the disk and shows only the step in the lubricant. 2) The response of S light to the lubricant step is opposite to that for P light and as a result the ratio image increases the signal from the lubricant step. The sensitivity of the ratio of the S to P image (or P to S) to lubricant may be calibrated in a manner similar to the S or P specular images are calibrated for lubricant thickness.

Tribologists need to measure how lubricants move on the surface of thin film disks 100 since the motion of the lubricant is very important in determining the durability of the carbon protective layer. The ratio may also be used to observe the motion (mobility) of the lubricant. The ratio gives enhanced contrast and removes reflectivity variations unrelated to the lubricant step, as discussed above. The ratio also allows the user to remove the disk with a lubricant step and place them under some environmental stress (such as humidity or temperature) and then replace the disk and measure how far the lubricant step has moved. This would not be possible without using the ratio, as the absolute images do not have sufficient contrast to pick out the lubricant step.

The ratio of the P to the S images can also be used to identify deep or unusual texture lines on the disk surface. This is possible since the ratio of these images is related to the index of refraction of the area being sampled by the optical beam. Unusual or deep texture lines have less carbon on them or contaminates within them. As a result the ratio image gives a strong contrast to deep or unusual texture lines since the lack of carbon or contaminates changes the index of refraction and as a result the ratio of P to S or S to P. The ratio of the P to the S images can also be used to identify contamination on the disk since contamination on the disk will cause the optical properties to change. In particular, the complex index of refraction will be changed by a contaminate beneath or upon the film and the ratio of P to S will show this as a contrast between various areas of the disk. The individual images will also show contaminates as changes in reflectivity, however the ratio of P to S or S to P will show the changes more clearly since the ratio is constant except for areas where contamination is present.

Figure 17:
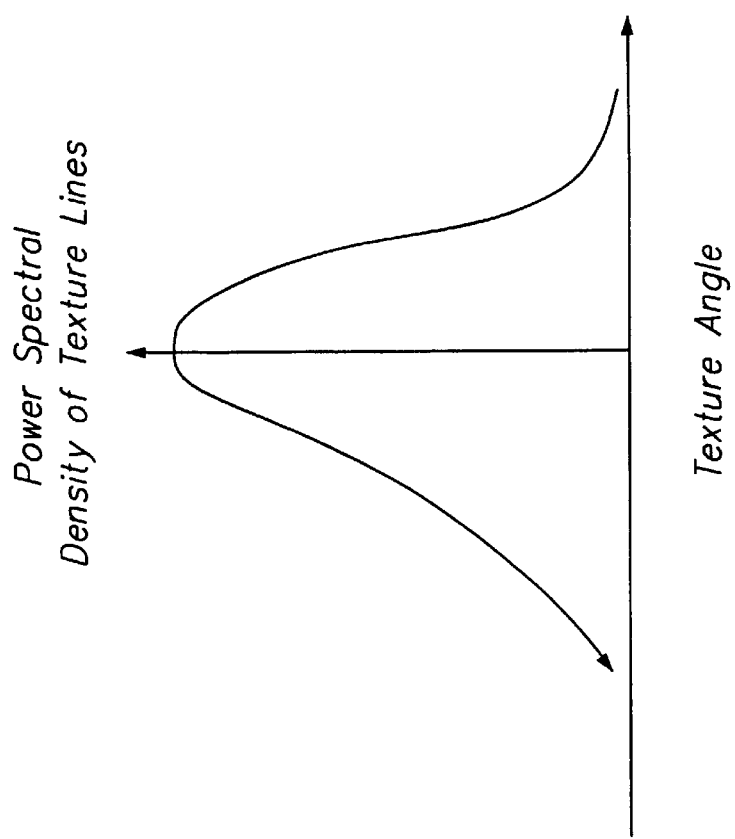
FIG. 17 is an illustration of a cut through the fast Fourier transform showing the texture angles, width and texture amplitude distribution of a disk texture line pattern.
Figure 16:
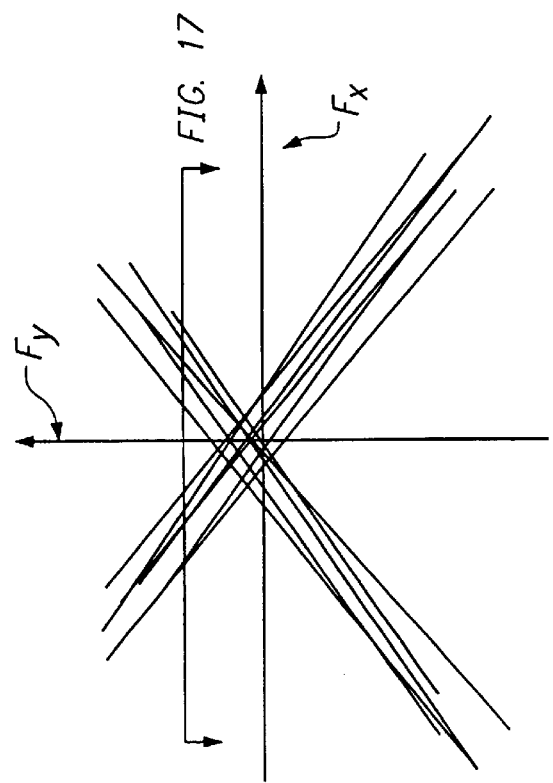
FIG. 16 is an illustration of a two dimensional fast Fourier transform of a S specular image as measured by an embodiment of the present invention.

In addition to measuring the lubricant properties and carbon wear, the present invention can simultaneously measure the surface roughness of the thin film disk 100 using the technique described above. The image of the roughness of the thin film magnetic disk gives the variation of the roughness of the disk with position. The roughness or polish of the disk is typically due to a mechanical polish, which produces polish marks, which are roughly circumferential in nature. By making the Fast Fourier Transform (FFT) of the roughness image (obtained from equation 1) or one of the specular images one can display the spatial frequencies of the roughly circumferential polish in the spatial frequency domain. The FFT can be used to measure the angular distribution of the polish lines, which is a parameter of interest in the manufacture of thin film disks. The FFT of the roughness image gives the angular distribution of the roughness of the texture lines and the roughness power density of the texture lines running along a particular direction. FIG. 16 is an illustration of a FFT of a disk texture taken from the roughness image or one of the specular images as utilized by an embodiment of the present invention. A cut through this FFT provides the roughness power density of the texture lines verses the angle and the angular width of the texture line roughness distribution. FIG. 17 is an illustration of a cut through the fast Fourier transform showing the texture angles, width and texture power density distribution of a disk texture line pattern.

Another feature of the present invention is a method of automatically focusing the apparatus 200 shown in FIG. 2. Automatic focusing can be accomplished by placing a laser zone textured disk on the spinstand, which accompanies the instrument. A laser zone textured disk is a magnetic thin film disk which has a series of laser melted protuberances placed in a spiral pattern near the inner diameter of the disk. The laser-melted protuberances prevent the thin film head from sticking to the disk when the disk is stopped. A spin stand is a test stand upon which the disk is placed which rotates the disk and simulates the action of a disk drive. The apparatus 200 shown in FIG. 2 is placed over the laser textured zone of the thin film magnetic disk and the specular and scattered output is observed on an oscilloscope while the focus is adjusted. When the instrument comes to a focus the specular and scattered signals from the laser bumps will reach a maximum value.

The properties of lubricants are sensitive to humidity, therefore it is important to measure lubricant property as the humidity changes. Often the instrument 200 will operate in a high humidity environment. Heated optics allows operation of this embodiment of the present invention in high humidity environment. The optics of the instrument are heated to slightly above the environment temperature so that when used in a humid environment water will not condense upon the optics. One technique for heating the optics is to use the heat generated by the electronics within the optical enclosure. An alternative technique is to place a small heater in or near the optical assembly 200.

In an alternate embodiment of the present invention the above optical surface analysis apparatus and method are used for rapid measurement of RMS roughness of laser bumps on thin film disk magnetic media which can be correlated to laser bump heights. This is useful as a process control feedback in the manufacture of laser-bumps on thin film disks. An embodiment of the present invention includes a small spot size scatterometer (3-micron resolution) which allows one to resolve the scattered light from individual laser texture bumps. The RMS roughness of the individual laser bumps can be determined from the ratio of the scattered to the specularly reflected light as computed from equation (1). The RMS roughness of individually resolved laser bumps is a function of the height of the laser bumps. Therefore the measurement of the RMS roughness of laser texture bumps can be used to monitor the height and the height distribution of laser texture bumps. This technique has the distinct advantage of being extremely fast (10 MHz data rate)—orders of magnitude faster than conventional optical or mechanical techniques for determining laser bump height.

In an alternate embodiment of the present invention the above optical surface analysis apparatus and method are used to help identify the effects of burnish or glide head on the lubricant layer 102 and/or the carbon layer 104. A burnish head is a low flying ceramic slider that flies near the surface of the disk. In doing so it removes asperites from the surface of the disk. A glide head is a low flying ceramic slider that is equipped with a piezoelectric sensor, in an embodiment. The glide head is flown over the surface of the disk and when it encounters an asperity it sends a signal that indicates a defect is present on the disk.

It is typically difficult to observe the effects of a burnish or glide head on the lubricant layer 102 or the carbon layer 104 since there is no conventional system or method for observing these effects in situ, i.e., while in the process of burnishing or gliding the disk. One embodiment of the invention combines the system and method described above for measuring thin film disk properties with magnetics, friction, stiction, burnish heads and acoustic emission for glide in the manner described below. The combination permits inspection of the effects of burnish and glide on the carbon layer 104, e.g., changes in roughness, texture, and/or carbon layer thickness.

During track following, which is when the thin film slider stays at one particular radius of the thin film disk for a prolonged period of time, or during accessing on a thin film disk it is possible for the slider to deplete, pool, or degrade the lubricant layer 102. This embodiment of the present invention measures and analyzes these effects while they occur. For example, a layer of degraded lubricant can form on the disk as a result of prolonged track following. This embodiment measures the lubricant layer 102 properties by measuring the effect the changes in the lubricant has on the magnetic signals. The result of changes in carbon thickness are measured by changes in the amplitude of the magnetic signal. In addition, all of the measurements can be made in situ, i.e., without removing the disk from the spindle.

This embodiment of the present invention is a tool for characterizing surface properties such as roughness, lubricant depletion/pooling, lubricant degradation, surface debris, and carbon wear. It measures and images the disk surface. There are tools with a spindle and a rotary actuator that can simulate the action of a disk drive, they are commonly known as "spinstands". It also simulates the wear and tear done by the magnetic head as it contacts the disk surface during starting and stopping of the spindle. In addition, the spinstand can include tools that measure other properties of the disk. For example, head to disk stiction/friction, magnetic signal amplitude of the disk, acoustic emission from contacts between the head and the disk, and sensors that detect and map surface features that protrude above the mean fly-height of the head.

In one embodiment the above described capabilities are combined, which enables the data from each tool to be correlated to the measurements of the other tools. This allows the user to correlate the data because the various measurements can be done simultaneously or sequentially and in-situ. This significantly enhances the usefulness of the tool. For example, the mechanism behind the failure of a thin film disk during spindle start/stop can be better understood. In addition, the evolution of lubricant degradation/depletion, carbon wear, and surface roughness changes can be followed as a function of the number of spindle start/stops.

In combining this embodiment of the present invention with the spinstand, the optical component of the invention 200 and the spinstand rotary actuator and magnetic head are in very close vicinity. The optical components 200 optimally should not take up more than one half of the disk area, otherwise it could collide with the spinstand rotary actuator. The invention 200 has a miniaturized form; in particular the integrating sphere is miniaturized because it is the closest to the rotary actuator, which holds the magnetic head.

Another embodiment of the present invention combines the apparatus and method for measuring thin film properties, described above, with high resolution optical or mechanical tools such as an atomic force microscope (AFM) to quickly and easily identify damaged areas on a thin film disk. A conventional atomic force microscope, for example model DI-5000 from Digital Instruments, Santa Barbara, Calif., is capable of providing a very high resolution image of a surface but has a very small detection range (viewing diameter), e.g., approximately 100 micrometers. Accordingly, it is extremely difficult to find areas on a thin film disk that are damaged using conventional AFMs. However, the apparatus 200 and method described above easily and quickly locates damaged areas on a thin film disk 100. As described above, one embodiment of the present invention identifies thin film disk damage in the form of carbon wear, surface roughness, lubricant depletion, lubricant pooling, and lubricant degradation, for example. This embodiment of the present invention uses the optical analyzer apparatus 200 to quickly and inexpensively locate damaged portions of a thin film disk 100. The apparatus 200 precisely identifies the damaged locations. The AFM is directed to examine the precisely identified damaged locations. This embodiment enables the AFM to locate and perform a very detailed analysis of the damaged portion of the disk. Accordingly, this embodiment of the present invention enables a user to quickly and inexpensively locate one or more damaged portions on a thin film disk 100 and enables the user to direct an AFM directly onto the damaged portions much more quickly than is possible using conventional systems and methods.

A specific example is the study of carbon wear on laser bumps, it is desirable to be able to find specific laser bumps (from hundreds of thousands of laser bumps) which have carbon wear. It is preferable to locate these worn bumps quickly and to study these laser bumps under a high power and high resolution measurement or imaging tool. The present invention is able to locate the laser bumps quickly but it does not have the resolution for studying the laser bumps in extreme detail. Conversely, high resolution tools, such as an Atomic Force Microscope (AFM) are too slow to analyze large number of bumps. A combination of the two types of tools provides the advantages of both tools. Laser bumps of interest (with carbon wear) can be found quickly using the present invention, the position encoder of the spindle holding the disk can track their locations. The same spindle can also calibrate the relative location of the optical beam position to the location of the AFM. These laser bumps can then be placed under the high-resolution tool (e.g. AFM) for further study.

Figure 20:
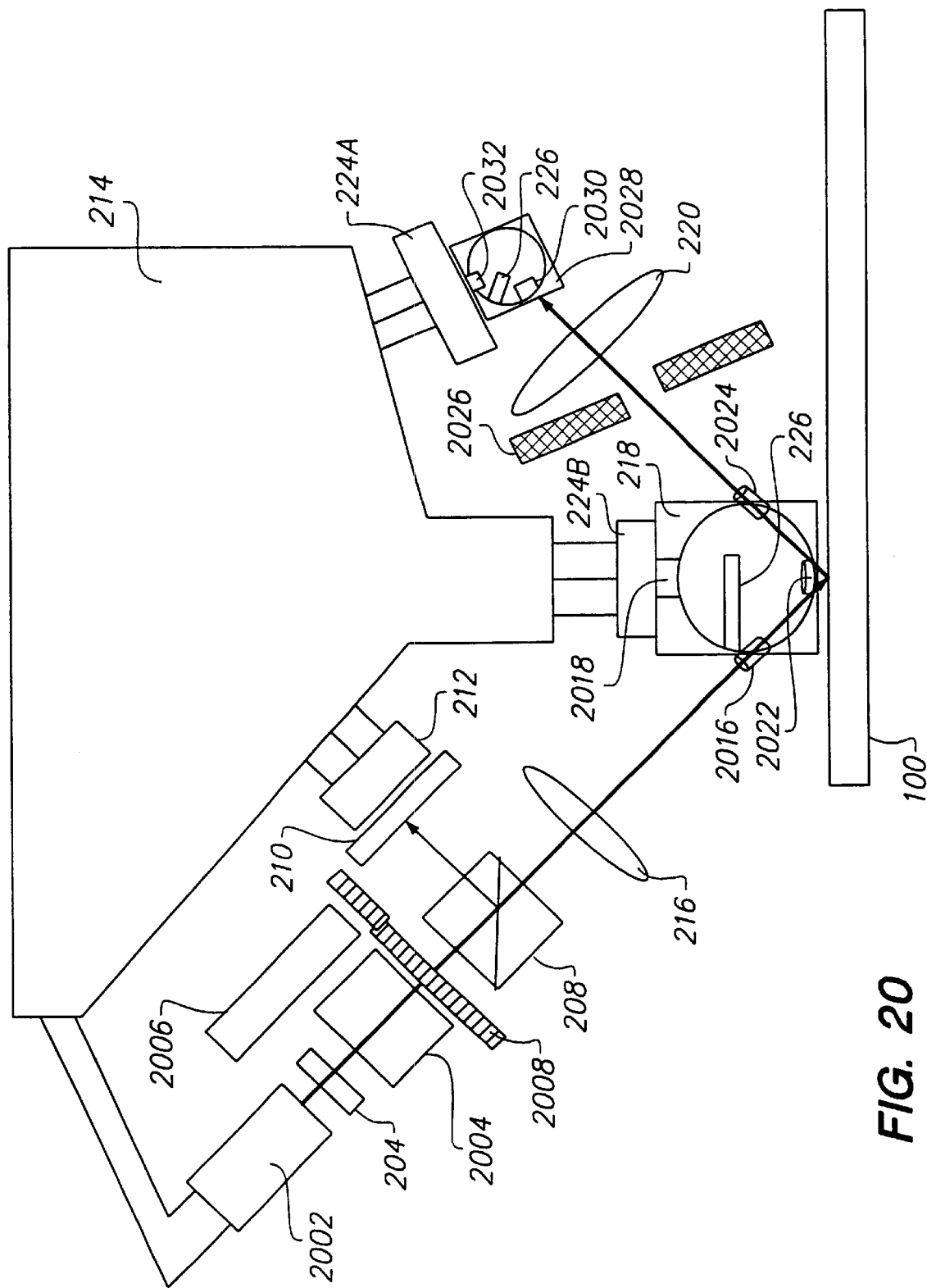
FIG. 20 is an illustration of a high temperature thin film measurement system 2000 according to one embodiment of the present invention.

Another embodiment of the present invention is a system and method for performing high temperature film measurement. FIG. 20 is an illustration of a high temperature thin film measurement system 2000 according to one embodiment of the present invention. The high temperature system 2000 is a reverse angle illustration when compared to the view illustrated in FIG. 2. The system 2000 is capable of measuring the carbon film thickness and wear, lubricant film thickness and thickness variation, surface roughness, and degradation of lubricant. The system design is similar to design set forth above with respect to FIG. 2, for example. One variation is that the high temperature thin film measurement system 2000 allows operation at high temperatures, e.g., 80 degrees Celsius. The high temperature thin film measurement system 2000 uses a zero order temperature compensated quartz half wave plate 2004 available from, for example, CVI Laser, Albuquerque, N. Mex. and a high temperature laser diode 2002 available from, for example Rohm Co., LTD. Kyoto, Japan. The zero order quartz half-wave plate 2004 is mounted in a rotatable housing that can be rotated through 45 degrees by a miniature motor, for example Maxon Precision Motors, Burlingame, Calif. model No. 118426 using gears 2008 that are commercially available from W. M. Berg, East Rockaway, N.Y. Rotating the half wave plate through 45 degrees will rotate the polarization by 90 degrees. The high temperature thin film measurement system 2000 also includes an integrating sphere 218 and baffle 226 that can be similar to those described above with reference to FIG. 2. The integrating sphere 218 is cut out of the interior of a cubic aluminum block. The high temperature thin film measurement system 2000 also includes a focusing lens 216 and a collimating lens 220 similar to FIG. 2. The high temperature thin film measurement system 2000 also includes feedback circuitry substantially identical to that described in FIG. 4 for controlling laser intensity, and amplifying, signal conditioning and digitizing electronics substantially identical to that described in FIG. 6.

One problem to be solved is to develop a high temperature film measurement system. Hard disk drive and disk manufacturers need to test the carbon and lubricant on their disks at relatively high temperatures, e.g., 80 degrees Celsius. This can be accomplished by making a film measurement system which can be operated at these temperatures. The means to accomplish this is to use a mechanically rotatable temperature compensated zero order half wave plate 2004 together with a high temperature laser diode 2002. The laser which is used is available from Rohm Co., LTD. In Kyoto, Japan and the model number is RLD-78MAT1. This is a 780 nm laser diode which has low noise and can operate continuously at 80 degrees C. The temperature compensated zero order half wave plate is available from CVI Laser Corp. in Albuquerque, N. Mex., USA. All the other optical and electrical components are rated at temperatures higher than 80 degrees C., so the resulting system can be operated up to 80 degrees C. and it may be operated at a humidity of 80% RH (relative humidity).

Disk drive companies and their suppliers test the thin film disks and the completed disk drives in environments of up to 70 degrees C. at a relative humidity of 80%, for example. Conventional systems use a laser which is either Peltier cooled or an uncooled intensity stabilized laser. The Peltier cooled laser suffers from several problems, namely, when attempting to use a cooled laser (cooled for example to 25 degrees C.) in a chamber at a temperature of 70 degrees C. and a relative humidity of 80%, water will condense on the cooled surface of the laser thus damaging the optical surface. Attempts to operate the Peltier cooler at a temperature of greater than 50 or 60 degrees C. can damage a conventional laser. The embodiment shown in FIG. 20 uses an uncooled laser 2002 that has been developed for continuous operation at a temperature of 80 degrees C. The system described in FIG. 20 will also work at a relative humidity of 80% since the laser actually operates at a temperature slightly greater than its ambient surroundings.

Another problem which needs to be overcome in high temperature systems is a means to switch the polarization between the P and S polarizations. Conventional liquid crystal variable half wave plates 206 cannot be operated above 50 degrees C. A solution to this problem is to use a zero order thermally compensated half-wave plate. The type of wave plate has a thermal compensation which allows it to operate to temperatures greater than 80 degrees C. The zero-order half wave plate is mechanically rotated in order to switch the polarization between the P and S states. This is accomplished by a miniature electric motor 2006 and gears 2008. In order to reduce the effect of temperature on the electronics the preamplifier and laser regulator board 214 are located outside the high temperature environment. The connections between the photodetectors and the board 214 are made with cables.

The system shown in FIG. 20 operates in a manner similar to that shown in FIG. 2. This system has a input aperture 2016 in the integrating sphere 218 which is slightly larger than the optical beam so that the beam is not eclipsed by the opening. The integrating sphere 218 has a hole 2022 in its bottom that allows the beam to strike the disk and reflect out of the integrating sphere through an aperture 2024. Aperture 2024 is slightly larger than the beam to allow the beam to pass through without being eclipsed. The location of aperture 2024 is less than 1 cm from the surface of the disk. The diameter of aperture 2024 can control the minimum spatial frequency of roughness, which the device can measure according to equation (3), discussed supra. The integrating sphere includes an opening at its top 2018 to allow scattered light to strike the scattered photodetector 224B. The specular beam is directed onto a collimating lens 220 which prevents the beam from spreading. After passing through the collimating lens it passes into a miniature integrating sphere 2028 through an opening 2030. The integrating sphere reduces the sensitivity of the photodetector to disk distortion and runout. A distorted disk is one which differs from a perfect flat plane. The manufacturing process or the process of clamping the disk on the spindle can cause distortion of a disk. Disk runout is the motion of the disk in the vertical direction caused by imperfection in the spindle and mechanical vibrations of the disk. The specular intensity is detected via a hole 2032 in the miniature integrating sphere with a specular photodetector 224A. The hole 2030 is designed to be larger than the collimated specular beam so that the beam is not eclipsed by the beam. The integrating sphere 2028 is rotated slightly in the plane of the paper so that its entrance port is not perpendicular to the beam. This means that the reflected signal from the back of the integrating sphere 2028 will not retro-reflect down the optical path into the scattered light integrating sphere 218. Retro-reflect means to reflect substantially directly down the path of the incoming laser beam. The amount of reflected light which gets into the integrating sphere 218 is further reduced by using an opaque black baffle 2026 placed between the integrating sphere 218 and the collimating lens 220. Another means of reducing the sensitivity of the specular photodetector 224A to disk distortion is to place a diffuser 222 in front of the specular photodetector 224A as shown in FIG. 2.

An optical surface analyzer, for example the apparatus 200, 2000 described above, measures thickness changes induced by wear of multiple layers of thin film coating on a reflective surface, e.g. magnetic disk media. Another feature of the present invention is a system and method for separating and identifying the signals from the different layers of the thin film using a 2-D histogram. This method is described in detail by Steven Meeks, W. Weresin, and H. Rosen in ASME Journal of Tribology, vol. 117, pg. 112, published in January 1995 which was incorporated by reference above.

The 2-D histogram is generated by the instrument software and allows the user to select specific areas of interest in the histogram, such as the carbon wear signal, by manually tracing a line around that area. The software then finds and highlights the location of the selected area of the histogram on the image of the disk by tracing back to the image source location. To construct a two dimensional histogram small regions (known as buckets) are defined in the P, S plane (the space of the histogram) which have a certain $\Delta P$ by $\Delta S$ dimension. Each coordinate pair (x,y) in the real space image is selected and its corresponding bucket into which its P, S coordinate falls is identified. After going through the entire image the total number of points in each bucket is identified and a color, for example, is assigned based upon the number of points in the bucket. The completed two dimensional image is known as a two-dimensional concentration histogram. The two-dimensional concentration histogram separates the regions of lubricant pooling, depletion, carbon wear and debris into separate regions. Debris are products generated as a result of the wear process on the disk. In addition, the slope of the histogram is related to the index of refraction of the layer being altered. One technique for generating a two-dimensional histograms is also discussed in detail by Bright and Marinenko, in *Microscopy: The Key Research Tool,* Vol. 22 pg. 21, 1992 in an article entitled "Concentration Histogram Imaging: A Quantitative View of Related Images".

Three embodiments of the present invention each use a method for automatically selecting specific areas of interest, such as the carbon wear signal, degraded lube, lubricant pooling/depletion, debris and defects without operator intervention and then using this information to optimize the type of carbon or lubricant or to analyze the failure of a disk drive.

The three methods are: (1) performing a symmetry operation about a centroid, (2) subtracting a reference histogram and (3) performing an and/not operation with a reference histogram.

Figure 21:
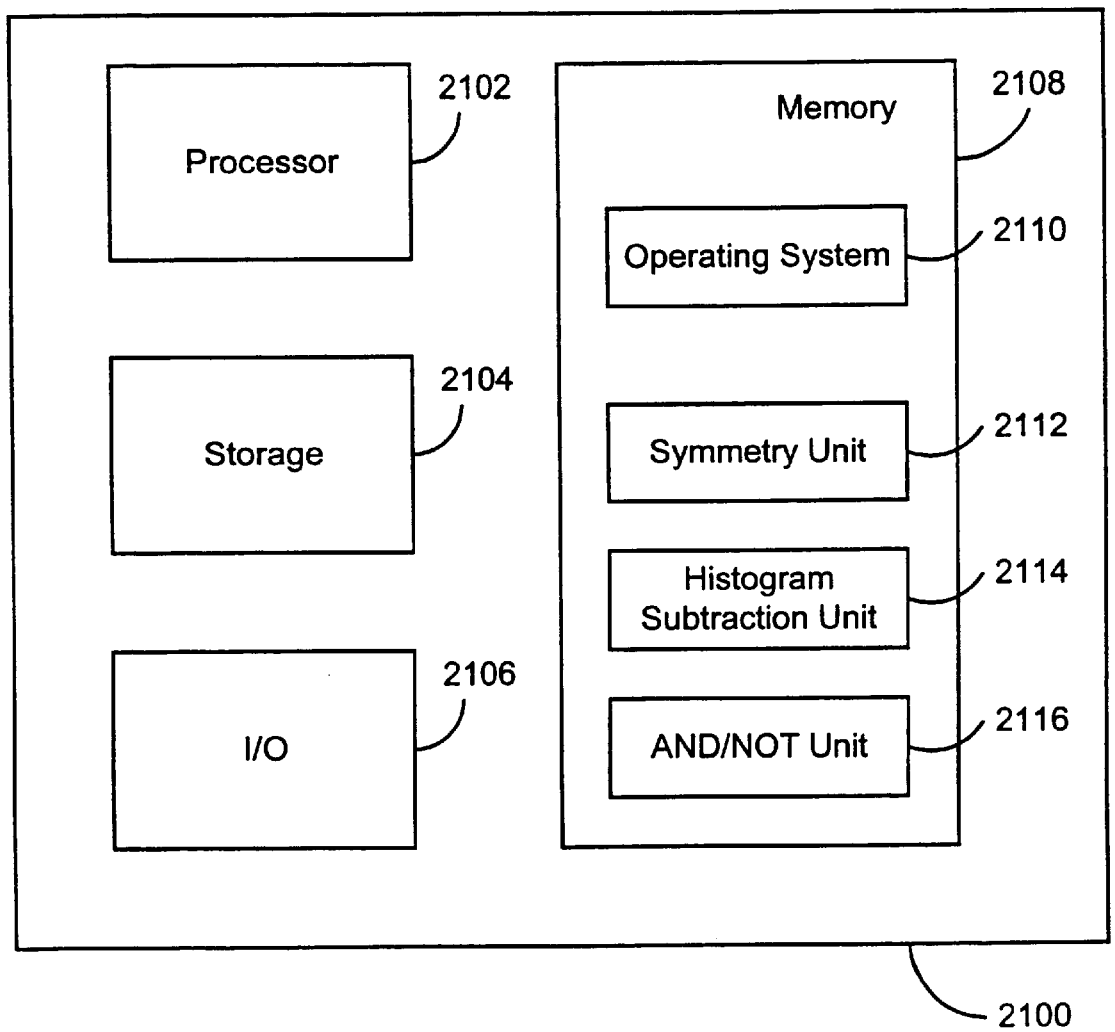
FIG. 21 is an illustration of a computer system according to an embodiment of the present invention.

The three embodiments can be performed in a conventional computer system, e.g., a personal computer, a microcontroller, a single chip computer, a network. As an example, these embodiments of present invention can be performed on a conventional computer system, e.g., a conventional personal computer, or a microcontroller for example, such as that illustrated in FIG. 21. The computer system illustrated in FIG. 21 includes a conventional processor, such as a Pentium II 400 MHz processor, a conventional storage unit 2104, a conventional I/O unit 2106 and conventional memory 2108. In one embodiment of the present invention the memory 2108 can include software related to the operating system 2110, e.g., Windows 98 that is commercially available from Microsoft Corporation, Redmond, Wash. In addition, some embodiments of the present invention can include one or more of the symmetry unit 2112, the histogram subtraction unit 2114, and the AND/NOT unit 2116. A more detailed description of the symmetry unit 2112, the histogram subtraction unit 2114, and the AND/NOT unit 2116 is set forth below.

Figure 22:
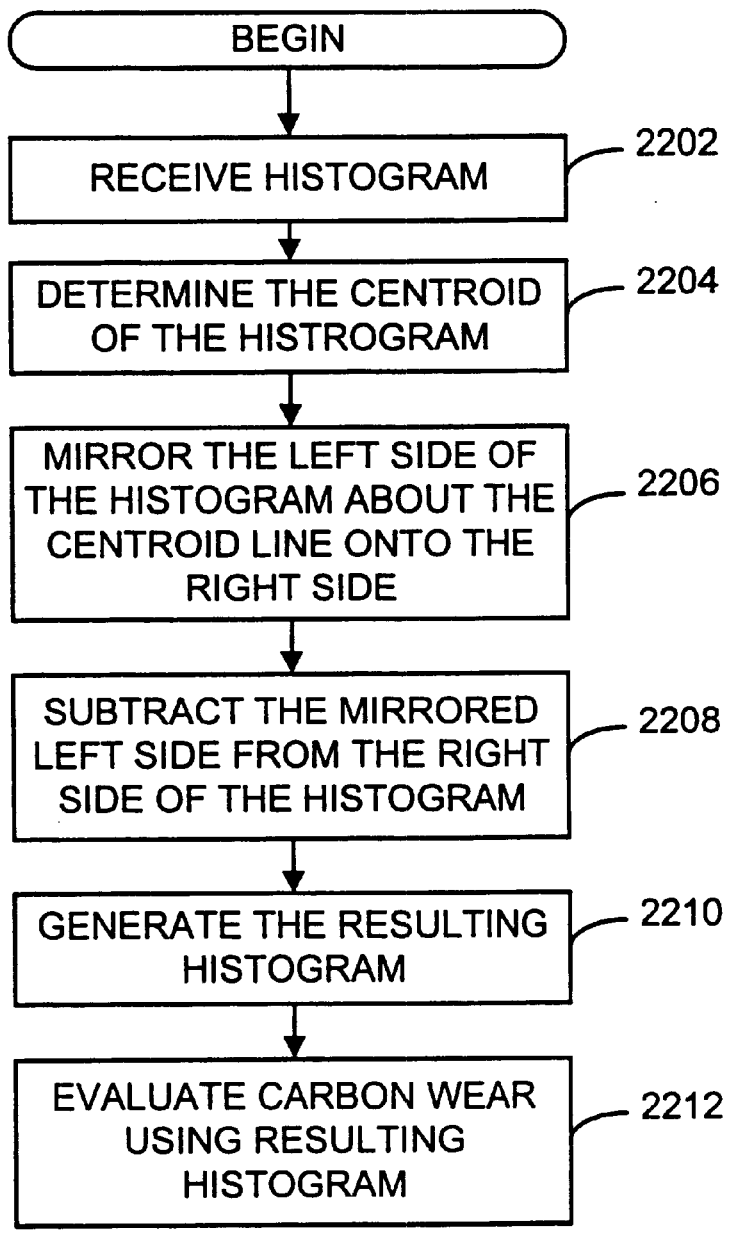
FIG. 22 is a flowchart illustrating the operation of the symmetry unit 2112 according to one embodiment of the present invention.

One embodiment of the present invention is to have the symmetry unit 2112 perform a symmetry operation about the centroid of the histogram to create a symmetric histogram about the centroid. FIG. 22 is a flowchart illustrating the operation of the symmetry unit 2112 according to one embodiment of the present invention. The symmetry unit 2112 receives 2202 the histogram. The two-dimensional histogram can be created in the manner described above. The symmetry unit 2112 determines 2204 the centroid of the histogram. One technique for identifying the centroid of a 2D Histogram is now set forth. The symmetry unit first converts the 2D histogram into a binary representation, e.g., any non-zero pixel values become '1' otherwise the pixel takes the value of "0". Second, from this binary image, a skeletonization/Medial Axis transformation in performed. Skeletonization is a process for reducing a binary image in to a skeletal remnant that largely preserves the extent and connectivity of the original region. Skeletonization is one of the morphological filters for Digital Image Processing. Further processing (e.g., pruning by thinning or erosion) may be necessary to produce a skeleton that is free of spurious spurs which can be introduced during the process of skeletonization. Next, other morphological filters can be used in addition to or separately from 'skeletonization' to get better representation of the centroid, such filters include: thinning, which is essentially reducing a binary image shape into a single pixel thickness, and erosion, which is a process to erode away the boundaries of the original region. This operation can remove speckle noise on the 2D histogram image, for example. One example of the skeletonization process is described in detail in 'Digital Imaging' by Howard E. Burdick, McGraw-Hill, 1997 which is incorporated by reference herein in its entirety.

The symmetry unit 2112 mirrors 2206 the left side of the histogram about the centroid line onto the right side and subtracts 2208 the mirrored left side from the right side of the histogram. The resulting histogram represents the asymmetric portions of the histogram which can be identified via a look up table as containing carbon wear, debris, defects, etc. Once the areas of interest are identified, parameters such as percent of. surface area covered by wear, depth of wear, degraded lube, etc., can be calculated automatically.

FIG. 25 is an example of a simplified two-dimensional histogram image according to an embodiment of the present invention. The signal from the thin-film thickness change (e.g. carbon wear) is shown as the shaded area 2502. The goal is to remove the non-shaded portion of the histogram from the data. This area can be automatically isolated from the rest of the image by calculating the centroid line 2504 that is a close approximation of the line of symmetry of the non-shaded area. The region 2506 of the histogram which is symmetric about the centroid line 2504 of the histogram image can then be removed from the data. In this example, the data to the left of the centroid line 2504 and its symmetric part on the opposite side of the centroid line 2504 is to be subtracted 2208 from the histogram. What remains is the shaded area 2502 which is the signal from the worn area. This area corresponding to carbon wear can be projected on to the $P_{sum}$ axis and with proper calibration they can give a quantitative amount of the carbon wear. The same calibration factors discussed earlier in this text may be used to compute the amount of carbon wear. This technique lends itself to the automatic analysis of data. For example, the automatic analysis of the percent of the surface worn and a 1D histogram of the wear of the carbon.

The 2D histogram consists of values at (x, y) bin positions whose amplitude is given by counting the number of points from two spatially identical images of amplitudes x and y which fall within the bin positions. Bin positions are the locations of small areas of dimensions Δx by Δy whose purpose is to serve as buckets which can accumulate and count the number of points which fall into these dimensions at a specified location. The 2D histogram may be formed by any two images measured over the same spatial location.

Figure 26:
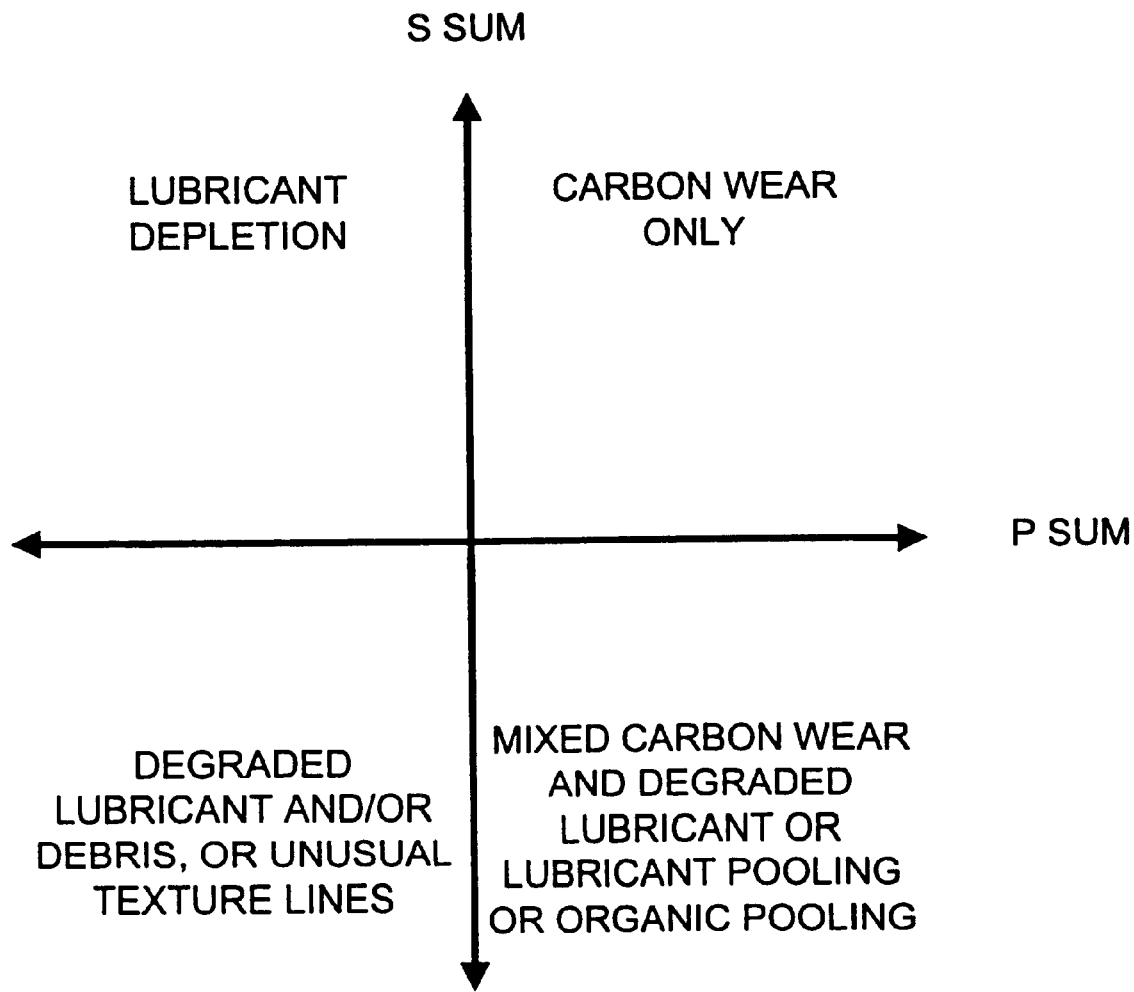
FIG. 26 is a chart illustrating an analysis technique according to one embodiment of the present invention.

The analysis of the portions of the histogram which remain after the subtraction of the symmetric part of the histogram can be analyzed based upon the values of the $P_{sum}$ and $S_{sum}$. FIG. 26 is a chart illustrating an analysis technique according to one embodiment of the present invention.

If the Psum/Ssum are both positive, i.e., the values fall into quadrant 1, the tested area of the disk has only carbon wear. If the values fall into quadrant 2 then the tested area of the disk has lubricant depletion. If the values fall into quadrant 3 then the tested area of the disk has degraded lubricant and/or debris, or unusual texture lines. If the values fall into quadrant 4 the tested area of the disk has mixed carbon wear and degraded lubricant or lubricant pooling or organic pooling.

Figure 23:
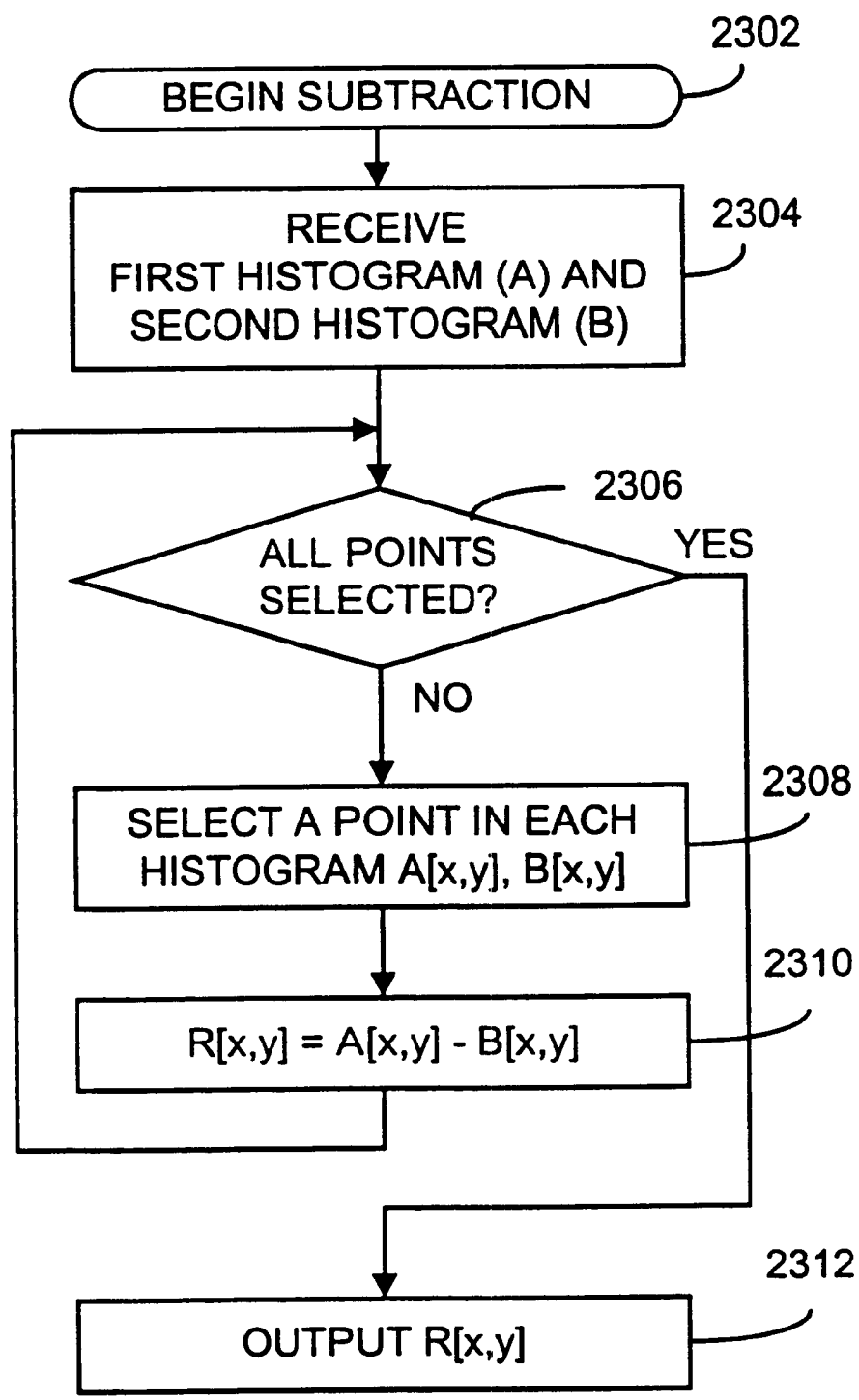
FIG. 23 is a flow chart illustrating the operation of the histogram subtraction unit 2114 according to one embodiment of the present invention.

Another embodiment of the present invention uses a reference histogram which is subtracted from the histogram of the disk to be measured. FIG. 23 is a flow chart illustrating the operation of the histogram subtraction unit 2114 according to one embodiment of the present invention. The histogram subtraction unit 2114 receives 2304 a first (reference) histogram that can represent measurements from a thin film disk which is very similar to the disk to be measured but has no damage on its surface. For example, the first histogram can be the histogram of the disk before testing, or a disk from the same batch (a sister disk) or the histogram from the untested side of the disk to be measured, for example.

If a reference histogram is not available from a sister disk, a reference histogram can also be obtained in one of several ways. The first way is to construct a 2D histogram from a subset of the current image (the surface under test). The subset is chosen on a region of the disk under test which has no damage, so that it provides a histogram of a virgin surface. Alternatively, a representation of the background (the reference histogram) can be obtained by performing a 'traceforward' operation on an undamaged region of the image that makes up the 2D Histogram of the disk under test. The 'traceforward' operation is performed on a subset of the image that is deemed to be free of defects or damage. The 'traceforward' operation is described in detail by Bright and Marinenko, in *Microscopy: The Key Research Tool*, Vol. 22 pg. 21, 1992 in an article entitled "Concentration Histogram Imaging: A Quantitative View of Related Images". The resulting collection of pixels which is now in the 2d histogram domain can be used as representative pixels of a background histogram for that particular image.

One technique for calculating the traceforward is to (1) first obtain the region on the original image where the traceforward is desired, and (2) for each pixel inside the region selected for the traceforward on the original images that form the 2D histogram a location in the 2D histogram can be calculated from the pixel value of the first image source and the second image source. The pixel values will fall into a particular x-axis bin and y-axis bin respectively, on the 2D histogram.

The histogram subtraction unit 2114 also receives 2304 a second histogram representing the disk after testing, for example. The histogram subtraction unit 2114 determines 2306 whether all points have been selected from each histogram. If not, the histogram subtraction unit 2114 selects 2308 a point in each histogram, e.g., A[x,y] and B[x,y]. The histogram subtraction unit 2114 then generates a resulting histogram (R) by subtracting 2310 the point from the histogram under test, B[x,y], from the reference histogram point, A[x,y], (or vice versa with the appropriate modification to the analysis using FIG. 26). The resulting histogram is separated into the four separate quadrants as described above with reference to FIG. 26.

Figure 24:
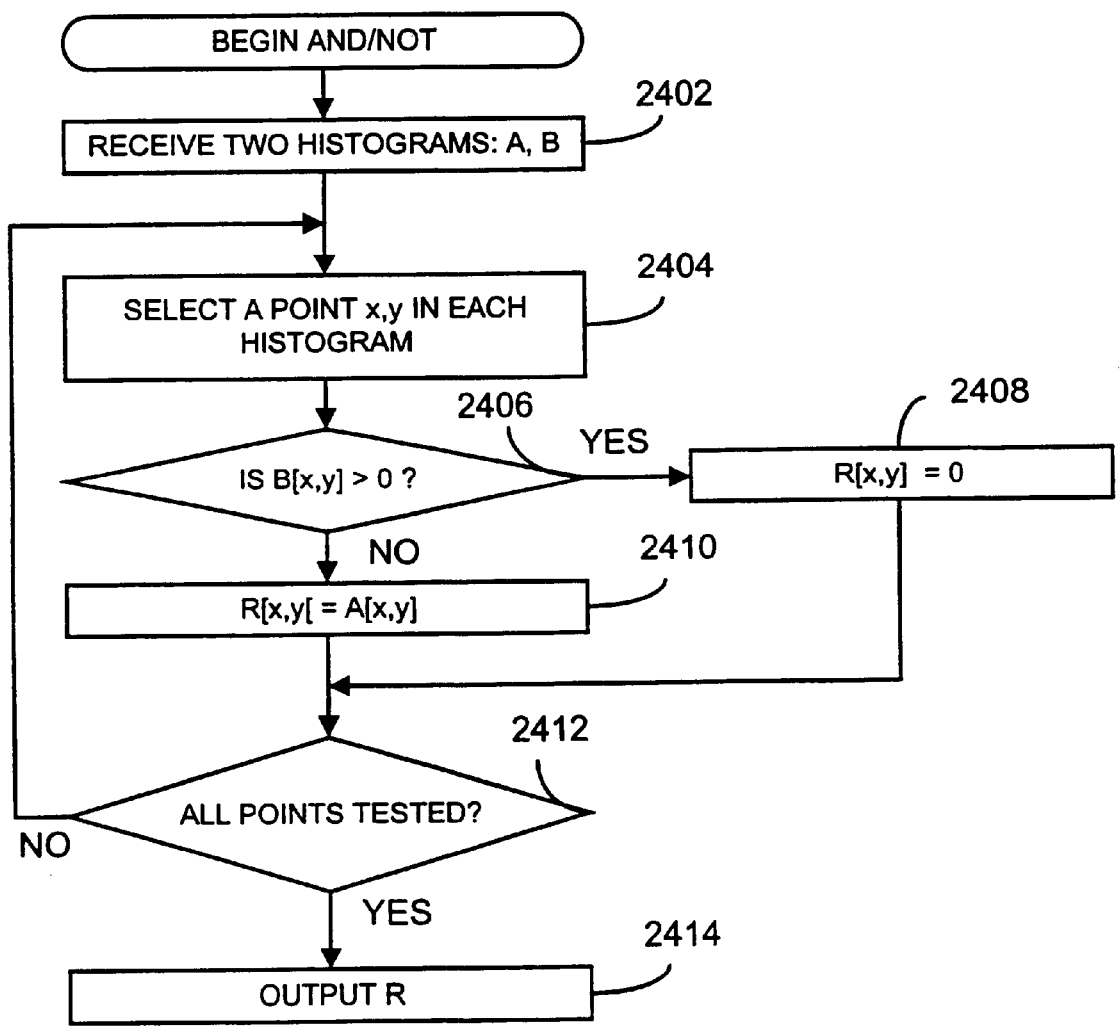
FIG. 24 is a flow chart illustrating the operation of the AND/NOT unit 2116 according to one embodiment of the present invention.

Another embodiment of the present invention uses a reference histogram which a NOT operation is performed between a reference histogram and a data histogram followed by an AND operation. FIG. 24 is a flow chart illustrating the operation of the AND/NOT unit 2116 according to one embodiment of the present invention. The AND/NOT unit 2116 receives 2402 two histograms, e.g., a reference histogram (B) and a data or test histogram (A), as described above. The AND/NOT unit 2116 selects 2404 a point (x,y) in each histogram. If the value of the selected point in the reference histogram is greater than zero then the AND/NOT unit 2116 sets 2408 the corresponding point in the resulting histogram equal to zero. If the value of the selected point in the reference histogram is not greater than zero then the AND/NOT unit 2116 sets the point in the resulting histogram equal to the selected point in the test histogram, i.e., R[x,y]=A[x,y].

The AND/NOT unit 2116 uses a reference histogram in which an AND operation is performed between the reference histogram and the data histogram followed by a NOT operation. This yields a resultant histogram which contains only those regions which are not common to both the data and reference histograms.

The resulting and/not histogram is then segmented as shown above and each quadrant is labeled with the above interpretation. FIG. 27 illustrates one example of histogram analysis according to the AND/NOT unit of the present invention. The data from each histogram quadrant can be traced back to the original data image. The amount of surface area covered in the original images by each of the regions shown in FIG. 27 can be computed and displayed. For example, the total amount of the surface which has carbon wear can be computed from the traceback. The depth of the carbon wear can be computed by calibrating the amount of carbon wear corresponding to the reflectivity change.

The above described process can be applied to the $P_{sum}=P_{scattered}+P_{specular}$ Vs $S_{sum}=S_{scattered}+S_{specular}$ histogram or any of the components: $P_{scattered}$, $P_{specular}$, $S_{scattered}$, $S_{specular}$ in any combination versus any other combination. The reference histogram may be computed from an untested sister disk, the opposite side of the tested disk, a sub-image histogram computed from an undamaged area of the disk under test or from a traceforward computed on an undamaged area of the disk under test, as discussed above.

For example, FIG. 28 illustrates one example of histogram analysis using P specular or S specular versus P scattered or S scattered variable according to the AND/NOT unit of the present invention. In this case the finger 2802 extending into the second quadrant corresponds to corrosion products on the disk surface. The slope of the centroid 2804 of this finger 2802 is related to the index of refraction of the corrosion products. Since different materials have a different index of refraction and hence a different slope, this allows the user to separate debris, corrosion products and texture lines. The second area 2806 along the horizontal axis of FIG. 28 is the region which has been removed via the AND/NOT operation. The amount of the surface covered by debris or texture lines is easily computed by calculating the number of pixels contained in the finger area 2802 of quadrant 2. The finger 2808 corresponds to debris on the disk. The slope of the centroid 2810 of this finger 2808 is related to the index of refraction of the debris on the disk surface. This allows the user to quantitatively separate and identify (from the slope of the centroid) the different particles and corrosion products on the disk. A substantially identically analysis may be computed from a 2-dimensional histogram of the P specular versus the S specular light. In this case the two fingers 2802 and 2808 will be extending into the third quadrant. The two fingers will still be separated by a different slope in a manner substantially identical to FIG. 28.

The above discussion has focused on a means to measure the magnitude of the S and P polarized beams and their appropriate scattered components. A means for improving the sensitivity of existing technology is to add the ability to measure the phase between the S and P components of the wave. The measurement of the phase shift between the S and P components will give a 4 to 20 times improvement in the sensitivity to the measurement of thin films and defects. This can be accomplished by illuminating a thin film disk with linearly or elliptically polarized light that contains both P and S components of light, for example. The detected light can then be analyzed to measure the phase shift between the P and S components. Simultaneously you can also measure the amplitude of the P and S components, the scattered components, and the Magneto-Optic Kerr rotation. If a bi-cell or position sensitive detector is added to the optical design then it is possible to also measure the displacement (height or depth) of features on the surface. Accordingly, one embodiment of the present invention simultaneously performs film thickness measurements, surface roughness measurement, reflectivity measurement, magnetic imaging, and optical profiling. An embodiment of this instrument is shown in FIG. 29.

Figure 29:
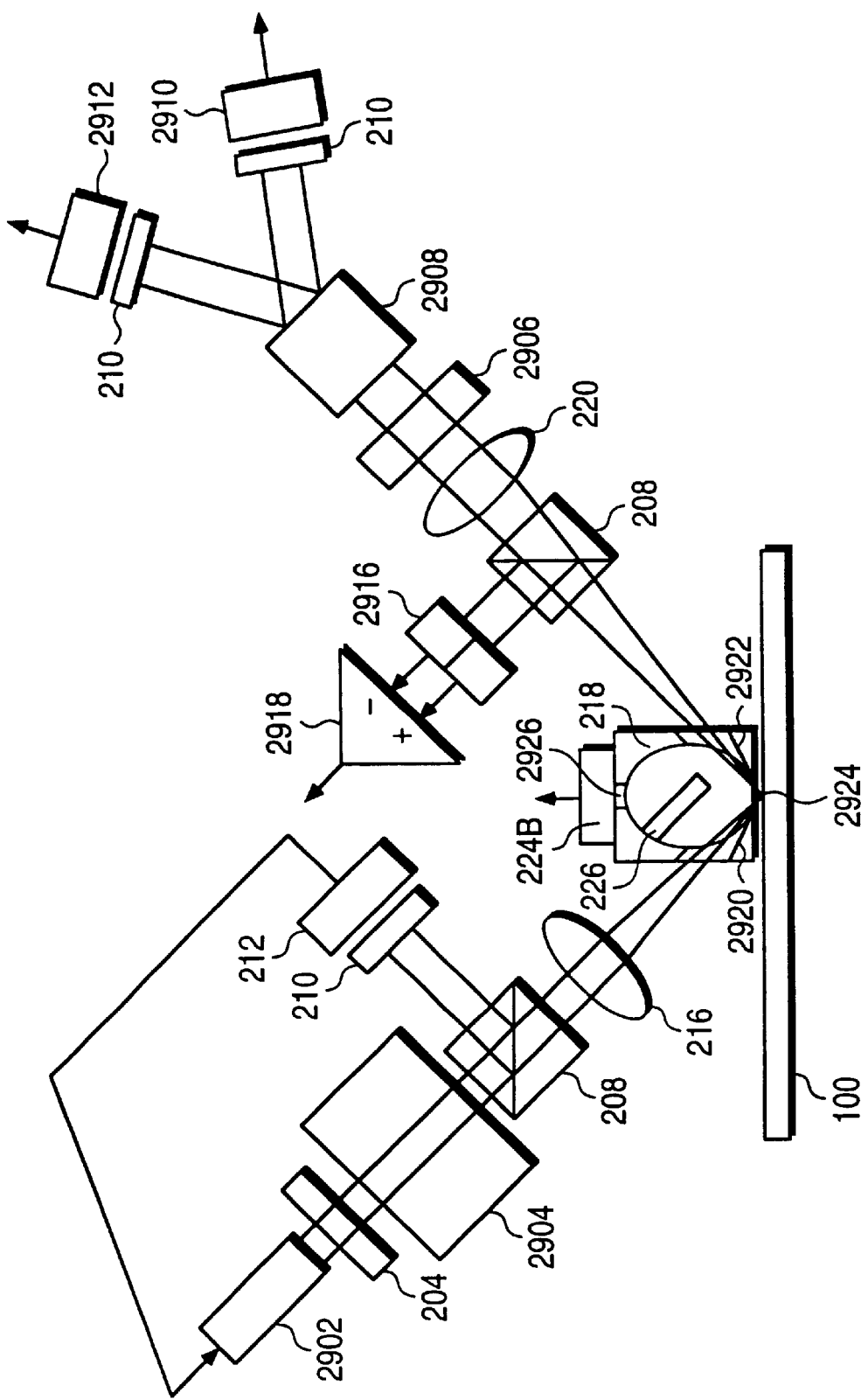
FIG. 29 illustrates an embodiment of the apparatus for measuring the properties of thin films including thickness, reflectivity, roughness, magnetic pattern and surface profile.

FIG. 29 is an illustration of a combined reflectometer, scatterometer, phase shift microscope, magneto-optic Kerr effect microscope and optical profilometer 2900 according to one embodiment of the present invention. This invention uses a multi-mode, multi-wavelength laser diode 2902 which is available from Rohm Co., LTD Kyoto, Japan as model number RLD-78MV and a polarizer 204 which is adjusted for P polarization and improves the extinction ratio of the laser. The next element is a mechanically rotatable half wave plate 2904 that is available from CVI Laser Corp. which can be used to rotate the polarization between 45 degrees, and P or S polarization's. Alternative techniques for rotating the polarization is to rotate the laser diode 2902 or to use a liquid crystal polarization rotator such as model LPR-100 available from Meadowlark Optics, Frederick, CO. The latter embodiment has the advantage of being a purely electronic means of polarization rotation and as a result there is no possibility of beam movement when the polarization is rotated.

The non-polarizing beam splitter 208 is used to provide a reference beam to stabilize the laser diode intensity. The focusing lens 216 creates a small spot on the surface of a thin film disk 100. The integrating sphere 218 is used to measure the scattered light for the purposes of computing the surface roughness and measuring debris or corrosion on the disk surface. The holes in the input 2920 and output 2922 are designed to pass the specular optical beam and collect the scattered light. The low spatial frequency limit of the scattered light is determined by the aperture diameter of the exit hole 2922. The scattered light is measured with a photodetector 224B placed at an exit hole 2926 at the top of the integrating sphere. The integrating sphere 218 has a hole 2924 in the surface nearest the disk to allow the beam to reflect from the surface of the thin film disk 100.

After reflecting from the disk, the beam passes through a non-polarizing beam splitter 208 and approximately one-half of the beam passes into a bi-cell detector 2916 available from UDT Sensors, Inc., Hawthorne, Calif. In one embodiment of the present invention the bi-cell detector includes two identical detectors which are separated by a small distance (typically less than 25 microns of separation). The output of the bi-cell passes into a differential amplifier 2918 that subtracts the two outputs. The subtracted output is digitally normalized by the sum of the outputs of 2912 and 2910 to remove any laser intensity or disk reflectivity changes. The normalized output is proportional to the slope of the surface since differential detector 2916 measures the movement of the beam due to surface slope changes. The resulting image is a two dimensional map of the slope of the surface. The displacement of the surface (height or depth) can be obtained by integrating the slope versus position signal. The signal from the bi-cell 2916 can also be used to provide an autofocus signal for the optical signal. The optical assembly is calibrated and focused when it is first assembled. The reading of the voltage from the differential amplifier 2918 can be recorded in a storage device, e.g., the PC memory. When a different thickness disk 100 is placed beneath the optics a small motor (not shown) can move the head up or down until the differential amplifier 2918 reading is the same as that originally recorded when the optical assembly was first assembled. When this is done the distance of the optical assembly from the disk 100 remains constant and the optical assembly remains in focus.

Figure 34:
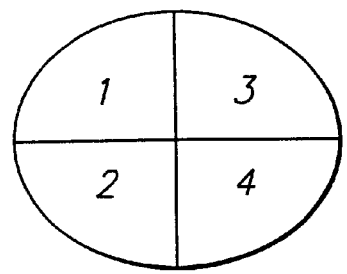
FIG. 34 illustrates the various quadrants of a quad-cell detector used for circumferential and radial optical profiles.

The bi-cell as described above will measure the circumferential profile of the surface. A quad-cell, which is also available from UDT Sensors, Inc. Hawthorne, Calif., may be used to measure both the circumferential and radial profiles of the surface. The quad-cell is a four-element detector with four identical elements as shown in FIG. 34. The two elements (1 and 2 in FIG. 34) which are oriented in the circumferential direction may be summed together to form one half of the bi-cell detector 2916 and the other two elements (3 and 4) may be summed to form the other half of the bi-cell 2916. This configuration will give the circumferential profile as described above. If elements 1 and 3 are summed and 2 and 4 are summed then these two halves may be used to give the radial profile. In this manner both the radial and circumferential profiles may be obtained from a single scan of the surface.

After passing through the non-polarizing beam splitter the other half of the beam is recollimated with a lens 220. It then passes through a mechanically rotatable quarter wave plate 2906 available from CVI Laser Corp. The beam is then polarization split with a Wollaston prism 2908 available from CVI Laser Corp., for example, and each polarization component is detected with a separate photodetector. The plane of the Wollaston prism (the plane of the S and P components) is adjusted at 45 degrees to the plane of incidence. The P component of the beam is directed to a conventional photodiode 2912 available from Hamamatsu Corp., for example, and the S component is directed to a conventional photodiode 2910. The photodiodes have a diffuser 210 placed in front of them to reduce the residual position sensitivity of the photodiodes. The difference between the photodetectors is proportional to the cosine of the phase difference between the S and P waves coming from the Wollaston prism. As a result this instrument can get different types of information when used in different modes.

When the polarization is adjusted to P, the P specular and P scattered light is measured resulting in sensitive measurements of carbon thickness and carbon wear. The P specular signal is obtained by rotating the half wave plate 2904 so that the incident polarization is P. The P specular signal is given by the sum of the signal from 2912 and 2910. When the polarization is adjusted to 45 degrees (exactly between P and S polarization) the instrument is most sensitive to measurements of the phase change induced by changes in the thickness of the thin films on the disk surface. In the phase shift mode the instrument measures lubricant thickness and carbon thickness on thin film disks. The phase shift is measured by taking the difference between the signals measured at 2912 and 2910. This gives an output that is proportional to the cosine of the phase difference between the S and P components of the wave. The orientation of the quarter wave plate 2906 is adjusted to optimize the sensitivity to lubricant and carbon wear or thickness. The individual components may also be measured; that is, the S and P components of the 45 degrees polarized light. These are measured simultaneously with the phase shift and the scattered light.

Figure 31:
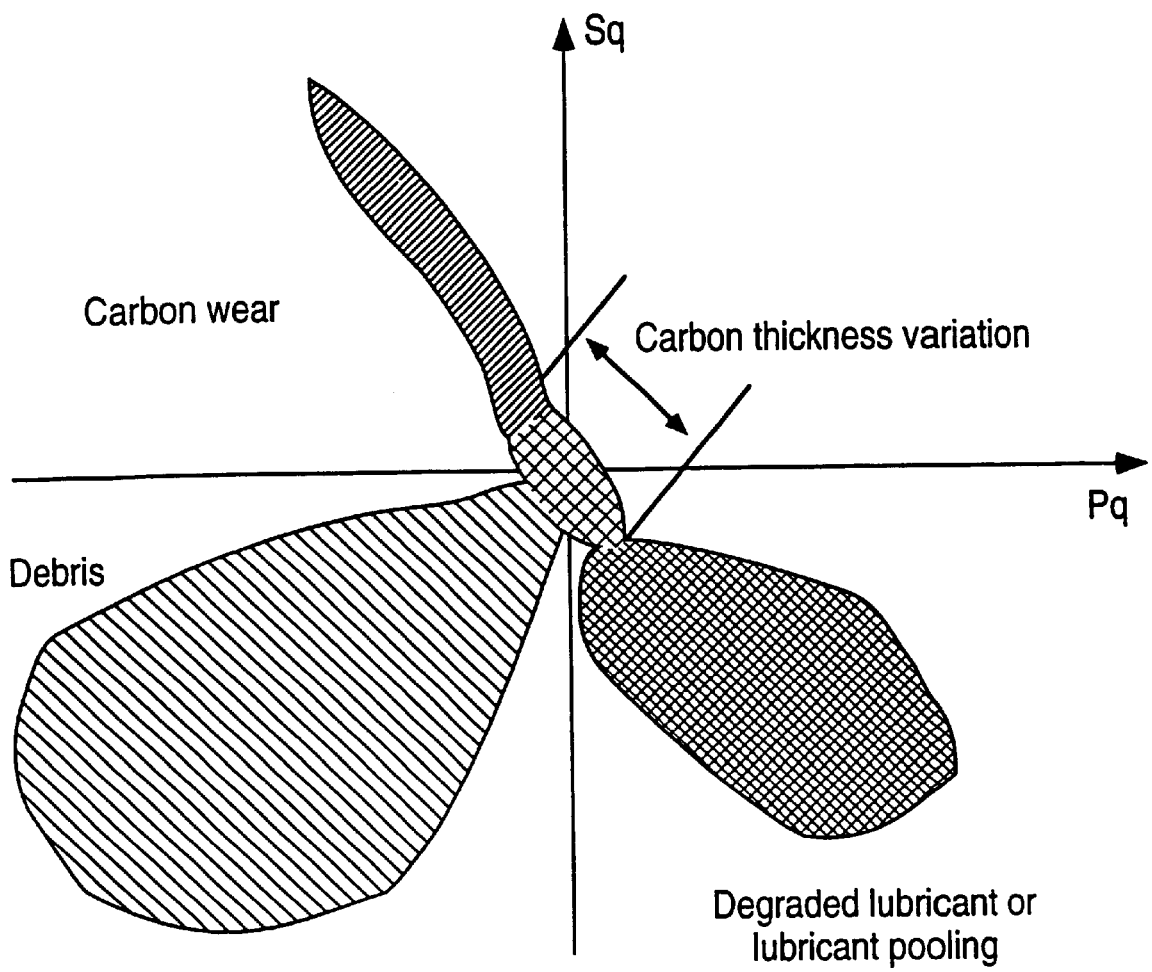
FIG. 31 illustrates the interpretation of the phase shift data in a two-dimensional concentration histogram of $P_Q$ versus $S_Q$ for 45 degree linearly polarized light.

The S and the P components of the 45 degree linearly polarized light are referred to as $S_Q$ and $P_Q$. When these components of the phase shift are plotted in a two dimensional concentration histogram the interpretation of the data becomes as shown in FIG. 31. Carbon wear is seen in the second quadrant, carbon thickness variation on the disk surface is the length of the body of the histogram, debris is in the third quadrant, and degraded lube and lube pooling is in the fourth quadrant.

When the polarization is adjusted to S polarization the instrument will be able to measure the S specular and the S scattered light and, as a result, obtain the surface roughness and other properties of the sample. The S specular signal is given by the sum of the signal from 2912 and 2910. The angle of incidence shown in FIG. 29 is 58 degrees but angles greater or less than 58 degrees will work as well. The longitudinal Kerr effect can be measured by operating the instrument in any of the linear polarization's, i.e., P, S or 45 degrees. Rotating the quarter wave plate 2906 to achieve maximum sensitivity to the magnetic pattern optimizes the Kerr effect signal. The orientation of the quarter wave plate which optimizes the Kerr effect may be different from that which optimizes for lubricant and carbon sensitivity. As a result the quarter wave plate is made to be removable, for example, so that two different and separately optimized plates can be used for the different applications. A different embodiment would have a miniature motor to rotate the orientation of the quarter wave plate so as to optimize the signal for the Kerr effect or lubricant and carbon mode. The different polarization's will require a different quarter wave adjustment to achieve optimization. When in this mode the instrument functions as a Kerr effect microscope. In an embodiment the S polarization is used to image the longitudinal Kerr effect.

Figure 30:
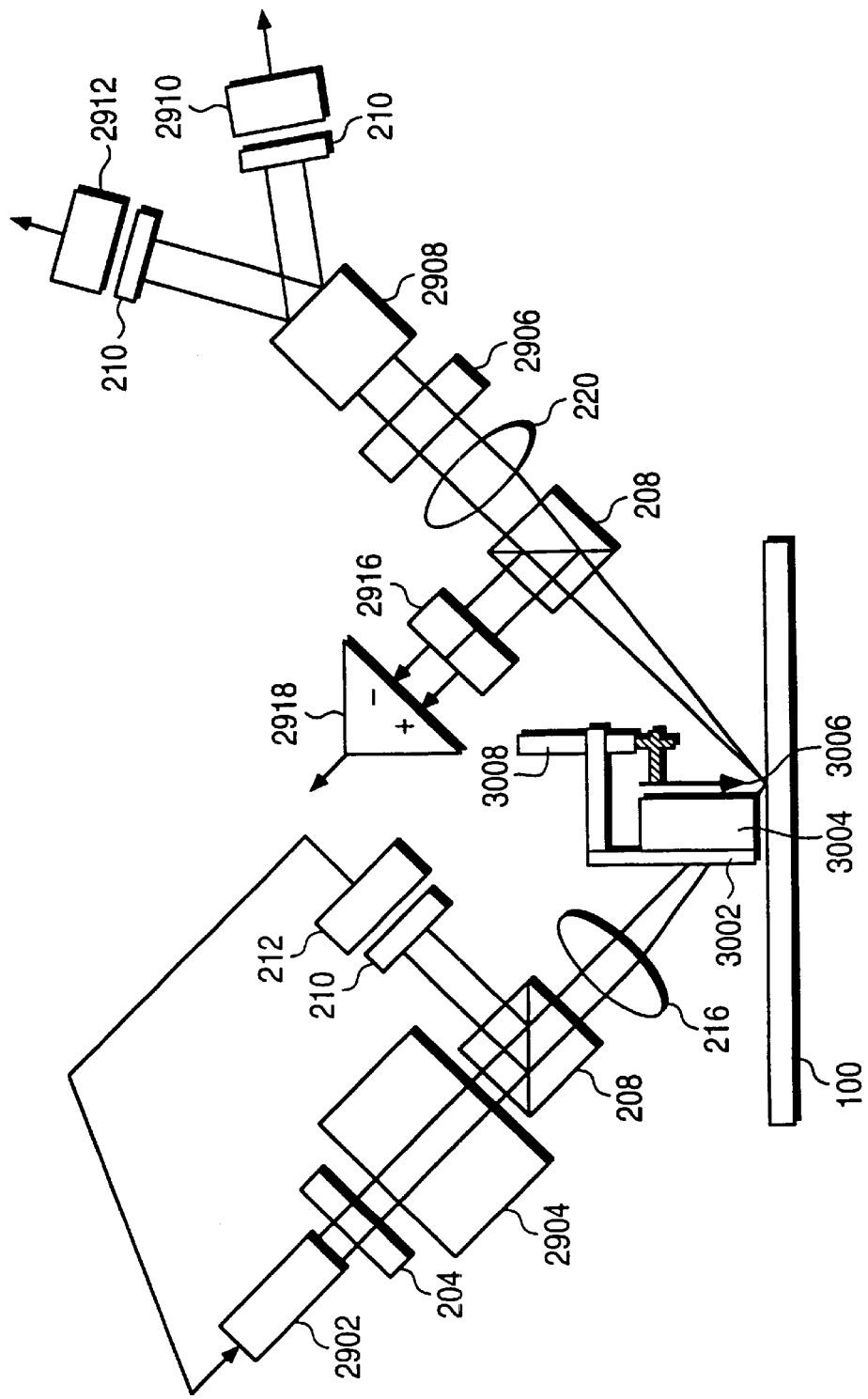
FIG. 30 illustrates an embodiment of the apparatus for measuring the properties of thin films and the ability to scribe defects.

When a defect is observed on a disk with the instrument described in FIG. 29 then it is desirable to be able to mark the position of the defect with a mechanical scribe. Such a scribe is shown in FIG. 30. The integrating sphere 218 and related components have been removed from the drawing in order to clearly show the scribe. In the actual instrument both the scribe and the integrating sphere are present. The scribe consists of a supporting apparatus 3002, a linear slide 3004, a diamond scribe 3006 and an air cylinder actuator 3008. The air cylinder actuator holds the diamond scribe away from the surface until it receives a command from a PC to release the scribe. The scribe is attached to the same optical body that holds the optical components of FIG. 29. This means that the scribe can use the same linear stage as the optical body during the scribing process. A process of marking a disk with a scribe is as follows: (1) locate the defect with the instrument described in FIG. 29; (2) from the image displayed on the PC video monitor indicate to the software that this is the defect to be marked (scribed); (3) the software then rotates the disk 100, which is attached to a spindle with an encoder, so that the defect is at the same angle as the scribe; (4) the scribe is moved to the radius of the defect with the stage which moves the optical head and when in the close vicinity of the defect the air cylinder actuator is activated and the scribe drops onto the surface; (5) the stage is moved a specified distance with the scribe in contact with the disk, this leaves a mark in the vicinity of the defect. This mark can be used to find the defect for subsequent analysis. Multiple marks can be placed in the vicinity of the defect if desired.

The instrument described in FIGS. 29 and 30 can simultaneously measure the optical profile (height and depth) of the surface, the S and P components of the reflectivity, the phase shift between the P and S waves and the scattered light. It is also capable of measuring the Magneto-optic Kerr effect of magnetic films and it has the ability to scribe defects for later analysis.

The measurement of the phase shift between the S and P components of the optical wave requires a means to stabilize the long-term phase drift of the diode laser. This can be accomplished by the use of a reference mirror. The reference mirror is a stable optical surface such as a gold mirror or a section of a thin film disk. The reference mirror is calibrated when the instrument is first set up by measuring and recording the phase shift of the reference mirror. At times after the initial calibration of the instrument the reference mirror is measured prior to a measurement of the sample. Any deviation of the reference mirror reading from the initial reading is recorded and subtracted from the measurement of the sample readings. This insures that the phase shift reading from the surface under measurement (the thin film disk 100) will remain stable over time. The same procedure can also be applied to the measurement of the S specular and P specular signals. In this case the when the instrument is calibrated the values of the P specular and S specular signals measured on the reference mirror are recorded and deviations from these values are used to correct the specular data. This removes any drift from the P and S specular signals.

The above discussion is relating to an instrument, which has an angle of incidence that is near 60 degrees from the vertical. Similar ideas can be applied to a machine operating at angles less than or greater than 60 degrees. When the angle of incidence changes the interpretation of the various quadrants of the histogram will change according to the discussion given earlier.

Figure 32:
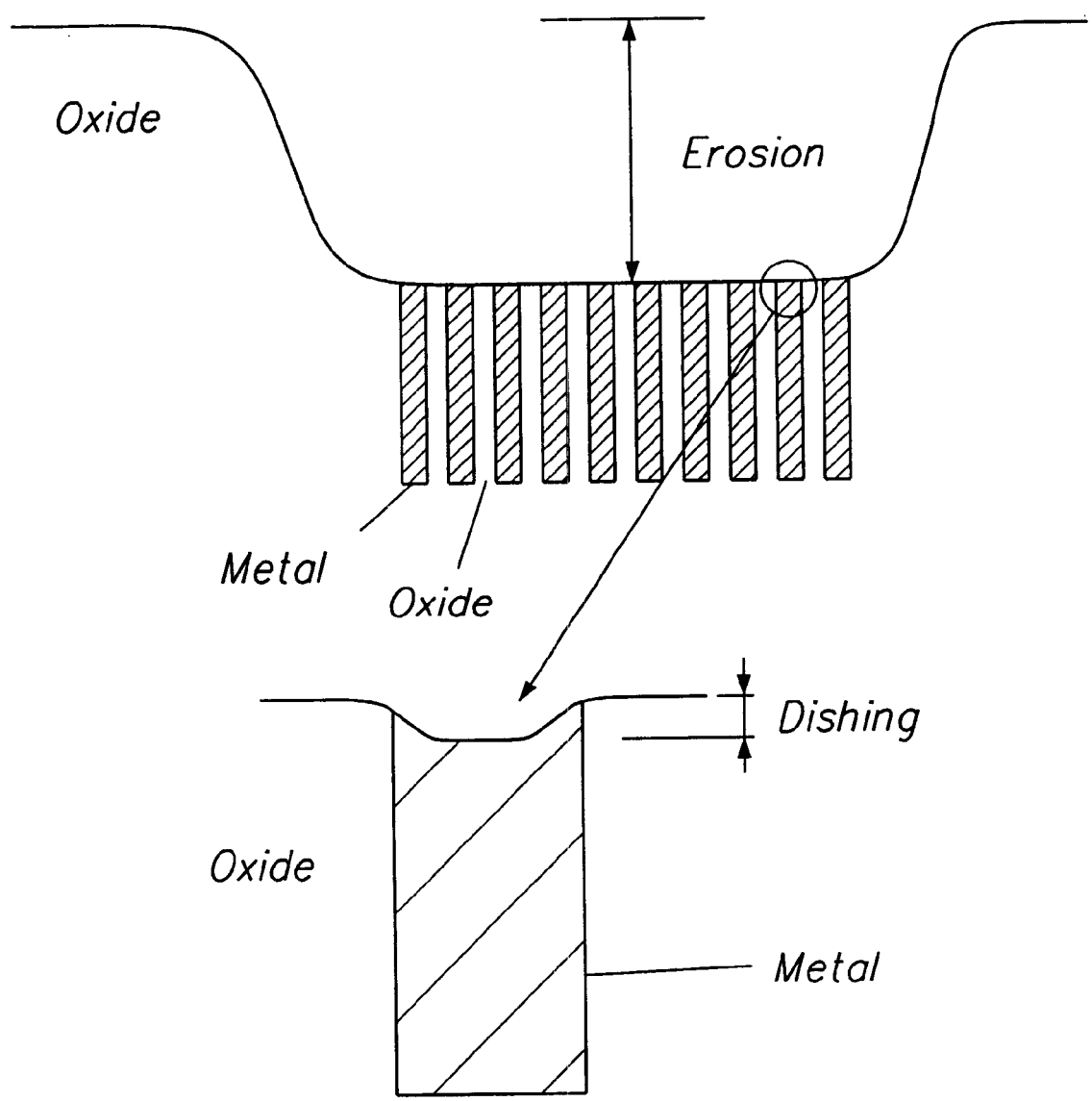
FIG. 32 illustrates a schematic representation of erosion and dishing on a CMP polished silicon wafer.
Figure 33:
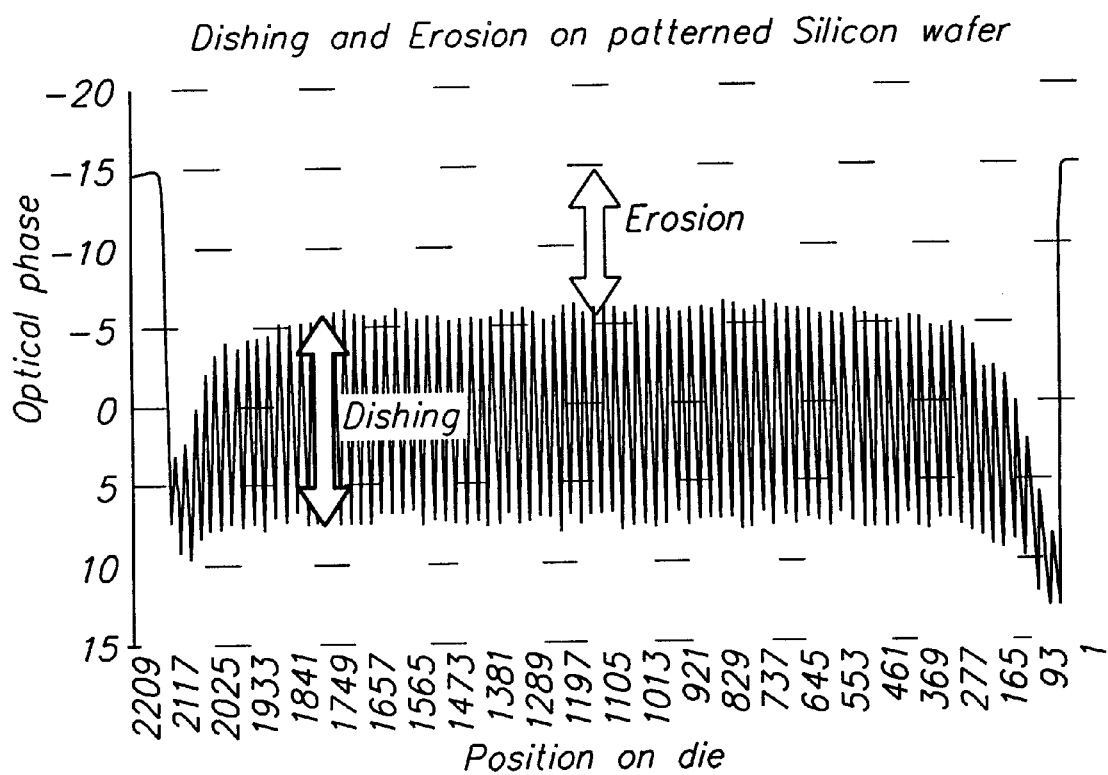
FIG. 33 illustrates the actual measurement of phase shift (proportional to film thickness) versus position on a die on a patterned silicon wafer. The figure also illustrates the definitions of dishing and erosion.

As describe above, not only can this invention measure thin films on magnetic disks but it can also measure the same parameters on silicon semiconductor wafers. More particularly, the present invention can measure the film thickness, surface profile, surface scatter from defects, areas contaminated with unwanted thin films or particles and reflectivity changes due to missing or damaged films. One example of a semiconductor application is the measurement of the properties of the chemical mechanical polishing process (CMP). The CMP process is used to planarize the surface of a coated and patterned silicon wafer. To control the CMP process engineers want to measure the amount of material removed from the metal region as compared to the oxide region. Since the oxide and the metal areas have different mechanical properties they will polish at different rates. This results in what is commonly known as "dishing" and "erosion". Erosion is the average amount of displacement of the polished metal lines below the surrounding oxide surface as a result of CMP polishing. The narrow metal lines are interspersed with oxide and the amount of displacement of the metal lines below their immediate surrounding oxide is known as dishing. An illustration of this is shown in FIG. 32. CMP process engineers wish to control the amount of dishing and erosion. FIG. 33 illustrates the measurement of dishing and erosion by the measurement of the optical phase shift versus position on a die on a patterned silicon wafer. The erosion shown on FIG. 33 is greatest nearest the edge of the metal, that is at positions 93 and 2117. At these same positions the dishing is a minimum. The optical phase shift directly measures the thickness changes of the oxide. Therefore in the phase shift mode the assumption is that the layer beneath the oxide is flat. The same dishing and erosion can be measured with the optical profilometer 2900, described above. The optical profilometer 2900 directly measures the slope changes on the surface due to erosion and dishing. The slope may be integrated to give the actually optical profile. The advantage of the optical profiler is that it gives the height changes independent of any thickness changes of the underlying films.

While conventional systems have used a mechanical profiler to measure the same parameters as shown in FIG. 33 some of the advantages of the present invention are that it can measure the entire silicon wafer in approximately one minute and is capable of generating a three dimensional image as opposed to merely generating a single line scan as is generated by conventional mechanical profilers. The three-dimensional image of the entire wafer gives the user process uniformity information. That is, the user can rapidly determine how the polishing process is varying across the diameter of the wafer. This valuable information is very difficult and time consuming to generate using conventional mechanical profilers.

Another benefit of the present invention is that the instrument has a small footprint that allows it to be integrated within an existing silicon process or metrology machine. For example, it can be placed within a CMP machine in place of the wafer flat or notch finder module. This means that this invention will use no more clean room floor space than current process or metrology machines.

Figure 35:
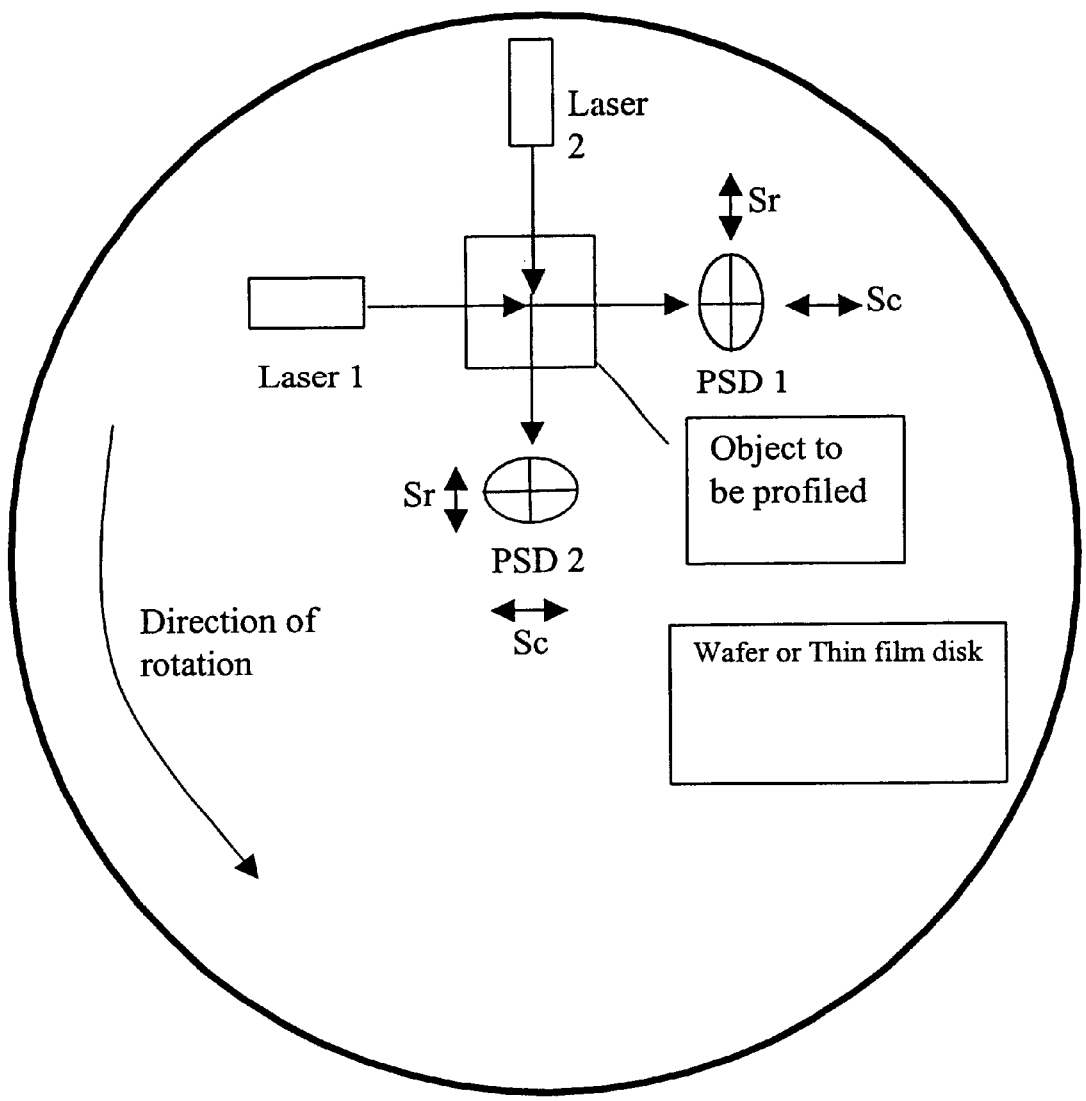
FIG. 35 is a top view of an optical profilometer which measures height or slope according to one embodiment of the present invention.

FIG. 35 shows the top view design of an optical profilometer, which measures height only and measures height directly. It can also measure the slope of the surface independent of height. This differs from previous optical profilometers that measure both slope and height at the same time. With such systems the height is obtained from the slope data by integrating the slope information. However, if the slope information is contaminated with height information then the integration will not give the correct surface profile. The problem is to obtain data that contains only height information and not a combination of both slope and height. The design illustrated and described with reference to FIGS. 35–38 accomplishes this by using two lasers and two position sensitive detectors (PSD) oriented at right angles to one another.

The position sensitive detectors (PSD) are quadrant detectors that are oriented as shown in FIG. 35. The PSD's measure the displacement of the beam in the radial and circumferential directions by subtracting the appropriate PSD quadrants. As the laser beam moves along the surface of the object to be measured, the roughness and waviness of the surface cause the laser beam to "wiggle" on the quadrant detector in response to the slope of the surface. The quadrant detector measures this by subtracting the sum of one pair of quadrants from the sum of another pair. For example, referring to FIG. 37, the slope of the surface in the circumferential direction is given by $[(A1+B1)-(C1+D1)]/[A1+B1+C1+D1]$ where the sum of the four quadrants in the denominator is used to normalize for reflectivity differences. At the same time, if the average distance of the surface from the detector changes, then the average position of the beam on the quadrant detector will change. The resulting difference signal in the above equation will register a slope change when in fact a difference in surface height is occurring. The problem is to be able to separate slope changes from height changes. This can be accomplished by considering the slope in the radial direction, which is obtained by referring to FIG. 37 and is given by $[(A1+D1)-(B1+C1)]/[A1+B1+C1+D1]$. The equation for the radial slope measures the "wiggle" of the beam in the radial direction. In the case of the radial slope, if the average distance of the surface from the detector changes then the beam simply moves along the line separating A1+D1 from B1+C1. As a result the radial slope signal does not change when the surface height changes and the equation for the radial slope records only slope and not height changes.

When the orientation of the laser beam is rotated by 90 degrees (as with laser 2 and PSD 2 in FIG. 35) the behavior of the radial and circumferential slope will reverse. In the case of laser 2 and PSD 2 the circumferential slope equation will record only slope changes and not height changes. On the other hand, for laser 2, the radial slope equation will record both slope and height changes. Since the output beam of both lasers 1 and 2 is positioned at the same location on the surface (as shown in FIG. 35) then it is possible to subtract the radial slope equation from laser 1 and PSD 1 from the radial slope equation from laser 2 and PSD 2. The resulting subtraction will contain only height information and no slope information. It is also possible to obtain the same information by subtracting the circumferential slope equation from laser 1 and PSD 1 from the circumferential slope equation from laser 2 and PSD 2. The radial slope (with no height information) can be obtained by choosing the radial slope equation from laser 1 and PSD 1. The circumferential slope (with no height information) can be obtained by choosing the circumferential slope equation from laser 2 and PSD 2. In this manner it is possible to independently measure surface height variation and slope variation.

Figure 36:
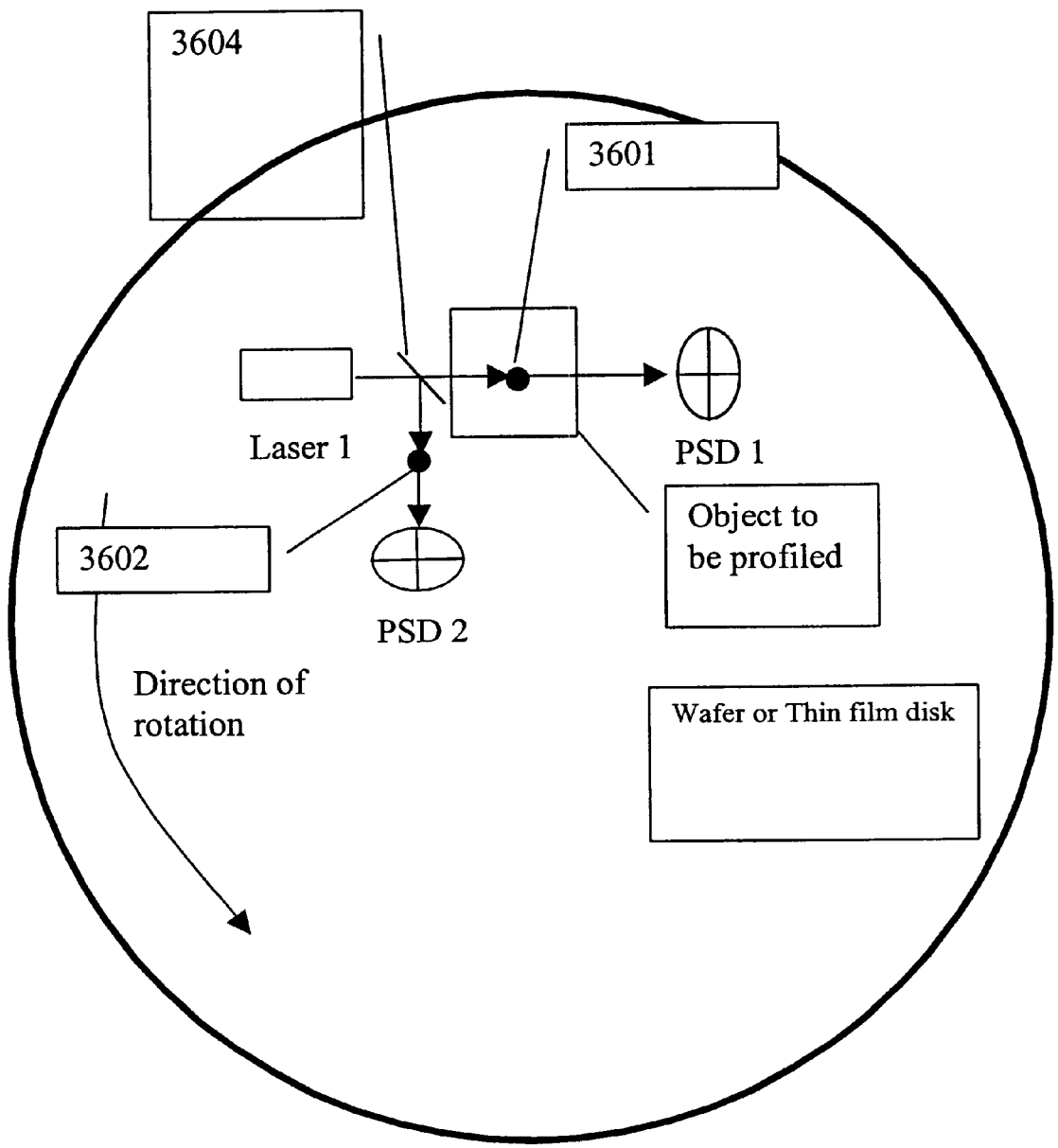
FIG. 36 is a top view of an optical profilometer having a single laser which measures height or slope according to another of the present invention.

In another embodiment of this optical profilometer, as shown in FIG. 36, a single laser is used and a 50/50 mirror 3604 oriented at a compound angle directs a second beam onto the surface to a position labeled 3602 on FIG. 36. The beam that passes through the 50/50 mirror 3604 is directed onto the surface to a position labeled 3601 on FIG. 36. The entire surface of the object to be measured is scanned with both of the beams resulting in at least two images of the surface. The resulting images are stored and digitally shifted so that the resulting images have the object to be profiled at the same x, y location. The resulting shifted images may then be subtracted to give the height profile in the manner described above. The advantage of this embodiment is that it uses only a single laser and fewer optical components and the beam shape of the two beams is identical.

Laser one and PSD 1 nominally measure the signal in the radial, Sr, and the signal in the circumferential, Sc, directions. However, the nature of the PSD results in Sc from laser one and PSD 1 being contaminated with height information, in addition to slope information. Sr from laser 1 and PSD 1 include only slope information. Laser two and PSD 2 also nominally measure the slope in the radial and circumferential directions. However, Sr from laser 2 and PSD 2 measures both slope and height at the same positions as Sr from laser 1 and PSD 1. As a result the true height variation can be obtained by subtracting Sr from laser 2 and PSD 2 from Sr from laser 1 and PSD 1. That is, the slope information is removed when subtracting Sr from PSD 2 from Sr from PSD 1, leaving only the height information.

A similar result can be obtained from subtracting Sc from PSD 2 that only contains slope information. As a result, subtracting Sc from PSD 2 from Sc from PSD 1 gives data containing only height information. The result is a direct measurement of height. The advantages of this technique are that it gives a direct measurement of height and it can be done in a non-contact manner at high speed. This technique can also measure step heights with 90-degree step angles. Conventional systems, which use slope measurements, cannot measure 90-degree step heights.

Figure 37:
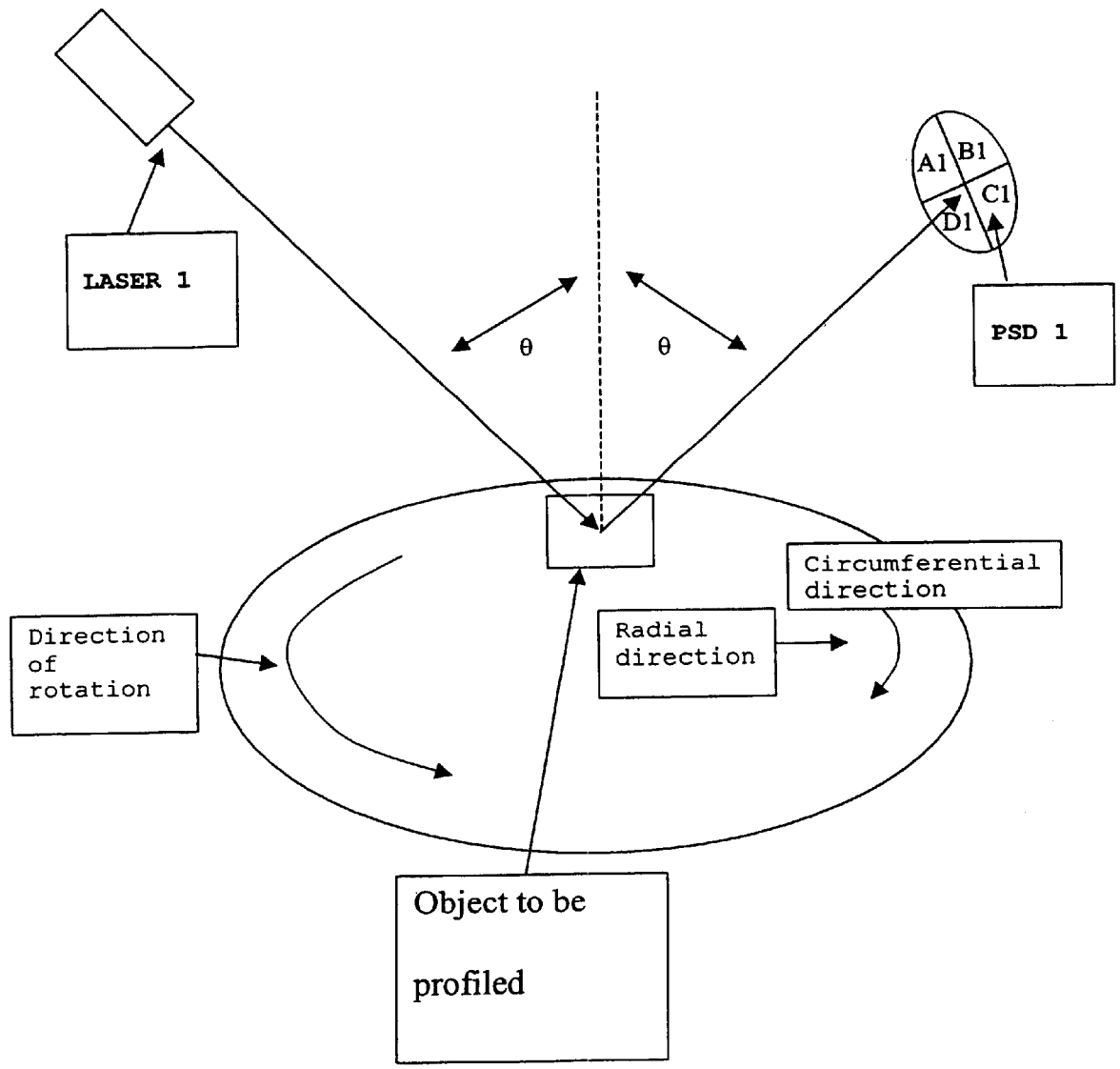
FIG. 37 is a side view of optical profilometer showing laser one and PSD 1 according to one embodiment of the present invention.

FIG. 37 shows the side view design of the optical profilometer. This figure only shows laser 1 and PSD 1 in an effort to easily show the side view design. In FIG. 37 one can see that the optical profilometer is positioned above a thin film disk or wafer and is translated in the radial direction while the disk or semiconductor wafer is rotated.

Figure 38:
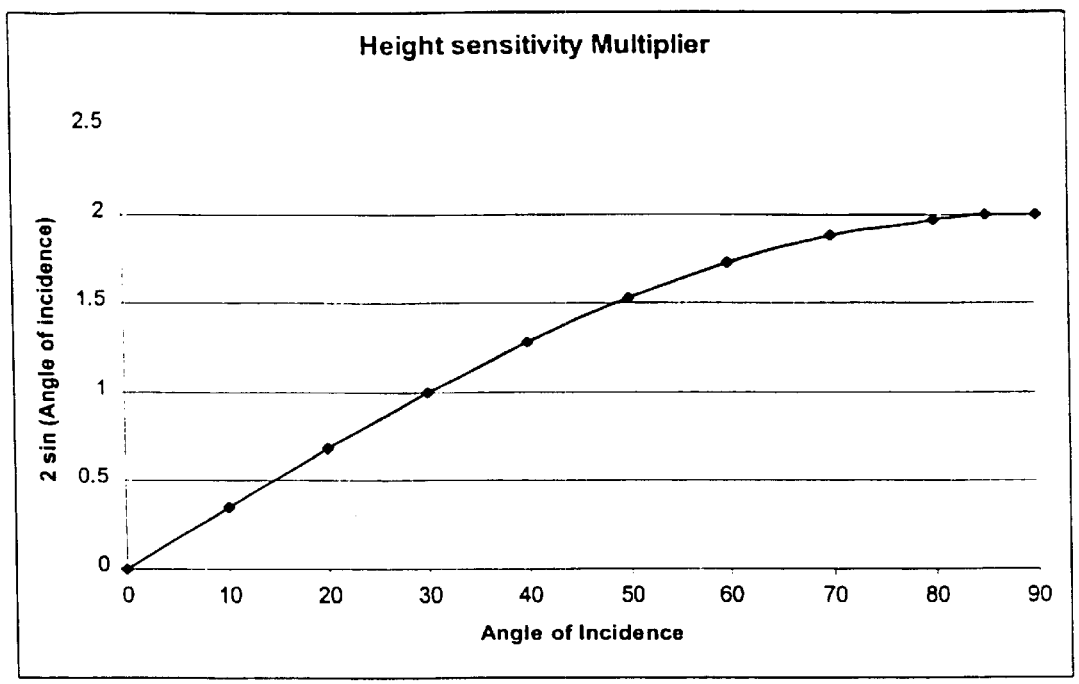
FIG. 38 illustrates the height sensitivity multiplier as a function of angle of incidence (theta) according to one embodiment of the present invention.

The angle of incidence ($\theta$) shown in FIG. 37 can be chosen for the particular application. Any angle of incidence can be chosen except normal incidence, where the PSD's would have no height sensitivity. For an application that involves transparent substrates one could choose angles greater than 45 degrees in order to increase the reflection signal from the surface. As the angle of incidence increases, the height sensitivity also increases by the factor $\sin(\theta)/\cos^2(\theta)$. A plot of this factor is shown in FIG. 38. This suggests that an angle of incidence greater than or equal to approximately 60 degrees would be optimal, although not necessary. At angles greater than 60 degrees the sensitivity will increase and the signal from a transparent surface will increase. This invention requires that the focused spot sizes of the two lasers be substantially identical and that the laser spots overlap as closely as possible.

While the invention has been particularly shown and described with reference to a preferred embodiment and several alternate embodiments, it will be understood by persons skilled in the relevant art that various changes in form and details can be made therein without departing from the spirit and scope of the invention.

What is claimed is:

1. A system for measuring a height of an object comprising:

a first electromagnetic signal source for transmitting a first signal toward a first position on the object at a first angle;

a second electromagnetic signal source for transmitting a second signal toward the first position on the object at a second angle;

a spinning device for rotating the object to change the first position;

a first position sensitive detector to receive a portion of said first signal that reflects off of said object, and to determine a radial portion of said first signal (S1r) and a circumferential portion of said first signal (S1c);

a second position sensitive detector positioned at a right angle from said first position sensitive detector, to receive a reflected portion of said second signal that reflects off of said object, and to determine a radial portion of said second signal (S2r) and a circumferential portion of said second signal (S2c);

a processor for determining the height of the first position based upon a difference between S2r and S1r that does not include slope information.

2. The system of claim 1, wherein said object is one of a thin film disk and a substrate.

3. The system of claim 1, wherein said object is a silicon wafer.

4. The system of claim 1, wherein said object is an optical component.

5. The system of claim 1, wherein said first and second electromagnetic signal sources are lasers.

6. The system of claim 1, wherein said height measurement is a performed without said laser and said position sensitive detectors contacting the object.

7. The system of claim 1, for measuring the height of said object at the first position wherein a slope is ninety degrees, said slope representing the change in height between the first position and an adjacent position on the object.

8. A method for measuring a height of an object comprising the steps of:

transmitting a first signal toward a first position on the object at a first angle;

transmitting a second signal toward the first position on the object at a second angle;

rotating the object to change the first position;

receiving at a first position sensitive detector a portion of said first signal that reflects off of said object, and to determine a radial portion of said first signal (S1r) and a circumferential portion of said first signal (S1c);

receiving at a second position sensitive detector positioned at a right angle from said first position sensitive detector, a reflected portion of said second signal that reflects off of said object, and to determine a radial portion of said second signal (S2r) and a circumferential portion of said second signal (S2c);

determining the height of the first position based upon a difference between S2c and S1c that does not include slope information.

9. The method of claim 8, wherein said object is one of a thin film disk and a substrate.

10. The method of claim 8, wherein said object is a silicon wafer.

11. The method of claim 8, wherein said object is an optical component.

12. The method of claim 8, wherein said first and second electromagnetic signal sources are lasers.

13. The method of claim 8, wherein said height measurement is a performed without said laser and said position sensitive detectors contacting the object.

14. The method of claim 8, wherein the slope at the first position is ninety degrees, said slope representing the change in height between the first position and an adjacent position on the object.

15. A system for measuring a slope of a surface of an object comprising:

a first electromagnetic signal source for transmitting a first signal toward a first position on the object at a first angle;

a second electromagnetic signal source for transmitting a second signal toward the first position on the object at a second angle;

a spinning device for rotating the object to change the first position;

a first position sensitive detector to receive a portion of said first signal that reflects off of said object, and to determine a radial portion of said first signal (S1r) and a circumferential portion of said first signal (S1c);

a second position sensitive detector positioned at a right angle from said first position sensitive detector, to receive a reflected portion of said second signal that reflects off of said object, and to determine a radial portion of said second signal (S2r) and a circumferential portion of said second signal (S2c);

a processor for determining the slope at the first position based upon a difference between S2r and S1r that does not include height information.

16. The system of claim 15, wherein said object is one of a thin film disk and a substrate.

17. The system of claim 15, wherein said object is a silicon wafer.

18. The system of claim 15, wherein said object is an optical component.

19. The system of claim 15, wherein said first and second electromagnetic signal sources are lasers.

20. The system of claim 15, wherein said slope measurement is a performed without said laser and said position sensitive detectors contacting the object.

21. The system of claim 15, for measuring the slope of said object at the first position wherein a slope is ninety degrees, said slope representing the change in height between the first position and an adjacent position on the object.

22. A method for measuring a slope of a surface of an object comprising the steps of:

transmitting a first signal toward a first position on the object at a first angle;

transmitting a second signal toward the first position on the object at a second angle;

rotating the object to change the first position;

receiving at a first position sensitive detector, a portion of said first signal that reflects off of said object, and to determine a radial portion of said first signal (S1r) and a circumferential portion of said first signal (S1c);

receiving at a second position sensitive detector positioned at a right angle from said first position sensitive detector, a reflected portion of said second signal that reflects off of said object, and to determine a radial portion of said second signal (S2r) and a circumferential portion of said second signal (S2c);

determining the slope at the first position based upon a difference between S2c and S1c that does not include height information.

23. The method of claim 22, wherein said object is one of a thin film disk and a substrate.

24. The method of claim 22, wherein said object is a silicon wafer.

25. The method of claim 22, wherein said object is an optical component.

26. The method of claim 22, wherein said first and second electromagnetic signal sources are lasers.

27. The method of claim 22, wherein said slope measurement is a performed without said laser and said position sensitive detectors contacting the object.

28. The method of claim 22, wherein a slope at the first position is ninety degrees, said slope representing the change in height between the first position and an adjacent position on the object.

* * * * *

UNITED STATES PATENT AND TRADEMARK OFFICE
CERTIFICATE OF CORRECTION

PATENT NO. : 6,392,749 B1
DATED : May 21, 2002
INVENTOR(S) : Steven W. Meek and Rusmin Kudinar It is certified that error appears in the above-identified patent and that said Letters Patent is hereby corrected as shown below:

Column 35,
Lines 44-45, replace "$\sin(\theta)/\cos^2(\theta)$" with -- $2\sin(\theta)$. --

Signed and Sealed this

Third Day of December, 2002

JAMES E. ROGAN
*Director of the United States Patent and Trademark Office*